United States Patent [19]

Leonardi et al.

[11] Patent Number: 5,403,842
[45] Date of Patent: Apr. 4, 1995

[54] BENZOPYRAN AND BENZOTHIOPYRAN DERIVATIVES

[75] Inventors: Amedeo Leonardi, Milan; Gianni Motta, Barlassina; Carlo Riva, Varese; Rodolfo Testa, Milan, all of Italy

[73] Assignee: Recordati S.A., Chemical and Pharmaceutical Company, Chiasso, Switzerland

[21] Appl. No.: 888,775

[22] Filed: May 26, 1992

[30] Foreign Application Priority Data

Feb. 25, 1992 [IT] Italy ................ MI92A0408

[51] Int. Cl.⁶ .................. A61K 31/495; A61K 31/50; C07D 403/00
[52] U.S. Cl. ...................... 514/252; 524/253; 544/295; 544/359; 546/196; 546/202; 549/23; 549/400; 549/403
[58] Field of Search ............. 544/295, 359; 514/253, 514/252

[56] References Cited

U.S. PATENT DOCUMENTS

| | | | |
|---|---|---|---|
| 2,921,070 | 1/1960 | da Re | 544/359 |
| 3,277,094 | 10/1966 | Werner | 514/255 |
| 3,350,411 | 10/1967 | da Re | 544/359 |
| 3,810,896 | 5/1974 | Witte et al. | 544/359 |
| 4,495,198 | 1/1985 | Wu | 514/456 |
| 4,539,318 | 6/1984 | Baldwin | 514/222 |
| 4,668,804 | 5/1987 | Wu | 549/403 |
| 4,668,805 | 5/1987 | Wu | 549/403 |
| 4,684,651 | 8/1987 | Kikumoto | 514/253 |
| 4,797,498 | 1/1989 | Albrecht | 549/403 |
| 4,940,711 | 7/1990 | Nardi et al. | 514/255 |

FOREIGN PATENT DOCUMENTS

| | | |
|---|---|---|
| 0017352 | 10/1980 | European Pat. Off. . |
| 0064165 | 11/1982 | European Pat. Off. . |
| 0072620 | 2/1983 | European Pat. Off. . |
| 0081621 | 6/1983 | European Pat. Off. . |
| 0100250 | 2/1984 | European Pat. Off. . |
| 0107804 | 5/1984 | European Pat. Off. . |
| 0108986 | 5/1984 | European Pat. Off. . |
| 206802 | 12/1985 | . |
| 190015 | 8/1986 | European Pat. Off. . |
| 270342 | 6/1988 | European Pat. Off. . |
| 288077 | 10/1988 | European Pat. Off. . |
| 104614 | 4/1989 | European Pat. Off. . |
| 0333676 | 9/1989 | European Pat. Off. . |
| 0343961 | 11/1989 | European Pat. Off. . |
| 364350A | 4/1990 | European Pat. Off. . |
| 372305A | 6/1990 | European Pat. Off. . |
| 0401653 | 12/1990 | European Pat. Off. . |
| 0430693A | 6/1991 | European Pat. Off. . |
| 435749A | 7/1991 | European Pat. Off. . |
| 0546177 | 2/1992 | European Pat. Off. . |
| 0496692A1 | 7/1992 | European Pat. Off. . |
| 61-238783 | 10/1986 | Japan . |
| 05125024-A | 11/1991 | Japan . |
| 4-077567/10 | 7/1992 | Japan . |
| 1166595 | 10/1969 | United Kingdom . |
| 2073738 | 10/1981 | United Kingdom . |
| 2161807 | 1/1986 | United Kingdom . |
| 2193633 | 2/1988 | United Kingdom . |
| 9119707 | 12/1991 | WIPO . |

OTHER PUBLICATIONS

Chemical Abstracts 98:107161d (1983).
Gartside et al., *European Journal of Pharmacology* 191:391–400, 1990.
Hamon et al., *Annals New York Academy of Sciences*, pp. 114–131 1990.
Traber et al., *TIPS* 8:432–437, Nov., 1987.
Frishman et al., *Cardiovascular Pharmacotherapy II*, 72:427–440, No. 2, Mar. 1988.
Da Re et al., *J. Med. Chem.* 2:263–9, No. 3, 1960.
Uneyama et al., *Bull. Chem. Soc. Jpn.* 58:2361–65, 1985.
Da Re, *Il Farmaco-Ed. Sc.*–vol. XI, pp. 670–675. (In Italian–Summary in English) 1962.
Da Re, *Ann. Chim.* 506–513, (1962). (In Italian).

(List continued on next page.)

*Primary Examiner*—Mukund J. Shah
*Assistant Examiner*—Matthew V. Grumbling
*Attorney, Agent, or Firm*—Darby & Darby

[57] ABSTRACT

The invention relates to benzopyranone and benzothiopyranone compounds, compositions and methods of use which have adrenergic and serotonergic activity.

29 Claims, No Drawings

OTHER PUBLICATIONS

Saari et al., *J. Med. Chem.* 33:97–101, 1990.
Augstein et al, *J. Med. Chem.* 8:356–367, 1965.
*J. Med. Chem.* vol. 22, No. 9, 1979.
Wu et al., *J. Med. Chem.* 35:3519–25, 1992.
P. Valenti et al., *Boll. Chim. Farm.* 114: (1975) II(1).
Lecterc, G. et al., *Arzheim–Forsch Drug. Res.* 35: 1357 (1985) II(9).
Engel, J. et al., *J. Med. Chem.* 33: 2976 (1990) II(10).
CA 63: 11589h (1965).
*J. Med. Chem.* 8: 271 (1965) II(13).
Drawings of the Future 6: 346 (1981) II(14).
CA 84: 59400u (1976).
CA 83: 131584c (1975).
Derwent 91-055570/08 (1991).
Derwent 91-153784/21 (1991).
Derwent 87-104761/15 (1987).
CA 76: 14577z (1972).
CA 100: 103390q (1984).
Vizi, E. S., et al., *Medicinal Research Reviews,* 6: 431 (1986) I(1)a.
CA 101: 7028e (1984).
Derwent 84: 143670/23 (1984).
Derwent 84: 143671/23 (1984).
Derwent 90: 019323/03 (1990).
Derwent 86: 064962/10 (1986).
Derwent 86: 322242/49 (1986).
Atassi, G. et al., *Eur. J. Med. Chem.* 20: 393 (1985) I(10).
C.A. 78, 584606 (1973).
CA 67: 64435m (1967).
Laubie, M. et al., *Arzheim–Forsch* 19: 1820 (1969) I(15)b.
Mull, R. P. et al., *J. Med. Chem.* 8: 332 (1965) I(16).
Bonte, J. P. et al., *Eur. J. Med. Chem.* 25: 361 (1990) I(18).
CAS 104: 109686U (1985).
Bagli, J. F., *J. Med. Chem.* 19: 876 (1976) I(20).
Greival, R. S. et al., *J. Pharmac. Exp. Therap.* 160: 268 (1968) I(21).
Da Re, P. et al., *Eur. J. Med. Chem.* 13: 387 (1978) I(22).
Mielke, D. H. et al., *Curr. Therap. Res.* 15: 324 (1973) I(24).
Silvestrini et al., *Arzheim–Forsch./Drug. Res.* 32: 668–74 (1982) I(25).
CA 59: 2832b (1963).
*J. Med. Chem.* 8: 104 (1965) I(26)b.
CAS 66: 37693s (1967).
C.A. 99: 70608 (1983) I(28).
Derwent A.N. 92-064865/08 (1992).
Morrow, A. L. et al., European Journal of Pharmacology 109, 285–287, (1985).
Hoyer, Daniel et al., European Journal of Pharmacology 118, 13–23, (1985).
Frishman, William H. et al., Medical Clinics of North America, 72., 427–440 (1988).
Cunico et al., *J. Med. Chem.,* 48:2780–2782 (1983).
Garcia-Sainz et al., *Biochemical and Biophysical Research Communications,* 186(2):760–767 (1992).
Hartig et al., *Drug Delivery Res.,* 26(3):215–224 (1992).
Jaen et al., *J. Med. Chem.* 34:248–256 (1991).
Overberger et al., *J.A.C.S.,* 71:2661–2666 (1949).
Perez et al., *Molecular Pharmacology,* 40:876–883 (1991).
Romero et al., *Annual Reports in Medical Chemistry,* 27(3):21–30 (1992).
Wu et al., *J. Med. Chem.* 32:183–192 (1989).
Zifa et al., *Pharmacological Reviews,* 44(3):401–458 (1992).
F. J. Carroll et al., *J. of Med. Chem.,* 1976, vol. 19, No. 9, pp. 1111–1118.

BENZOPYRAN AND BENZOTHIOPYRAN DERIVATIVES

FIELD OF THE INVENTION

This invention relates to benzopyran and benzothiopyran derivatives, to pharmaceutical compositions containing them and to uses for such derivatives and compositions.

BACKGROUND OF THE INVENTION

Flavoxate, which is 8-(2-piperidinoethoxycarbonyl)-3-methyl-4-oxo-2-phenyl-4H-1-benzopyran, and has the formula

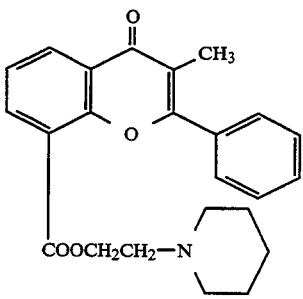

is used as a pharmaceutical agent for urinary tract disturbances as it possesses a smooth muscle relaxing activity attributable to its calcium antagonist activity. This activity is exerted on the bladder dome smooth muscles or can be related to an effect on the micturition center in the central nervous system.

The compounds of the invention, described below, essentially include more complex amino moieties in place of the piperidine group. Further changes include alternatives to the ethoxycarbonyl group which spaces the amino moiety from the benzopyran ring, alternative 2-, 3-, 6- and 7-substitution patterns in the benzopyran ring, replacement of the ring heteroatom by a sulfur atom or by a sulfinyl or sulfonyl group, and/or 2,3-dehydrogenation of the benzopyran ring. These structural variations give the new compounds the ability of interacting with different biological systems, as supported by the affinity of the new compounds for the $\alpha_1$-adrenergic and $5HT_{1A}$-serotoninergic receptors. Flavoxate is practically devoid of affinity for these receptors.

SUMMARY OF THE INVENTION

In one aspect, the invention is directed to compounds of Formula I:

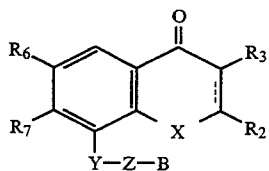

wherein
— represents a single or double bond;
X represents an oxygen or sulfur atom or a sulfinyl or sulfonyl group;
$R_2$ represents a hydrogen atom or an alkyl, alkenyl, carbocyclyl or heterocyclyl group, each of which groups may optionally be substituted by one or more substituents selected from the group consisting of methyl, cyano, hydroxy, methoxy, fluoro, phenyl, phenoxy, trifluoromethyl, nitro, amino, acylamino and benzoyl;
$R_3$ represents a hydrogen atom or a methyl, hydroxymethyl or phenyl group;
$R_6$ represents a hydrogen or halogen atom or a nitro, amino, acylamino, alkylamino, dialkylamino, cyano, hydroxy, alkoxy or alkyl group;
$R_7$ represents a hydrogen atom or a methoxy group;
represents one of the following groups, each of which is depicted with its left hand end being the end which attaches to the heterobicyclic ring and its right hand end being the end which attaches to the group Z:

| | |
|---|---|
| —CO—, | (Y1) |
| —COO—, | (Y2) |
| —CONH—, | (Y3) |
| —CON(CH₃)—, | (Y4) |
| —CON(OH)—, | (Y5) |
| —CH(OH)—, | (Y6) |
| —CH(OAlkyl)—, | (Y7) |
| —CH=CH—, | (Y8) |
| —CH=CH—COO—, | (Y9) |
| —CH=CH—CONH—, | (Y10) |
| —CH=NO—, | (Y11) |
| —CH₂, | (Y12) |
| —CH₂COO—, | (Y13) |
| —CH₂CONH—, | (Y14) |
| —CH₂NH—, | (Y15) |
| —CH₂N(CH₃)—, | (Y16) |
| —CH₂N(COCH₃)—, | (Y17) |
| —CH₂N(CONH₂)—, | (Y18) |
| —CH₂NHCO—, | (Y19) |
| —CH₂N(CH₃)CO—, | (Y20) |
| —CH₂NH—CONH—, | (Y21) |
| —CH₂NHSO₂, | (Y22) |
| —CH₂O—, | (Y23) |
| —CH₂S—, | (Y24) |
| —CH₂SO—, | (Y25) |
| —CH₂SO₂—, | (Y26) |
| —CH₂SO₂NH—, | (Y27) |
| —CH₂SO₂N(CH₃)—, | (Y28) |
| —NH—, | (Y29) |
| —N(CH₃)—, | (Y30) |
| —N(COCH₃)—, | (Y31) |
| —N(CONH₂)—, | (Y32) |

| | |
|---|---|
| —NHCO—, | (Y33) |
| —N(CH₃)CO—, | (Y34) |
| —NH—CONH—, | (Y35) |
| —NHSO₂—, | (Y36) |
| —O—, | (Y37) |
| —S—, | (Y38) |
| —SO—, | (Y39) |
| —SO₂—, | (Y40) |
| —SO₂NH—, | (Y41) |
| —SO₂N(CH₃)—, | (Y42) |
| —CONHO—, | (Y43) |
| —CON(COCH₃)—, | (Y44) |
| —CSNH—, | (Y45) |
| —CSN(CH₃)—, and | (Y46) |

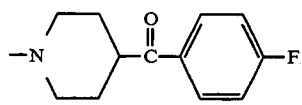  (Y47)

Z represents a linear or branched chain alkylene group having from 1 to 6 carbon atoms and optionally having one hydroxy substituent; and
B represents one of the following groups:

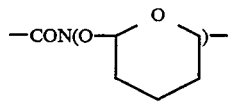  (B1)

wherein R₉ represents a hydrogen or chlorine atom or a methyl, hydroxy, methoxy or ethoxy group,

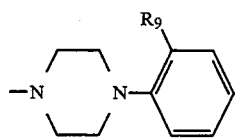  (B2)

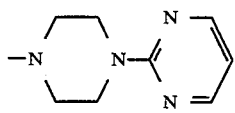  (B3)

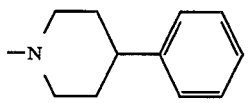  (B4)

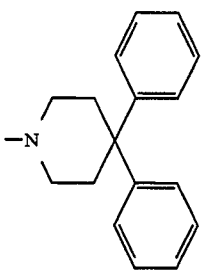  (B5)

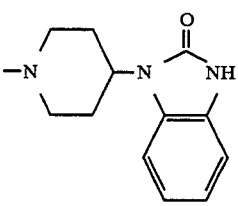  (B6)

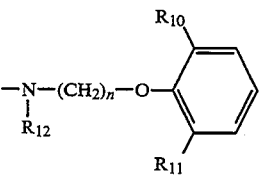  (B7)

wherein each of R₁₀ and R₁₁ independently represents a hydrogen atom or an alkoxy or alkylthio group, R₁₂ represents a hydrogen atom or an alkyl group-and n is 2 or 3,

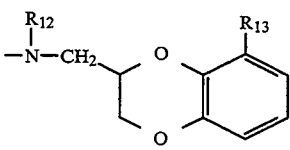  (B8)

wherein R₁₂ has the meanings defined under B7 and R₁₃ represents a hydrogen atom or a methoxy group, and

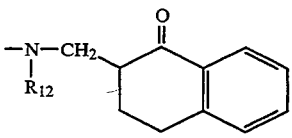  (B9)

wherein R₁₂ has the meanings defined under B7.

The invention also includes the enantiomers, diastereoisomers, N-oxides and pharmaceutically acceptable salts of these compounds.

The invention further provides pharmaceutical compositions comprising a compound of Formula I or an enantiomer, diastereoisomer, N-oxide or pharmaceutically acceptable salt of such a compound, in admixture with a pharmaceutically acceptable diluent or carrier.

In another aspect, the present invention is directed to methods for preventing contractions (including noradrenaline-related contractions) of the urethra and lower urinary tract, selectively preventing said contractions (without substantially affecting blood pressure), lowering blood pressure, and preventing potassium ion induced contractions of the bladder, all by administering one or more selected compounds of the Formula I to a mammal (including a human) in need of such treatment in an amount or amounts effective for the particular use.

In yet another aspect, the invention is directed to methods for blocking $\alpha 1$ and/or $5\text{-HT}_{1A}$ receptors, by delivering to the environment of said receptors, e.g., to the extracellular medium (or by administering to a mammal possessing said receptors) an effective amount of a compound of the invention.

DETAILED DESCRIPTION OF THE INVENTION

The adrenergic antagonistic activity of compounds of the invention renders them useful as agents acting on body tissues particularly rich in $\alpha_1$-adrenergic receptors (such as blood vessels, prostate, urethra, etc.). Accordingly, antiadrenergic compounds within the invention established as such on the basis of their receptor binding profile, can be useful therapeutic agents for the treatment, for example, of hypertension and of micturition problems associated with obstructive disorders of the lower urinary tract, including but not limited to benign prostatic hypertrophy (BPH).

The serotonergic activity of compounds within the present invention renders them useful as agents acting on tissues, particularly in the central nervous system, where $5\text{HT}_{1A}$ receptors are functioning. $5\text{HT}_{1A}$ receptors are believed to regulate the action and release of serotonin as well as the release of other neuromediators and are found both pre- and post-synaptically. The compounds of the invention have biological activity in blocking binding between these receptors and their various specific ligands (e.g. serotonin). Accordingly, the compounds of the invention that interact with the $5\text{HT}_{1A}$ receptor (established as such on the basis of their receptorbinding profile) are useful for the treatment of anxiety disorders and depression.

Surprisingly, compounds within the invention (especially those displaying affinity for both the $\alpha_1$-adrenergic and the $5\text{HT}_{1A}$ serotoninergic receptors) show high selectivity for the mammalian lower urinary tract, i.e. they are substantially more active in antagonizing urethral contractions than in lowering blood pressure. On the contrary, known $\alpha 1$-antagonists, such as prazosin (1-(4-amino-6,7-dimethoxy-2-quinazolinyl)-4-(2-furoyl)-piperazine; GB 1,156,973) do not exhibit such selectivity (and in fact cause hypotension as a most common side-effect) while flavone derivatives structurally similar to flavoxate, such as terflavoxate (1,1-dimethyl-2-(1-piperidinyl)ethyl3-methyl-4-oxo-2-phenyl-4H-1-benzopyran-8-carboxylate hydrochloride; EP 72 620) have no effect on urethral contractions. (Naturally, those compounds of the invention that are not selective for the lower urinary tract are preferred as antihypertensive agents, but even the selective compounds can often be used as antihypertensives because of their low toxicity.)

Compounds within the invention have also shown a good antagonist effect against contractions of rat bladder strip induced by potassium chloride. This effect can be attributed to a calcium antagonistic activity, which renders the new compounds useful as spasmolytics of the lower urinary tract (i.e. useful in the treatment of urinary incontinence, urge syndrome and other similar disorders).

The majority of the compounds of the invention exhibit low toxicity. Thus, they can be used in higher amounts, an advantage that often more than compensates for a relatively lower level of activity that some of these compounds have. Naturally, those compounds exhibiting both high activity and low toxicity are preferred.

The affinity of compounds of the invention for each receptor can be assessed by receptor binding assays, for example as follows:

(1) $\alpha_1$-adrenergic receptor: using the specific ligand $^3\text{H}$-prazosin, according to Morrow, A. L. et al., Eur. J. Pharmacol. 109: 285, 1985;

(2) $5\text{HT}_{1A}$-serotonergic receptors using the specific ligand $^3\text{H}$-8-0-HDPAT according to Hoyer, D. et al., Eur. J. Pharmacol., 118: 13, 1985.

The group

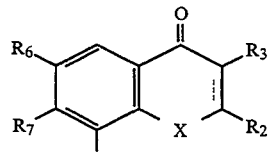

will be abbreviated hereinafter as Fl. The alphanumerics Y1 through Y47 and B1 through B9 will be used as abbreviations for the groups Y and B above to which they respectively apply. For example, Y7, B1, B7 will be used as abbreviations of the specific groups set forth above; if a more specific substitution is intended it will be shown in parentheses after the alphanumeric in the forms Y7 (alkyl), B1($R_9$), B7($R_{10}$, $R_{11}$, $R_{12}$, n), or B8($R_{12}$, $R_{13}$, or B9 ($R_{12}$). Thus, for example, B1(H) represents the 4-phenyl-1-piperazinyl group, while B1(OCH$_3$) represents the 4-(2-methoxyphenyl)-1-piperazinyl group. Finally, B7 (H, OCH$_3$, OH$_3$, 2) represents the N-methyl-2-(2-methoxyphenoxy)ethylamino group.

Without limitation, alkyl groups within the definition of $R_2$ include $C_1$–$C_6$ alkyl; alkenyl groups include $C_2$–$C_3$ alkenyl; carbocyclic groups include cyclohexyl and aryl and heterocyclic groups include rings having one or two heteroatoms and 4 or 5 carbon atoms, such as thienyl, furyl, pyridinyl.

Without limitation, alkyl groups as well as the alkyl moiety of other groups within the definition of $R_6$, $R_{10}$, $R_{11}$ and $R_{12}$ include $C_1$–$C_4$ alkyl.

The preferred values of the substituents in the group Fl are (most preferably simultaneously) as follows:
  ---: a double bond,
  X: an oxygen atom,
  $R_2$: a phenyl group,
  $R_3$: a methyl group,
  $R_6$: a hydrogen atom, and
  $R_7$: a hydrogen atom.

The group having all these preferred substituents, that is the 3-methyl-4-oxo-2-phenyl-4H-1-benzopyran-8-yl group, will be abbreviated hereinafter as Fl'.

Furthermore, the benzopyranyl group having a phenyl substituent in position 3 instead of 2, that is the 4-oxo-3-phenyl-4H-1-benzopyran-8-yl group, will be abbreviated as Fl''.

The preferred (most preferably simultaneously with Fl') groups which Z may represent are trimethylene and tetramethylene. Y preferably represents one of the groups Y2, Y3, Y37, Y40 or Y41. B preferably represents one of the groups B1 or B7, especially the group B1(OCH$_3$).

As a further illustration of the use of the above abbreviations, Fl'-Y3-(CH$_2$)$_3$-B1(OCH$_3$) represents the compound 8-{3-[4-(2-methoxyphenyl)-1-piperazinyl]- propylcarbamoyl}-3-methyl-4-oxo-2-phenyl-4H-1-benzopyran.

SYNTHESIS OF THE COMPOUNDS OF THE INVENTION

The compounds according to the invention may generally be prepared (except when the groups R6 and the substituents at R2 are OH, NH2 or aminoalkyl and Y=Y15 or Y29) as follows:

Path a:

By condensing compounds Fl-Y-Z-L, wherein L represents a halogen atom or a leaving group such as a tosyloxy group, with a compound H-B. The condensation is preferably, but not necessarily, carried out at a temperature within the range of 20°–140° C. in a polar solvent such as dimethylformamide or methanol, usually in the presence of a base such as potassium carbonate. Such condensations are illustrated in Examples 1 to 3, 7 to 9, 11, 13 to 16, 21, 23 to 31, 38 to 42, 46 to 49, 54 to 59, 69 and 73 below. See, also Gibson's chapter in Patai "The Chemistry of the Amino Group", p. 45 et seq. Wiley Interscience, N.Y., 1968.

An alternative method for the preparation of the present compounds is condensation (under the same conditions described in the preceding paragraph) of a compound Fl-Y-H with a compound L-Z-B wherein L is as above defined. This condensation is illustrated in Examples 5, 6, and 66 below. By this route, compounds having Y=Y15 or Y29 can also be prepared (see Gibson's chapter in Patai, supra).

Compounds of formula (I) bearing a NH2 group in R6 or as substituent in R2, may be prepared by reduction of the corresponding compounds (I) wherein R6 or the substituent in R2 are NO2 groups.

Such reduction can be carried out:
- with Ni-Raney catalyst in a protic solvent selected from methanol, ethanol, isopropanol, water and mixtures of them; or
- with SnCl2, H2O, optionally in presence of hydrochloric acid, either in a protic solvent such as methanol, ethanol, isopropanol, water, acetic acid and mixtures of them, or in an aprotic solvent such as ethyl acetate; or
- with Fe and aqueous hydrochloric acid in a protic solvent such as methanol, ethanol, isopropanol, water and mixtures of them.

The temperatures of the above reactions will be chosen in a range between 20° C. and 100° C. (J. March, Advanced Organic Chemistry, III Ed., page 1103, Wiley Interscience, 1985).

Compounds of formula (I) having a NHAlk group as a R6 substituent can be prepared by monoalkylation, starting from the corresponding parent compounds (I) where R6=NH2. For example, this may be done by first reacting the amino compound (I) with an excess of trifluoroacetic anhydride, then reacting the obtained trifluoroacetyl derivative with an alkyl-L reagent and finally unprotecting the thus-obtained trifluoroacetylalkylated derivative by treatment with K2CO3 in methanol or with sodium borohydride in methanol or dimethylsulfoxide.

These reactions are described in Examples 32 and 33, where they were carried out on Y groups.

Compounds bearing a OH group as R6 or as a substituent in R2 may be prepared starting from the corresponding parent compounds (I) alkoxy-substituted at said positions. This can be accomplished by treating the parent compounds for example, with BBr3 in dichloromethane at 0°–40° C. (T. W. Greene "Protective Groups in Organic Synthesis", page 87, Wiley Interscience (1981)) or according to other methods described in the same reference.

Compounds of formula (I) having a saturated 2-3 bond ($\text{---} = |$) can be alternatively obtained:
- by selective hydrogenation of the corresponding compounds of formula (I) having a 2-3 double bond ($\text{---} = |$);
- by conversion of the appropriate intermediates with a saturated 2-3 bond, which in turn can be obtained according to Scheme 5 in the Starting Materials section.

These conversions are performed according to the methods described for compounds of formula (I) having a 2-3 double bond, in particular when a nitro group is already present in the molecule.

The selective hydrogenations can be carried out using alternatively:
- hydrogen in presence of a metal or metal oxide catalyst (e.g.: palladium on charcoal, or platinum dioxide) in a protic solvent at 20°–120° C. (E. H. Rodd, Chemistry of Carbon Compounds, Vol. IVB, page 903, Elsevier, 1959);
- di-(isobutyl)aluminum hydride in an aprotic solvent (e.g.: tetrahydrofuran and/or methylene chloride) at $-70°/0°$ C. (H. Sarges et al., *J. Med. Chem.* 33, 1859 (1990).

In some cases, compounds of the Formula I may be prepared by conversion of other (parent) compounds of the invention. Such conversions include:

Path b:

Fl-CO-Z-B to Fl-CH(OH)-Z-B by reduction as illustrated in Examples 17 to 20 below, Path c:

Fl-CH(OH)-Z-B to Fl-(CHOAlkyl)-Z-B by etherification as illustrated in Example 22, Path d:

Fl-(CH2)n-NH-Z-B→Fl-(CH2)n-NCH3-Z-B where n=0, 1, by methylation as illustrated in Example 35;

Path e:

Fl-(CH2)n-NH-Z-B→Fl-(CH2)n-N(COCH3)-Z-B where n=0, 1, by N-acetylation as illustrated in Example 36;

Path f:

Fl-(CH2)n-NH-Z-B→Fl-(CH2)n-N(CONH2)-Z-B where n=0, 1, by reaction with potassium isocyanate as illustrated in Example 50;

Path g:

Fl-CH(OH)-Z-B→Fl-CO-Z-B by oxidation, as illustrated in Example 51;

Path h:

Fl-Y-Z-B→Fl-Y-Z-B(N-monoxide) by oxidation as illustrated in Example 43;

Path i:

H2N-Fl-Y-Z-B→CH3CONH-Fl-Y-Z-B (wherein H2N-Fl represents a Fl group bearing an amino group as the R6 group or as the substituent in R2) using the N-acylation method described in Example 36.

Path j:

Fl(R6=NH2)-Y-Z-B→Fl(R6=NAlk2)-Y-Z-B by exhaustive N-alkylation using the method described in Example 35.

Path k:

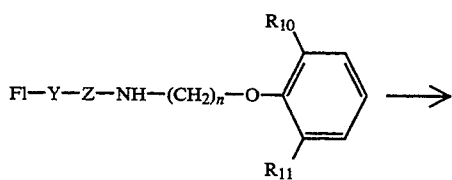

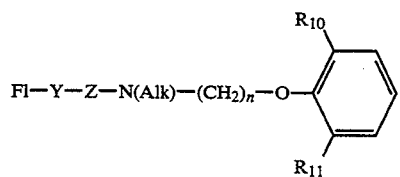

or

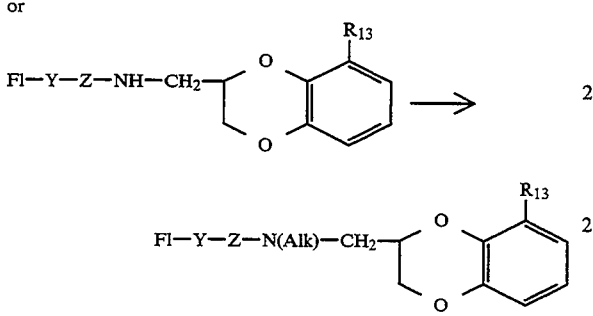

or

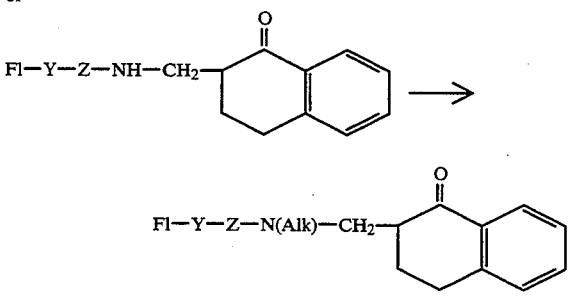

by N-alkylation using the procedure described in Examples 35 and 62.

Some compounds may be prepared by addition reactions. For example those in which Z contains a hydroxy substituent may be prepared by addition across an epoxy group Path l:

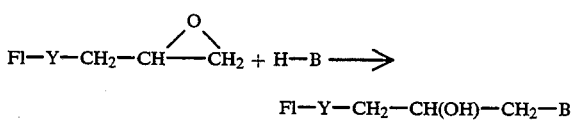

Fl—Y—CH$_2$—CH(OH)—CH$_2$—B as illustrated in Example 45.

Addition across a double bond is also possible, e.g.:

Path m:

Fl-Y-CH=CH$_2$+H-B→Fl-Y-CH$_2$-CH$_2$-B as illustrated in Examples 37 and 63.

Other synthetic schemes include the formation of Y, Z or B during the reaction, for example Path n:

Fl-(X)-(Q)-Cl+A-HN-Z-B→Fl-(X)-(Q)-N(A)-Z-B (wherein X=bond, CH$_2$ or CH=CH, Q=CO or SO$_2$, and A=H, CH$_3$ or OP$_r$ wherein P$_r$ is a protective group) as illustrated in Example 12 (particularly preferred) and in Examples 60, 61, 64, 67, 68 and 72.

The same compounds may also be prepared by other routes including:

* Fl-(X)-COOH+A-NH-Z-B in presence of a coupling agent (e.g. dicyclohexylcarbodiimide or N,N'-carbonyldiimidazole) optionally in the presence of a promoting agent (e.g. 4-dimethylaminopyridine or N-hydroxybenzotriazole) in an aprotic or a chlorinated solvent (e.g. dimethylformamide, chloroform) at −10°/140° C. (Albertson, *Org. React.* 12, 205–218 (1962); Doherty et al., *J. Med. Chem.* 35: 9 (1992); Staab et al., *Newer Methods Prep. Org. Chem.*, 5: 61 (1968));

* Fl-(X)-COOH+A-NH-Z-B without a solvent at 150°–220° C. (Mitchell et al., *J. Am. Chem. Soc.* 53: 1879 (1931) or in high-boiling ethereal solvents (e.g. diglyme);

* Fl-(X)-COO-Alk+A-NH-Z-B optionally in the presence of a coupling agent (e.g.: trimethylaluminum) in an aprotic and/or a chlorinated solvent (e.g. hexane, dichloromethane) at −10°/80° C., or without solvents at 80°–180° C., (S. M. Weinreb et al., *Tetrahedron*, 1977, 4171); M. F. Lipton et al., *Org. Synth.* 59: 49 (1979));

* Fl-(X)-COOH+alkyl chloroformate in presence of a tertiary amine (e.g. triethylamine) followed by addition of A-NH-Z-B at 0°–80° C.; optionally a promoting agent (e.g.: 1-hydroxypiperidine) may be added before the amine addition (Albertson, *Org. React.* 12: 157 (1962).

Path o:

Fl-COCl+H$_2$NO-Z-B→Fl-Y43-Z-B.

Path p:

Fl-COCl+HO-Z-B→Fl-Y2-Z-B as illustrated in Example 10.

Path q:

FlCHO+H$_2$NO-Z-B→Fl-Y11-Z-B, as illustrated in Example 70.

Path r:

Fl-CHO+A-HN-Z-B→Fl-CS-N(A)-Z-B (where A=H; CH$_3$) in presence of sulfur in an aprotic solvent (e.g. dimethylformamide or pyridine at 60°–120° C. (M. Carmack et al., *Org. Reaction* 3: 83 (1947) and R. Benassi et al., *Org. Magn. Res.* 15, 25 (1981)).

Path s:

Fl-NH$_2$+HCO-Z-B→Fl-Y29-Z-B as illustrated in Example 34,

Path t:

Fl-Y-CH$_3$+HO-CH$_2$-B→Fl-Y-CH$_2$-CH$_2$-B as illustrated in Example 4,

Path u:

Fl-CH=CH-CONH$_2$+HOCH$_2$-B→Fl-Y10-CH$_2$-B.

Path v:

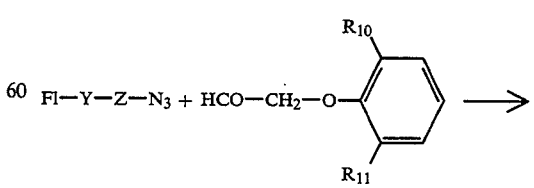

Fl—Y—Z—B7(R$_{10}$, R$_{11}$, H, 2)

under reducing conditions as illustrated in Example 44.

Path w:

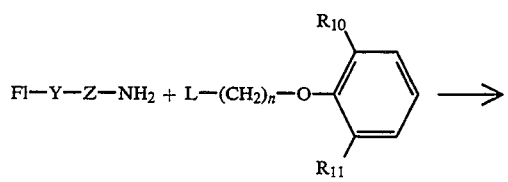

Fl—Y—Z—B7 or

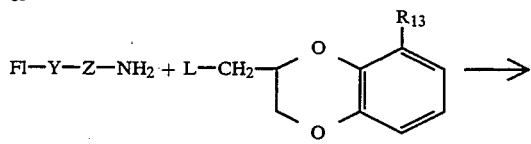

Fl—Y—Z—B8, see Ex. 52.
Path x:

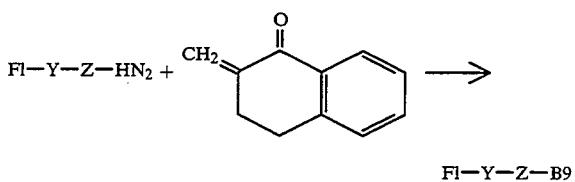

Fl—Y—Z—B9 as illustrated in Example 65.
Path y:

Fl-Y-Z-CHO+HB→Fl-Y-Z-B as illustrated in Example 53.

Persons skilled in the art are aware that all the above synthetic paths b) to y) might be simplified provided that the reacting intermediate does not bear further groups sensitive to the same reactants (for example: CO, $NH_2$, NHAlk or OH groups).

Compounds of formula (I) bearing the above cited reactive groups can be prepared through paths b) to y) on condition that the reactive groups present in the starting materials are converted into non-reactive groups before reacting and then deprotected at the end of the reaction as illustrated in Example 71. Several examples of protection and deprotection for various reactive groups can be found in: T. W. Greene, "Protective Groups in Organic Synthesis"—Wiley Interscience (1981).

Alternatively, unreactive groups (e.g. $NO_2$) can be left unconverted during the first reaction and then converted to reactive ones (e.g.: $NH_2$) as a final step of the pathway. See for example path a).

Which synthetic technique will be preferred depends on the compound desired to be synthesized, but path n) is generally preferred for the compounds that can be made by it. Additional synthetic methods will be apparent to those skilled in the art.

Starting Materials

Intermediates, such as the compounds Fl-Y-Z-L and Fl-Y-H used in the preparation of compounds of the invention may themselves be prepared from simple compounds such as Fl-COOH, Fl-CHO, Fl-COCl, Fl-$NH_2$ Fl-OH and FlCH$_2$CH=CH$_2$ by transformations known to those skilled in the art. Several such transformations are described in detail in the Examples.

When X is oxygen, many of the aforesaid simple compounds are commercially available or their synthesis has been published in the literature. Those which are not available may be synthesized by cyclization according to the following Reaction Scheme 1 wherein the steps have the various meanings described below:

SCHEME 1

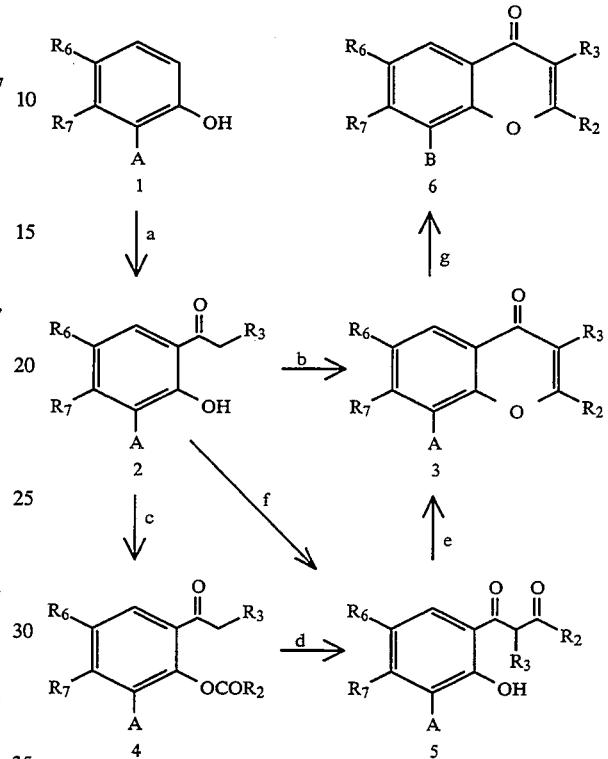

A = $CO_2CH_3$, $CO_2C_2H_5$, $NO_2$
B = $CO_2H$, $NH_2$

Step 1a:

Procedure without isolation of the intermediate phenyl ester: $R_3CH_2COCl$ or $(R_3CH_2CO)_2O$ and a Lewis acid (e.g. $AlCl_3$ or $ZnCl_2$), without solvent or in aprotic solvent (e.g. nitrobenzene or chlorinated solvent) at 20°–180° C.;

procedure with isolation of the intermediate phenyl ester: $R_3CH_2COCl$ or $(R_3CH_2CO)_2O$ heated with the starting material or other esterification methods, such as the Schotten-Bauman procedure. The isolated ester is then heated in nitrobenzene or other non protic solvent (e.g. chlorinated solvent), or without any solvent, at 20°–180° C., in the presence of a Lewis acid (e.g. $AlCl_3$, or $ZnCl_2$). (A. M. Blatt, Org. React. 1: 342 (1942)).

Step 1b:

$R_2COCl$ and $R_2COONa$ alone or in high-boiling non-protic solvent (e.g. o-dichlorobenzene) at 150°–220° C.;

$R_2C(OAlk)_3$ in the presence of $HClO_4$ at 20°–40° C. or in pyridine in the presence of piperidine at 60°–80° C.

Step 1c:

$R_2COCl$ in pyridine at 20°–100° C. or in non-protic solvent at 0°–80° C., optionally in the presence of a base.

Step 1d:

Potassium carbonate in acetone or methyl ethyl ketone at 20°–80° C.;

Sodium hydride in dimethylsulfoxide or tetrahydrofuran at 0°–40° C.;

Potassium hydroxide in pyridine at 40°–80° C.

Step 1e:

Hydrochloric acid or sulfuric acid in water or other protic solvents (e.g., ethanol, acetic acid) at 0°–100° C.;

Trifluoracetic acid in dichloromethane at 20°–40° C.;

p-toluenesulfonic acid in benzene or toluene at reflux.

Step 1f:

$R_2COCl$ and potassium carbonate or potassium hydroxide in water and a phase transfer catalyst in benzene or toluene at reflux;

$R_2COOAlk$ and lithium bis(trimethylsilyl)amide or lithium diisopropylamide in tetrahydrofuran at −78°/0° C.

Step 1g:

When A is a $COOCH_3$ or $COOC_2H_5$ group:

Sodium hydroxide in aqueous ethanol at 40°–75° C.;

Lithium hydroxide in aqueous dimethylformamide at 40°–100° C. When A is $NO_2$:

Reduction with Ni-Raney catalyst in a protic solvent (e.g. i-propanol) or a mixture of protic solvents;

Reduction with $SnCl_2$ in the presence of aqueous hydrochloric acid in a protic solvent (e.g. acetic acid);

Reduction in presence of Fe and aqueous hydrochloric acid in protic solvent.

The temperature range for the above reactions is 20° C. to 100° C.

When X represents a sulfur atom or a sulfinyl or a sulfonyl group, the simple starting materials may be prepared according to the following Reaction Scheme 2 wherein the steps have the following alternative meanings:

SCHEME 2

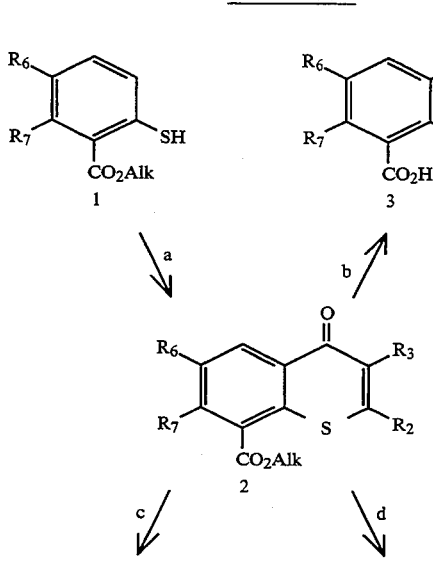

-continued
SCHEME 2

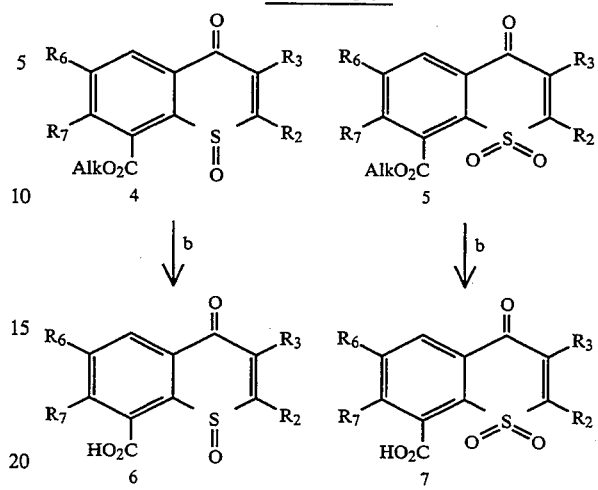

Step 2a:

$R_2COCH(R_3)CN$ or $R_2COCH(R_3)COOAlk$ in polyphosphoric acid at 50°–120° C.;

$R_2C\equiv C\text{-}COOAlk$ and $Al_2O_3$ in aprotic solvents (e.g. diethyl ether) at 0°–40° C.;

$R_2C\equiv C\text{-}COOAlk$ and a base in aprotic solvents (e.g. tetrahydrofuran or dimethylformamide) at 20°–140° C.

The last two options are both followed by treatment with polyphosphoric acid at 50°–120° C.

Step 2b:

Sodium hydroxide in aqueous ethanol at 40°–75° C.

Lithium hydroxide in aqueous dimethylformamide at 40°–100° C.

Step 2c:

Stoichiometric 30% hydrogen peroxide in acetic acid, at 25°–60° C.;

m-chloroperbenzoic acid in chloroform at 0°–30° C.;

Step 2d:

30% hydrogen peroxide in acetic acid at 50°–80° C.

The starting ortho-mercaptobenzoates are commercially available or can be prepared by known methods: for example by transformation of the corresponding orthoalkoxycarbonylbenzenediazonium salts upon treatment with potassium ethylxanthate (M. S. Cohen et al., J. Org. Chem. 18: 1394 (1953)).

Simple starting materials having $R_7=OCH_3$ may be prepared according to Reaction Scheme 3 wherein the step 3a is:

Step 3a:

Formaldehyde and gaseous HCl in acetic acid containing aqueous HCl (d=1,18) at 50°–100° C. (P. Da Re et al., Ann. Chim., 46:904 (1956)). This method can be used when $R_3$ is different from H or from a hydroxymethyl group.

SCHEME 3

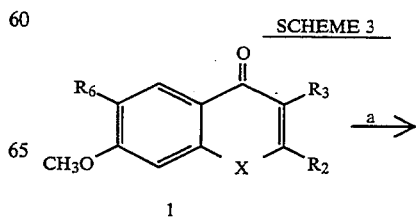

-continued
SCHEME 3

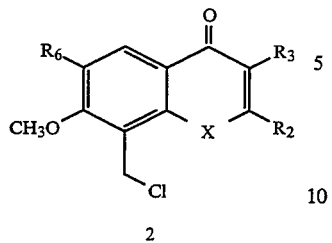

Intermediates (1) can be prepared according to Schemes 1 and 2 starting from the appropriate phenols or thiophenols (not substituted at position 2 or 6 with COOAlk or $NO_2$); then, the resulting Intermediates (2) can be converted using known methods to starting materials suitable for obtaining the desired compounds of the invention.

The preparation of simple starting materials having $R_3$=hydroxymethyl can be carried out by reacting either Intermediates (3) of Scheme 1 or Intermediates (2), (4) or (5) of Scheme 2 having $R_3$=H, $CH_3$ according to the Reaction Scheme 4, wherein the steps 4a–4d, have the following meanings:

Formaldehyde and hydrogen chloride in water, ethanol or acetic acid at 50°–100° C.;

Chloromethyl methyl ether and fuming sulfuric acid at 50°–70° C. (H. Nakarumo et al., *Bull. Chem. Soc. Jap.*, 57: 2323 (1984)); $R_3$=$CH_3$:

N-bromosuccinimide in presence of benzoyl peroxide or 2,2'-azobisisobutyronitrile in carbon tetrachloride at 50°–80° C.;

Step 4b:

Sodium acetate in aprotic solvents (e.g. acetone, dimethylformamide) at 40°–100° C.

Step 4c:

Stoichiometric NaOH in aqueous ethanol at 25°–50° C.

The simple Intermediates (4) obtained in this way can be reacted as such or, alternatively, derivatized at the hydroxymethyl group with known reagents and methods, so that said group does not interfere in the further reaction steps necessary to prepare those compounds of formula (I) which bear a protected hydroxymethyl group such as $R_3$.

The protected final compounds are finally converted by deprotecting methods to compounds of formula (I) having $R_3$=hydroxymethyl group.

The synthesis of the simple 2,3-dihydro intermediates

SCHEME 4

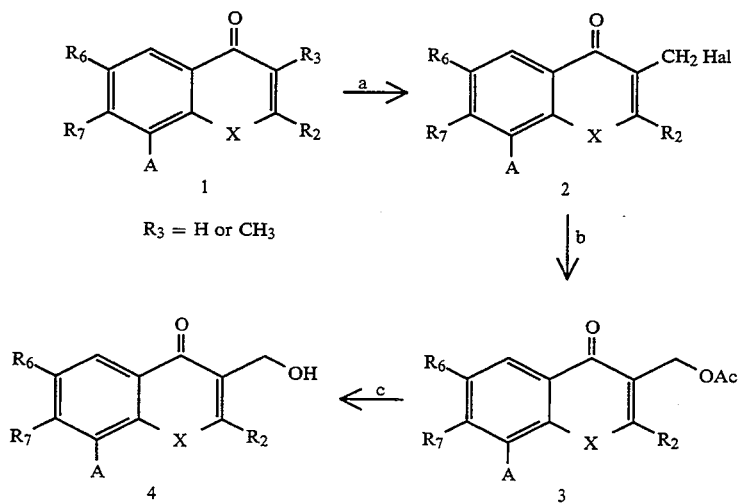

Step 4a:
$R_3$=H:

($\equiv = |$), provided that other reactive groups possibly present (e.g. $NH_2$, OH) have been previously protected as described before, can be pursued using a method of the Reaction Scheme 5, wherein the steps 5a–5i have the following meanings:

SCHEME 5

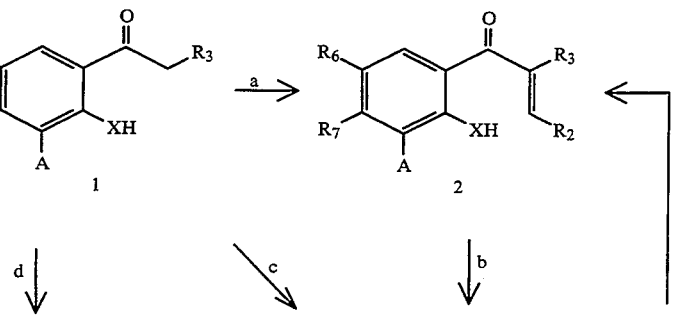

SCHEME 5

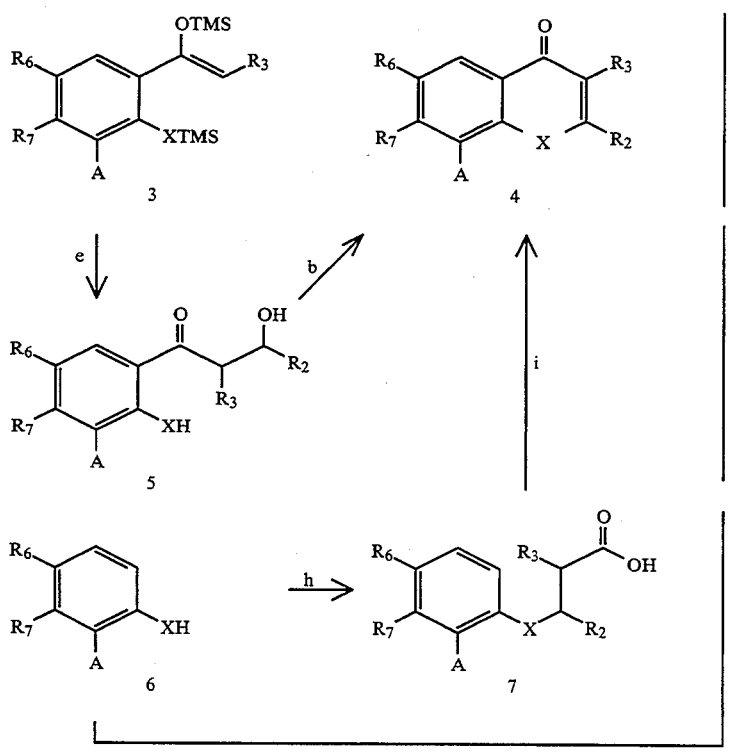

Step 5a:
R$_2$—CHO, aqueous sodium hydroxide in ethanol or other protic solvent;

R$_2$—CHO, sodium hydride or potassium tert-butoxide in tetrahydrofuran (or other dipolar aprotic solvent) at 0°-150° C.;

Step 5b:
Mineral acid (e.g. hydrochloric acid or sulfuric acid) in water or other protic solvents (e.g. ethanol, acetic acid) at 0°-100° C.;

Step 5c:
R$_2$—CHO, 0.1-1N aqueous sodium hydroxide or other suitable base in a protic solvent;

R$_2$—CHO, pyrrolidine in a protic (e.g. methanol) or polar aprotic solvent at 0°-100° C. (H. J. Kabbe, Synthesis, 1978, p.886);

Step 5d:
Lithium diisopropylamide in tetrahydrofuran at 0°-20° C.; then trimethylsilylchloride and an organic base (e.g. triethylamine) (S. E. Kelly et al., *J. Org. Chem.* 56: 1325 (1991));

Step 5e:
R$_2$—CHO in a chlorinated solvent (e.g. CH$_2$Cl$_2$) at −78° C. then TiCl$_4$ (or other Lewis acid) (S. E. Kelly, et al., *J. Org. Chem.*, 56:1325 (1991));

Step 5f:
Lithium diisopropylamide in tethrahydrofuran at −78° C. then R$_2$—CHO (A. Banerij et al., *Tetrahedron Letter*, 1979, 3685);

Step 5g:
R$_2$—CH=CR$_3$COCl, a Lewis acid (e.g. AlCl$_3$) in a suitable solvent (e.g. nitrobenzene) or without solvent at 20°-180° C.;

Step 5h:
R$_2$—CH=CR$_3$COOAlk, triethylbenzylammonium hydroxide in an aprotic solvent (e.g.: benzene) or without solvent at 50°-150° C.; then aqueous NaOH in methanol at 20°-50° C. or lithium hydroxide in aqueous dimethylformamide. (In this case compounds having A=COOCH$_3$ or COOC$_2$H$_5$ are also hydrolyzed to compounds having A=COOH);

Step 5i:
Concentrated sulfuric acid or phosphorus pentoxide or polyphosphoric acid or a Lewis acid in nitrobenzene or toluene or without solvent at 0°-180° C. (Also in this case hydrolysis of A=COOAlk to A=COOH occurs).

The Intermediates (4) thus obtained can be converted to the corresponding derivatives having A=COOH or NH$_2$ according to the method of Scheme 1, step 1g).

DETAILED SYNTHESIS OF INTERMEDIATES 8-(3-bromopropoxycarbonyl)-3-methyl-4-oxo-2-phenyl-4H-1-benzopyran (Intermediate I)

30 g of 1,3-dibromopropane was added dropwise at ambient temperature to a suspension of 30 g of sodium 3-methyl-4-oxo-2-phenyl-4H-1-benzopyran-8-carboxylate in 150 ml of dimethylformamide and 35 ml of water. The reaction mixture was stirred at ambient temperature for 5 days. 100 ml of water was added and stirring was continued for a further 15 minutes. The precipitate was filtered off by suction, washed with water and purified by flash chromatography on silica gel, eluting with chloroform:ethyl acetate 95:5. The collected fractions were evaporated to dryness in vacuo and the residue was recrystallized from ethanol to give 27.7 g of the title compound, m.p. 114°-115° C.

The benzopyran carboxylate salt used in the foregoing synthesis was prepared by dissolving the corresponding acid (104 g) in hot methanol (560 ml) and adding an aqueous solution (280 ml) of sodium hydrogen carbonate (31 g). The solution was added with acetone (850 ml) yielding the desired salt, collected by suction (62 g, m.p.>280° C.). The corresponding acid was prepared as per Da Re, P. et al., *J. Med. Pharm. Chem.* 2: 263, 1960.

8-hydroxymethyl-3-methyl-4-oxo-2-phenyl-4H-1-benzopyran (Intermediate II)

467 ml of a 1.48N solution of sodium borohydride in anhydrous dimethyl formamide was added over a period of 30 minutes, under stirring at ambient temperature, to a solution of 100 g of 3-methyl-4-oxo-2-phenyl-4H-1-benzopyran-8-carbonyl chloride (prepared as described in Da Re, supra) in 1 liter of anhydrous dimethylformamide. The reaction mixture was stirred for 2.5 hours at ambient temperature. 88 ml of 2N hydrochloric acid was added while maintaining the temperature at 0°-5° C. 102 ml of 12.7N sodium hydroxide solution was then added. The mixture was poured into 6 liters of water, stirred for 3 hours, and filtered on a Buchner funnel. The filter cake was washed with 4N sodium hydroxide solution and then with water. The resultant white solid was crystallized from methanol to give 50 g of the title compound, m.p. 145°-147° C.

E-8-(2-carboxyvinyl)-3-methyl-4-oxo-2-phenyl-4H-1-benzopyran (Intermediate III)

A mixture of 7.92 g of 8-formyl-3-methyl-4-oxo-2-phenyl-4H-1-benzopyran (prepared as described in Uneyama, K. et al., *Bull. Chem. Soc. Jap.* 58: 2361, 1985) 3.75 g of malonic acid and 0.46 ml of piperidine in 15 ml of anhydrous pyridine was stirred at 100° C. for 3 hours. After cooling to 20°-25° C. the reaction mixture was poured into a mixture of 90 g of crushed ice and 33 ml of hydrochloric acid (d=1.18). The resultant precipitate was collected by suction filtration, washed with water and crystallized twice from 95% ethanol to give 5.5 g of the title compound, m.p. 226°-229° C.

E-8-(2-chlorocarbonylvinyl)-3-methyl-4-oxo-2-phenyl-4H-1-benzopyran (Intermediate IV)

A solution of 9.2 g of Intermediate III and 7.8 g of thionyl chloride in 75 ml of toluene was refluxed for 3 hours. After cooling to 20°-25° C. the resultant crystal was collected by suction filtration, washed with acetone and dried in vacuo to give 6.8 g of the title compound, m.p. (190) 196°-198° C. after recrystallization from toluene.

8-acetyl-3-methyl-4-oxo-2-phenyl-4H-1-benzopyran (Intermediate V)

1.17 g of magnesium turnings, 7.4 ml of anhydrous ethanol and 0.2 ml of anhydrous carbon tetrachloride were placed in a round bottomed flask under a stream of nitrogen. When the temperature began to rise, 7.5 ml of anhydrous chlorobenzene was added, followed by the slow dropping (25 minutes) of a solution of 5.28 ml of anhydrous diethylmalonate and 3.5 ml of anhydrous chlorobenzene in 16 ml of anhydrous ethanol. The reaction flask was heated to 75° C. for two hours, cooled to 25° C. and a solution of 8.8 g of 3-methyl-4-oxo-2-phenyl-4H-1-benzopyran-8-carbonyl chloride in 88 ml of anhydrous chlorobenzene was slowly added, without exceeding 35° C. The reaction mixture was further stirred for two hours at 35° C. and then cooled to 0° C. 13 ml of water and 1.9 ml of sulfuric acid (d=1.84) were added. The solution obtained was decanted from the insoluble inorganic matter and stripped in vacuo.

The crude acylmalonate obtained was refluxed for six hours with 10.4 ml of acetic acid, 7 ml of water and 1.3 ml of sulfuric acid (d=1.84). After cooling, the solution was poured into iced water and the precipitate was collected by suction filtration and washed with aqueous sodium carbonate. Crystallization from 90% ethanol gave 6.5 g of the title compound, m.p. 159°-161° C.

8-bromoacetyl-3-methyl-4-oxo-2-phenyl-4H-1-benzopyran (Intermediate VI)

A solution of 11.2 g of bromine in 250 ml of chloroform was added, over a period of two hours at 20°-25° C., to a solution of 19.5 g of the Intermediate V in 700 ml of chloroform. After stirring for 1 hour at 20°-25° C., the solution was washed with 400 ml of 2N aqueous sodium hydroxide solution and then repeatedly with water, dried with anhydrous sodium sulfate and stripped in vacuo. The crude product was treated with diethyl ether, collected by suction filtration and crystallized from acetone, yielding 16 g of the title compound, m.p 134°-135° C.

8-(2-hydroxyethylcarbamoyl)-3-methyl-4-oxo-2-phenyl-4H-1-benzopyran (Intermediate VII)

The title compound was prepared in the same manner as Intermediate XXXVI, but using 2-aminoethanol instead of 3-aminopropanol. m.p. 206°-208° C.

3-methyl-4-oxo-2-phenyl-4H-1-benzopyran-8-sulfonyl chloride (Intermediate VIII)

A solution of 4.55 g of sodium nitrite in 12 ml of water was added dropwise to a stirred mixture of 15.1 g of 8-amino-3-methyl-4-oxo-2-phenyl-4H-1-benzopyran (prepared as described in Da Re, P. et al., *Il. Farmaco* (Ed. Sci.) 11: 670, 1956) in 150 ml of hydrochloric acid (d=1.18) at −5° C. Stirring was continued at 0° C. for 30 minutes. The solution was poured, over a period of 10 minutes and at −5° to 0° C., into 120 ml of a 30% by weight solution of sulfur dioxide in acetic acid containing 1.53 g of cupric chloride dihydrate and 13 ml of water. After 1 hour at 0° C. and 1 hour at 20°-25° C., 300 ml of iced water was added to the mixture. A precipitate formed and was collected by suction filtration, washed with water and dried in a desiccator over sodium hydroxide until of constant weight to give 18 g of crude title product, m.p. 165°-170° C., for use without further purification.

8-(3-chloropropoxy)-3-methyl-4-oxo-2-phenyl-4H-1-benzopyran (Intermediate IX)

This compound was prepared in the same manner as Intermediate XI, but using 1-bromo-3-chloropropane instead of 1-bromo-2-chloromethane (m.p. 98°-102° C.) after washing with petroleum ether:diethyl ether 7:3.

8-acrylamido-3-methyl-4-oxo-2-phenyl-4H-1-benzopyran (Intermediate X)

A solution of 1.75 ml of acryloyl chloride in 15 ml of anhydrous tetrahydrofuran was added dropwise at −10° C. to a stirred mixture of 5 g of 8-amino-3-methyl-4-oxo-2-phenyl-4H-1-benzopyran and 3 ml of triethylamine in 60 ml of anhydrous tetrahydrofuran. After stirring at 0° C. for 1 hour and at ambient temperature for 1 hour, the reaction mixture was poured into water and filtered under suction. The filter cake was washed with water. Desiccation gave 5.5 g of the title compound, m.p. 229°-230° C.

8-(2-chloroethoxy)-3-methyl-4-oxo-2-phenyl-4H-1-benzopyran (Intermediate XI)

A mixture of 7.52 g of 8-hydroxy-3-methyl-4-oxo-2-phenyl-4H-1-benzopyran (prepared as described in Da Re, P. et al., *Ann. Chim.*, 1962, p.506 et seq.), 6.22 g of anhydrous potassium carbonate and 25.5 ml of 1-bromo-2-chloromethane in 70 ml of dimethylformamide was stirred at 60° C. for 25 hours. The mixture was cooled to 20°-25° C. and poured into 600 ml of water. The organic solution, obtained by extraction with dichloromethane, was washed with aqueous sodium chloride solution and dried on anhydrous sodium sulfate. The solvents and excess 1-bromo-2-chloromethane were evaporated off in vacuo to yield 8.8 g of the title compound, m.p. 141°–142° C. after crystallization from chloroform:hexane.

8-(2-azidoethoxy)-3-methyl-4-oxo-2-phenyl-4H-1-benzopyran (Intermediate XII)

A mixture of 15.2 g of Intermediate XI and 6.24 g of sodium azide in 150 ml of anhydrous dimethylformamide was stirred at 70°–75° C. for 12 hours. After cooling to 20°–25° C., the reaction mixture was poured into 1.5 liters of water and extracted with dichloromethane. The organic solution was washed with aqueous sodium chloride solution and dried on anhydrous sodium sulfate. The solvents were evaporated off in vacuo. The residue was taken up in water, collected by suction filtration and dried to give 14 g of the title compound, m.p. 119°–120° C.

8-[N-(2-hydroxyethyl)-N-methyl-carbamoyl]-3-methyl-4-oxo-2-phenyl-4H-1-benzopyran (Intermediate XIII)

A solution of 1.6 ml of 2-methylamino-ethanol in 10 ml of water was added dropwise over a period of 5 minutes to a suspension of 6 g of 3-methyl-4-oxo-2-phenyl-4H-1-benzopyran-8-carbonyl chloride and 1.52 g of potassium carbonate in 60 ml of acetone. After stirring for 2.5 hours at 20°–25° C., the solvent was removed in vacuo and the residue was taken up in 150 ml of acetone. The mixture was refluxed for 15 minutes, and was then filtered. The solvent was evaporated from the filtrate and the residue was dissolved in 20 ml of dimethylformamide, treated with 14 ml of 1.4% sodium carbonate solution, stirred for 30 minutes at 20°–25° C. and diluted by addition of 150 ml of water. The mixture was extracted with chloroform and the organic layer was washed with 0.5N hydrochloric acid and then with water. The solution was dried over anhydrous sodium sulfate and the chloroform was evaporated off. The resulting oil was taken up in 200 ml of diethyl ether and stirred for 2 hours at 20°–25° C. The solid was collected by filtration and crystallized from ethyl acetate to give 4.97 g of the title compound, m.p. 128°–30° C.

8-(2-chloroethylcarbamoyl)-3-methyl-4-oxo-2-phenyl-4H-1-benzopyran (Intermediate XIV)

The title compound was prepared in the same manner as Intermediate XXXVII, but using Intermediate VII in place of Intermediate XXXVI and carrying out the reaction at ambient temperature, m.p. 181°–182° C. (ethyl acetate).

8-(N-methyl-2-chloro-ethylcarbamoyl)-3-methyl-4-oxo-2-phenyl-4H-1-benzopyran (Intermediate XV)

A solution of 1.1 ml of thionyl chloride in 2 ml of dichloromethane was added to a solution of 3.37 g of Intermediate XIII in 20 ml of dichloromethane, and the mixture was stirred for 4 hours at ambient temperature. Removal of the solvent gave an oil which was taken up in diethyl ether. The title compound precipitated as a white solid which was filtered off for use without further purification. m.p. (118) 126°–128° C. (diethyl ether).

8-(4-bromobutoxy)-3-methyl-4-oxo-2-phenyl-4H-1-benzopyran (Intermediate XVI)

A mixture of 5 g of 8-hydroxy-3-methyl-4-oxo-2-phenyl-4H-1-benzopyran, 4.2 g of anhydrous potassium carbonate and 43.6 g of 1,4-dibromobutane in 45 ml of dimethylformamide was stirred at 75° C. for 2 hours. The mixture was cooled to 20°–25° C., poured into 100 ml of water and extracted with dichloromethane. The organic solution was washed with aqueous sodium chloride solution and dried on anhydrous sodium sulfate. The solvents and excess 1,4-dibromobutane were evaporated off in vacuo. The residue was rinsed with 55 ml of petroleum ether:diethyl ether 7:4 and collected by suction filtration to yield 5.6 g of the title compound, m.p. 91°–92° C.

8-(5-bromopentyloxy)-3-methyl-4-oxo-2-phenyl-4H-1-benzopyran (Intermediate XVII)

This compound was prepared by the method described for the preparation of Intermediate XVI, but using 1,5-dibromopentane in place of 1,4-dibromobutane and purifying the crude product by column chromatography on silica gel (elution with dichloromethane:ethyl acetate 99:1) m.p. 75°–76° C., after rinsing with petroleum ether:diethyl ether 30:4.

8-(2-chloroethoxymethyl)-3-methyl-4-oxo-2-phenyl-4H-1-benzopyran (Intermediate XVIII)

6 ml of thionyl chloride in 18 ml of chloroform was added at 0° C. to a stirred solution of 23 g of Intermediate XXII and 11 ml of triethylamine in 185 ml of chloroform. The reaction mixture was warmed to 70° C. and stirred for 2 hours. After cooling to ambient temperature, it was poured into water. The organic layer was separated, washed with sodium chloride solution, dried on anhydrous sodium sulfate and evaporated to dryness in vacuo. Yield 24 g of the title compound. A sample crystallized from ethanol had a melting point of 102°–103° C.

8-chloromethyl-3-methyl-4-oxo-2-phenyl-4H-1-benzopyran (Intermediate XIX)

53.4 g of Intermediate II and 38.8 ml of anhydrous triethylamine were dissolved in 440 ml of chloroform. Into this solution, maintained at −10° to −20C., there was dropped a solution of 19.8 ml of thionyl chloride in 80 ml of anhydrous chloroform. The reaction mixture was stirred at room temperature for 4 hours, and then diluted with 400 ml of water. The aqueous phase was extracted with chloroform, and the extracts were added to the chloroform phase. The chloroform solution was washed with brine, dried on anhydrous sodium sulfate and evaporated to dryness in vacuo. Yield: 56 g of the title compound, which on recrystallization from ethanol was shown to have a melting point of 112°–113° C.

8-methylaminomethyl-3-methyl-4-oxo-2-phenyl-4H-1-benzopyran (Intermediate XX)

A solution of 15.1 g of anhydrous zinc chloride and 14.5 g of sodium cyanoborohydride in 400 ml of anhydrous methanol was added dropwise at 0° C. into a stirred mixture of 58.8 g of 8-formyl-3-methyl-4-oxo-2-phenyl-4H-1-benzopyran, 60.7 g of methylamine hydrochloride and 125 ml of triethylamine in 600 ml of anhydrous methanol. After stirring for 5 hours at 20°–25° C., the solvent was evaporated off in vacuo and the residue was taken up in 200 ml of water and collected by suction filtration. The crude product was dissolved in aqueous acetic acid, washed with ethyl acetate and reprecipitated by addition of cold 6N sodium hydroxide solution. 49 g of the title compound was obtained. m.p. 97°–99° C., after crystallization from 75% ethanol.

8-(2-chloroethylthiomethyl)-3-methyl-4-oxo-2-phenyl-4H-1-benzopyran (Intermediate XXI)

A solution of 37 g of Intermediate XIX and 10.5 g of thiourea in 370 ml of ethanol was refluxed for 1 hour. The reaction mixture was cooled to ambient temperature, and 42 g of 8-amidinothiomethyl-3-methyl-4-oxo-2-phenyl-4H-1-benzopyran hydrochloride spontaneously crystallized. A sample recrystallized from ethanol had a melting point of 233°–235° C.

48 ml of 35% aqueous sodium hydroxide solution was added to a vigorously stirred suspension of 35 g of the compound thus prepared and 1.05 g of benzyl triethylammonium chloride in 440 ml of 1,2-dichloroethane. The mixture was stirred for 2.5 hours and then poured into 300 ml of water. The aqueous layer was extracted with 1,2-dichloroethane and the extracts were added to the organic layer which was washed with sodium chloride solution, dried on anhydrous sodium sulfate, and evaporated to dryness in vacuo. The residue was crystallized from methanol, giving 22 g of the title compound, m.p. 82°–83° C.

8-(2-hydroxyethoxymethyl)-3-methyl-4-oxo-2-phenyl-4H-1-benzopyran (Intermediate XXII)

A solution of 2.5 g of Intermediate XIX in 25 ml of xylene and 3 ml of dioxane was prepared. 0.15 g of sodium was dissolved in 3.10 ml of anhydrous ethylene glycol, and this solution was added dropwise at ambient temperature to the solution of Intermediate XIX. After refluxing for 5.5 hours, the reaction mixture was cooled to ambient temperature and poured into 50 ml of water. It was extracted with dichloromethane, and the extract was washed with sodium chloride solution, dried on anhydrous sodium sulfate and evaporated to dryness in vacuo. The solid residue was crystallized from ethanol, giving 2.1 g of the title compound, m.p. 132°–133° C.

8-trifluoroacetamido-3-methyl-4-oxo-2-phenyl-4H-1-benzopyran (Intermediate XXIII)

A solution of 9.5 ml of trifluoroacetic anhydride in 20 ml of anhydrous dichlorgmethane was added dropwise at −5°–0° C. to a solution of 5 g of 8-amino-3-methyl-4-oxo-2-phenyl-4H-1-benzopyran in 50 ml of anhydrous dichloromethane. The reaction mixture was stirred for 2 hours at 20°–25° C. and then poured on to crushed ice. The organic solution obtained by extraction with dichloromethane was washed with cold 5% aqueous sodium bicarbonate solution and with water, and was dried on anhydrous sodium sulfate. The solvent was removed in vacuo and the residue was crystallized from ethanol to give 5.2 g of the title compound, m.p. 175°–176° C.

8-aminomethyl-3-methyl-4-oxo-2-phenyl-4H-1-benzopyran (Intermediate XXIV)

A mixture of 21 g of Intermediate XXIX and 19 g of triphenylphosphine in 160 ml of tetrahydrofuran was stirred at ambient temperature for 8 hours. Thin layer chromatography showed the disappearance of Intermediate XXIX. 3 ml of water was added, and stirring was continued for a further 24 hours. The solvents were removed on a rotary evaporator, and the residue was dissolved in water as its acetate. The aqueous solution was washed with ethyl acetate, made basic with 37% sodium hydroxide solution and filtered on a Buchner funnel. The filter cake was washed with water and desiccated to give 18 g of the title compound. The hydrochloride, recrystallized from ethanol, had a melting point of 256°–258° C.

8-(2-chloroethylsulfonylmethyl)-3-methyl-4-oxo-2-phenyl-4H-1-benzopyran (Intermediate XXV)

41.6 ml of aqueous 30% hydrogen peroxide was added dropwise at 40° C. over a period of 20 minutes to a solution of 26.2 g of Intermediate XXI in 300 ml of glacial acetic acid. The mixture was heated to 60° C., stirred at that temperature for 4.5 hours, cooled to ambient temperature and poured into 60 ml of water. Filtration on a Buchner funnel gave a filter cake which was washed with water and desiccated, yielding 29.4 g of the title compound. A sample was crystallized from ethanol. m.p. (89) 159°–161° C.

8-(2-chloroethylsulfinylmethyl)-3-methyl-4-oxo-2-phenyl-4H-1-benzopyran (Intermediate XXVI)

36 ml of aqueous 30% hydrogen peroxide was quickly added dropwise at 10° C. to a solution of 12 g of Intermediate XXI in 84 ml of glacial acetic acid. The reaction mixture was stirred for 4 hours at ambient temperature, and then poured into 220 ml of water. The title compound was collected by suction filtration, washed with water and desiccated. Yield 12.4 g, m.p. 142°–145° C. (methanol).

8[N-methyl-N-(2-chloroethyl)-aminomethyl]-3-methyl-4-oxo-2-phenyl-4H-1-benzopyran (Intermediate XXVII)

A mixture of 22 g of Intermediate XX, 66 ml of 1-bromo-2-chloroethane and 11 g of anhydrous potassium carbonate in 88 ml of dimethylformamide was stirred at 20°–25° C. for 12 hours. The reaction mixture was then poured into 600 ml of water and extracted with dichloromethane. The organic layer was washed with water, dried on anhydrous sodium sulfate and acidified with ethanolic hydrogen chloride. The solvent and the excess 1-bromo-2-chloroethane were distilled off in vacuo at 70°–80° C. The residue was taken up in cold 1N aqueous sodium hydroxide solution and extracted with dichloromethane. The organic solution was washed with water, dried on anhydrous sodium sulfate and evaporated to dryness in vacuo at 25°–30° C. The crude title product was purified by flash chromatography on silica gel, eluting with ethyl acetate:petroleum ether 7:3, to give 18 g of the title compound melting at 118°–120° C. after crystallization from ethanol.

1-(2-hydroxy-2-methylpropyl)-4-(2-methoxyphenyl)-piperazine (Intermediate XXVIII)

. A mixture of 7 g of 1-(2-methoxyphenyl)-piperazine, 7.33 g of anhydrous potassium carbonate, 1.75 g of potassium iodide and 5.6 ml of 1-chloro-2-methyl-2-propanol was stirred for 90 minutes at 70° C. and for a further 6 hours at 90° C. The reaction mixture was poured into iced water and extracted with ethyl acetate. The organic layer was washed with aqueous sodium chloride solution, dried on anhydrous sodium sulfate and evaporated to dryness in vacuo. The title product was obtained as an oil, and was characterized as its dihydrochloride, crystallized from ethanol, melting at 225°–227° C.

8-azidomethyl-3-methyl-4-oxo-2-phenyl-4H-1-benzopyran (Intermediate XXIX)

A mixture of 22.8 g of Intermediate XIX and 6.8 g of sodium azide in 110 ml of dimethylformamide was stirred for 3 hours at 100° C. After cooling to ambient temperature, 130 ml of water and 88 ml of ethanol were added to the reaction mixture. After 1 hour, the crystals were collected by vacuum filtration, washed with water, and desiccated. Yield: 22 g of the title product. A sample recrystallized from ethanol had a melting point of 132°–134° C.

8-[N-(2-hydroxyethyl)-aminomethyl]-3-methyl-4-oxo-2-phenyl-4H-1-benzopyran (Intermediate XXX)

A solution of 2.38 g of anhydrous zinc chloride and 2.30 g of sodium cyanoborohydride in 71 ml of anhydrous methanol was added dropwise under stirring to a mixture of 9.24 g of 8-formyl-3-methyl-4-oxo-2-phenyl-4H-1-benzopyran and 9.12 g of ethanolamine in 90 ml of anhydrous methanol. Stirring was continued at 20°–25° C. for 5 hours, before removal of the solvent in vacuo.

250 ml of water was added to the residue, and the insoluble matter was collected by suction filtration and washed with water. The crude product was dissolved in 1N acetic acid and the solution was washed with ethyl acetate. The aqueous solution was then made alkaline by addition of 2N sodium hydroxide solution and the precipitate was collected by suction filtration and washed with water to give 8.5 g of the title compound, m.p. 117°–121°C. after drying at 60° C.

8-(N-methyl-N-chloracetyl-aminomethyl)-3-methyl-4-oxo-2-phenyl-4H-1-benzopyran (Intermediate XXXI)

A solution of 6 ml of chloracetyl chloride in 60 ml of 1,2-dichloroethane was added dropwise at −5° to 0° C. to a solution of 20 g of Intermediate XX and 10 ml of triethylamine in 200 ml of 1,2-dichloroethane. After stirring at 20°–25° C. for 2 hours, 150 ml of water was added to the reaction mixture and the phases were separated. The organic phase was washed with water and dried on anhydrous sodium sulfate. The solvent was removed in vacuo, and the residue was crystallized from ethanol to give 22.5 g of the title compound, m.p. 146°–148° C.

8-chloracetamidomethyl-3-methyl-4-oxo-2-phenyl-4H-1-benzopyran (Intermediate XXXII)

A solution of 3.2 ml of chloracetyl chloride in 32 ml of 1,2-dichloroethane was added dropwise, under stirring at −5° C., to a mixture of 10 g of Intermediate XXIV and 5.5 ml of triethylamine in 80 ml of 1,2-dichloroethane. The reaction mixture was stirred at ambient temperature for 1 hour and then 150 ml of water was added. The phases were separated; the aqueous phase was extracted with 1,2-dichloroethane and the extracts were added to the organic phase which was then washed with a cold saturated solution of sodium bicarbonate, washed with water, dried on anhydrous sodium sulfate and evaporated to dryness in vacuo. The residue was crystallized from ethanol to give 10.7 g of the title compound, m.p. 152°–155° C.

8-[N-acetyl-N-(2-chloroethyl)-aminomethyl]-3-methyl-4-oxo-2-phenyl-4H-1-benzopyran (Intermediate XXXIII)

8.65 g of Intermediate XXX and 4.15 ml of triethylamine were dissolved in 70 ml of tetrahydrofuran. To this solution, at −10° C., there was added dropwise over a period of 40 minutes a solution of 2.35 ml of acetyl chloride in 23 ml of tetrahydrofuran. After stirring for 3 hours at 0°–10° C. and for 2 hours at 20°–25° C., the solvent was evaporated off in vacuo.

100 ml of water was added to the residue, and extraction with dichloromethane was effected, pooling the successive organic extracts and then removing the solvent in vacuo. The residue was dissolved in 50 ml of methanol and 3 g of potassium carbonate and 10 ml of water were added. After stirring at 0° C. for 20 minutes, to hydrolyse the N,O-diacetyl derivative which had formed, the solvent was removed in vacuo and the residue was treated with water and dichloromethane as above described. The dichloromethane solution was again evaporated to dryness, and 5.9 g of 8-[N-acetyl-N-(2-hydroxyethyl)-amino-methyl]-3-methyl-4-oxo-2-phenyl-4H-1-benzopyran, m.p. 171°–172° C., was obtained.

3.6 ml of thionyl chloride in 30 ml of dichloromethane was added dropwise at 0° C. to a solution of 6.1 g of the compound thus prepared in 70 ml of dichloromethane. After stirring for 90 minutes at 20°–25° C., the reaction mixture was washed with water and dried. The solvent was removed in vacuo to give the crude title product for use without further purification.

8-(3-chloropropylthio)-3-methyl-4-oxo-2-phenyl-4H-1-benzopyran (Intermediate XXXIV)

A solution of 20.1 g of stannous chloride dihydrate in hydrochloric acid (d=1.18) was added over a period of 5 minutes at 65° C. to a solution of 6 g of Intermediate VIII in 70 ml of acetic acid. After 10 minutes, the reaction mixture was cooled to 30°–35° C. and the solvent was removed in vacuo. The residue was taken up in water, and the insoluble matter was collected by suction filtration, washed with water and dried. Yield 3.2 g of 8-mercapto-3-methyl-4-oxo-2-phenyl-4H-1-benzopyran, m.p. 115°–118° C. after crystallization from ethanol.

A mixture of 8 g of the compound so prepared, 27 ml of 1-bromo-3-chloro-propane, 0.2 g of tetrabutylammonium bromide and 6.2 ml of 35% sodium hydroxide in 80 ml of benzene was vigorously stirred for 4 hours at 20°–25° C. 100 ml of water and 40 ml of dichloromethane were added. The organic layer was separated off, washed with water and dried on anhydrous sodium sulfate. The solvents and excess 1-bromo-3-chloro-propane were removed in vacuo. The residue was purified by column chromatography on silica gel, eluting with petroleum ether:ethyl acetate 9:1, and 5.7 g of the title compound was obtained. After crystallization from methanol, it showed a melting point of 84°–86° C.

8-(3-chloropropylsulfonyl)-3-methyl-4-oxo-2-phenyl-4H-1-benzopyran (Intermediate XXXV)

7 ml of 30% hydrogen peroxide was added at 20°–25° C. to a solution of 3.65 g of Intermediate XXXIV in 35 ml of acetic acid. After stirring for 4 hours at 60° C., the reaction mixture was cooled to 20°–25° C. 30 ml of water was added. A precipitate formed, and was collected by suction filtration, washed with water and dried, yielding 3.4 g of the title compound. After crystallization from acetone, it showed a melting point of 160°–163° C.

8-(3-hydroxypropylcarbamoyl)-3-methyl-4-oxo-2-phenyl-4H-1-benzopyran (Intermediate XXXVI)

A solution of 7.6 ml of 3-aminopropanol in 50 ml of water was added dropwise over a period of 30 minutes to a suspension of 30 g of 3-methyl-4-oxo-2-phenyl-4H-1-benzopyran-8-carbonyl chloride and 15.2 g of potassium carbonate in 400 ml of acetone. The thick suspension was stirred for 3 hours at 20°–25° C. The solvents were removed in vacuo and the residue was taken up in 300 ml of water. After stirring for 1 hour, the precipitate was collected by suction filtration and washed with water. The crude product was purified by crystallization from 95% ethanol and 23.8 g of the title compound were obtained, m.p. 191°–193° C. An additional 4.7 g of the title compound was obtained by concentration in vacuo of the crystallization filtrate.

8-(3-chloropropylcarbamoyl)-3-methyl-4-oxo-2-phenyl-4H-1-benzopyran (Intermediate XXXVII)

A solution of 1.1 ml of thionyl chloride in 2 ml of chloroform was added to a boiling solution of 3.37 g of Intermediate XXXVI in 20 ml of chloroform. After stirring for 90 minutes under reflux, the solvent was removed in vacuo and the residue was crystallized from acetonitrile to give 3 g of pure title compound, m.p. (188) 193°–194° C.

8-[1-hydroxy-4-(4-methylphenylsulfonyloxy)-butyl]-3-methyl-4-oxo-2-phenyl-4H-1-benzopyran (Intermediate XXXVIII)

1.12 g of sodium cyanide in 3 ml of water was added at 20°–25° C. to a stirred mixture of 3.96 g of 8-formyl-3-methyl-4-oxo-2-phenyl-4H-1-benzopyran, 2.61 g of morpholine and 4.48 g of p-toluenesulfonic acid in 20 ml of tetrahydrofuran and 30 ml of 1,2-dichloroethane. The reaction mixture was refluxed for 4 hours, and then 10 ml of cold water was added. The tetrahydrofuran was distilled off at normal pressure, and 10 ml of 1,2-dichloromethane and 10 ml of chloroform were added. The organic phase was separated, washed with aqueous sodium chloride solution, dried over anhydrous sodium sulfate and evaporated to dryness in vacuo. The residue was suspended in diethyl ether, filtered off, and crystallized from chloroform:ethyl acetate. Yield: 3.55 g of 8-(N-morpholinyl)cyanomethyl-3-methyl-4-oxo-2-phenyl-4H-1-benzopyran, m.p. 236°–238° C.

3.5 ml of a 30% solution of potassium hydroxide in anhydrous methanol was added under stirring at ambient temperature to a suspension of 22.8 g of the compound thus prepared in 520 ml of anhydrous tetrahydrofuran. 6.3 ml of acrylonitrile in 20 ml of tetrahydrofuran was dropped into this suspension, and the reaction mixture was stirred at ambient temperature for 1 hour. The solvents were evaporated off in vacuo. Crystallization of the residue from methanol gave 23.22 g of 8-(1,3-dicyano-1-morpholinopropyl)-3-methyl-4-oxo-2-phenyl-4H-1-benzopyran.

23.2 g of the compound thus prepared was dissolved in 250 ml of dioxane. 250 ml of 6M hydrochloric acid was added and the mixture was refluxed for $2\pi$ hours. After cooling to ambient temperature, the mixture was poured into 700 ml of aqueous sodium chloride solution and extracted with ethyl acetate. The extracts were washed with aqueous sodium chloride solution and treated with 700 ml of 1M sodium hydroxide solution. The aqueous layer was washed with ethyl acetate and acidified with 37% hydrochloric acid. The precipitate was collected by suction filtration and crystallized from ethanol to give 10.2 g of 8-(3-carboxy-1-oxopropyl)-3-methyl-4-oxo-2-phenyl-4H-1-benzopyran, m.p. 191°–192° C.

Diborane, generated by dropping a solution of 2.1 ml of freshly distilled boron trifluoride diethyl etherate in 10 ml of anhydrous diglyme into 19 ml of a 0.66M solution of sodium borohydride in diglyme, was bubbled into a suspension of 2.28 g of the compound thus prepared in 23 ml of anhydrous tetrahydrofuran, stirred at 0° C. under nitrogen flux. Stirring was continued for 20 minutes at 0° C. and for a further 20 minutes at ambient temperature. Methanol was cautiously dropped into the mixture at 0° C. to quench the reaction. The solvents were removed by evaporation in vacuo. The residue was purified by flash chromatography on silica gel, eluting with petroleum ether:ethyl acetate 3:7. The collected fractions were evaporated in vacuo to leave 2 g of 8-(1,4-dihydroxy-butyl)-3-methyl-4-oxo-2-phenyl-4H-1-benzopyran, m.p. 133°–134° C.

2.8 g of p-toluenesulfonyl chloride was added at 0° C. to a stirred solution of 3.17 g of the compound thus prepared in 32 ml of anhydrous pyridine. The mixture was stirred for 6 hours at 0° C. and stood overnight at −4° C. without stirring. It was then poured into 200 ml of aqueous sodium chloride solution, acidified with 10 ml of 12N hydrochloric acid and filtered under suction. The filter cake was dissolved in chloroform, and the solution was washed with aqueous sodium chloride solution and dried on anhydrous sodium sulfate. The solvent was distilled off in a rotary evaporator. The residue was purified by flash chromatography on silica gel, eluting with petroleum ether:ethyl acetate 1:1. The collected fractions were evaporated to dryness in vacuo, yielding 3.04 g of pure title product, m.p. 123°–124° C.

4-[4-(2-methoxyphenyl)-1-piperazinyl]-butyraldehyde (Intermediate XXXIX)

A solution of 5.4 g of 2-(3-chloropropyl)-dioxolan and 15.9 g of 1-(2-methoxyphenyl)-piperazine in 60 ml of dimethylformamide was stirred at 80° C. for 4 hours. After cooling to 20°–25° C., the reaction mixture was poured into 500 ml of ice cold 0.5N sodium hydroxide solution and extracted with dichloromethane. The organic phase was washed with water and dried on anhydrous sodium sulfate. The solvent was removed in vacuo, and the residue was purified by flash chromatography on silica gel, eluting with dichloromethane:ethanol 95:5. 9.8 g of 2-{3-[4-(2-methoxyphenyl)-1-piperazinyl]-propyl}-dioxolan was obtained as an oil.

NMR CDCl3 ($\delta$) 1.5–2.0 (4H, m, CH$_2$CH$_2$CH) 2.2–3.2 (10H, m, 5×CH$_2$N) 3.7–4.0 (7H, m, OCH$_3$ and 2×OCH$_2$) 4.8 (1H, t, OCHO) 6.7–6.9 (4H, m, aromatic protons)

A solution of 12.8 g of the compound thus prepared in 200 ml of tetrahydrofuran and 420 ml of 1N hydrochloric acid was maintained at 20°–25° C. for 24 hours. It was then made alkaline with 5N sodium hydroxide solution and immediately extracted with dichloromethane. The organic layer was washed with water and dried on anhydrous sodium sulfate. The solvent was evaporated off in vacuo, and the residue was purified by flash chromatography on silica gel, eluting with dichloromethane: methanol 97:3. 6.4 g of the title compound was obtained as an oil.

NMR CDCl3 ($\delta$) 1.5–2.0 (2H, m, CH$_2$CH$_2$CH$_2$) 2.2–2.8 (8H, m, 3×CH$_2$N and CH$_2$CHO) 2.9–3.2 (4H, m, 2×CH$_2$NAr) 3.8 (3H, s, OCH$_3$) 6.8 (4H, s, aromatic protons) 9.3 (1H, s, CHO).

8-(2,3-epoxypropoxy)-3-methyl-4-oxo-2-phenyl-4H-1-benzopyran (Intermediate XL)

7 ml of 2,3-epoxypropyl chloride was added dropwise at 20°–25° C. to a stirred mixture of 5 g of 8-hydroxy-3-methyl-4-oxo-2-phenyl-4H-1-benzopyran and 9.7 ml of 2N sodium hydroxide in 10 ml of ethanol. After 6 hours at 20°–25° C., the reaction mixture was poured into 100 ml of water and the precipitate which formed was collected by suction filtration. After drying and purifying by flash chromatography on silica gel (eluant petroleum ether: ethyl acetate 65:35), there was obtained 4.45 g of the title compound, m.p. 128°–129° C.

8-[N-methyl-2-(4-methylphenylsulfonyloxy)ethylsulfamyl]-3-methyl-4-oxo-2-phenyl-4H-1-benzopyran (Intermediate XLI)

A solution of 5 g of Intermediate VIII in 60 ml of dichloromethane and 20 ml of tetrahydrofuran was added dropwise at 0° C. to a mixture of 2.5 ml of 2-methylaminoethanol and 2.1 ml of triethylamine in 20 ml of dichloromethane. After stirring for 2 hours at 20°–25° C., 100 ml of water and 100 ml of dichloromethane were added to the reaction mixture. The phases were separated and the organic solution was dried on anhydrous sodium sulfate. The solvent was removed in vacuo, and the residue was purified by column chromatography on silica gel, eluting with petroleum ether:ethyl acetate 3:7. There was thus obtained 4.5 g of 8-(N-methyl-2-hydroxyethyl-sulfamyl)-3-methyl-4-oxo-2-phenyl-4H-1-benzopyran, melting at 146°–147° C. after crystallization from ethanol.

The compound thus prepared was converted to the title compound by p-toluene sulfonylation according to the second step of the procedure described below for the preparation of Intermediate XLII. The title compound was used without further purification.

8-[2-(4-methylphenylsulfonyloxy)ethylsulfamyl]-3-methyl-4-oxo-2-phenyl-4H-1-benzopyran (Intermediate XLII)

A solution of 5 g of Intermediate VIII in 37 ml of tetrahydrofuran was added dropwise at 0° C. to a mixture of 2.5 ml of ethanolamine and 2.5 ml of triethylamine in 25 ml of tetrahydrofuran. After stirring at 20°–25° C., the reaction mixture was poured into 400 ml of water. A precipitate formed, and was collected by suction filtration, washed with water and air dried, yielding 4.6 g of 8-(2-hydroxyethylsulfamyl)-3-methyl-4-oxo-2-phenyl-4H-1-benzopyran, melting at 186°–187° C. after crystallization from ethyl acetate.

2.1 g of p-toluenesulfonyl chloride was added portionwise at 0° C. to a solution of 3.6 g of the compound thus prepared in 25 ml of pyridine. After 6 hours at 20°–25° C., the reaction mixture was slowly poured on to crushed ice containing a slight excess of hydrochloric acid. A precipitate formed and was collected by suction filtration and washed with water. 4.9 g of the title compound was obtained, melting at (163) 166°–169° C. after crystallization from ethyl acetate.

8-(3-aminopropylcarbamoyl)-3-methyl-4-oxo-2-phenyl-4H-1-benzopyran hydrochloride (Intermediate XLIII)

A solution of 21.6 g of 3-methyl-4-oxo-2-phenyl-4H-1-benzopyran-8-carbonyl chloride in 250 ml of anhydrous tetrahydrofuran was dropped at 0°–10° C. into a stirred solution of 17 g of 3-(2-methyl-2-propoxycarbamoyl)-propylamine (prepared as described in Saari, W. S. et al., *J. Med. Chem.* 33: 97, 1990) and 13 ml of triethylamine. After stirring for 2 hours at ambient temperature, the reaction mixture was poured into water and filtered to recover 12.3 g of N,3-(2-methyl-2-propoxycarbamoyl)-propyl-3-methyl-4-oxo-2-phenyl-4H-1-benzopyran-8-carboxamide which was recrystallized from ethanol, m.p. 178°–180° C.

A solution of 4.3 ml of trifluoroacetic acid in 15 ml of anhydrous dichloromethane was added dropwise at −5° C. under stirring to a solution of 3.3 g of the compound thus prepared in 35 ml of anhydrous dichloromethane. After warming to ambient temperature, the mixture was stirred for 8 hours. The dichloromethane and the excess trifluoroacetic acid were evaporated off at 20°–25° C. using a rotary evaporator. The oily residue was dissolved in dichloromethane and 1N sodium hydroxide solution was added. The organic layer was washed with water, dried on anhydrous sodium sulfate and filtered. Excess ethanolic hydrogen chloride was added to the filtrate, and the solvent was removed in vacuo. The residue was crystallized from ethanol to give 1.5 g of the title compound, m.p. 253°–255° C.

8-(2-chloroethylureido)-3-methyl-4-oxo-2-phenyl-4H-1-benzopyran (Intermediate XLIV)

4 ml of 2-chloroethylisocyanate were added, under stirring at ambient temperature, to a solution of 3.9 g of 8-amino-3-methyl-4-oxo-2-phenyl-4H-1-benzopyran in 52 ml of anhydrous dimethylformamide. Stirring was continued at 70° C. for 5 hours. Water was added to the reaction mixture, which was then extracted with ethyl acetate. The organic phase was evaporated to dryness in vacuo. The residue was suspended in diethyl ether under stirring. The title product was then filtered off and recrystallized from methanol. Yield 3.74 g, m.p. 213°–214° C.

(Z,E)-8-{4-[2-(1,3-dioxanyl)]-1-butenyl}-3-methyl-4-oxo-2-phenyl-4H-1-benzopyran (Intermediate XLV)

1.6 ml of 2.5N butyl lithium in hexane was added dropwise at −20° C. to a solution of 1.53 g of 2-[2-(1,3dioxanyl)]-ethyl triphenylphosphonium bromide in 10 ml of anhydrous tetrahydrofuran. The mixture was stirred for 20 minutes at −20° C. A solution of 0.8 g of 8-formyl-3-methyl-4-oxo-2-phenyl-4H-1-benzopyran in 11 ml of anhydrous tetrahydrofuran was dropped into the mixture, which was then warmed to 0° C. over a period of 90 minutes and then to ambient temperature over a period of 30 minutes. The reaction was quenched by addition of methanol. The solvents were evaporated off in vacuo and the residue was purified by flash chromatography on silica gel, eluting with ethyl acetate:petroleum ether 3:7, to give the title compound, as a mixture of diastereoisomers E and Z, m.p. (93) 98°–100° C. The ratio of the two isomers was determined by NMR spectroscopy and resulted E:Z=65:35.

NMR, CDCl$_3$ (δ)

| | | |
|---|---|---|
| 8.1–8.2 | (m, 1H) | CH in position 5 of the benzopyran ring |
| 7.2–7.8 | (m, 7H) | other aromatic CH groups of the benzopyran ring |
| 6.9 | (dt, 1H) | Fl'—CH of the E isomer |
| 6.8 | (dt, 1H) | Fl'—CH of the Z isomer |
| 6.4 | (dt, 1H) | Fl'—CH=CH of the E isomer |
| 5.9 | (dt, 1H) | Fl'—CH=CH of the Z isomer |
| 4.6–4.7 | (m, 1H) | OCHO |
| 3.6–4.2 | (m, 4H) | CH$_2$O of the dioxane ring |
| 2.4–2.7 | (m, 2H) | CHCH$_2$CH |
| 1.9–2.3 | (m, 5H) | CH$_3$ and CH$_2$ in position 5 of the dioxane ring |

8-{4-[2-(1,3-dioxanyl)]-butyl}-3-methyl-4-oxo-2-phenyl-4H-1-benzopyran (Intermediate XLVI)

A mixture of 0.2 g of 10% palladium-on-carbon catalyst and of 1 g of Intermediate XLV in 24 ml of methanol was hydrogenated in a Parr apparatus at ambient temperature with a hydrogen pressure of 1.5 atmospheres. After the theoretical hydrogen consumption, the catalyst was filtered off and the solvent was removed by evaporation in vacuo. The residue was crystallized from cyclohexane to give the title compound, m.p. 118°–119.5° C.

8-carboxymethyl-3-methyl-4-oxo-2-phenyl-4H-1-benzopyran (Intermediate XLVII)

4.5 g of potassium permanganate was added portionwise within 1.5 hours under stirring at 0°–10° C., to a mixture of 2.76 g of 8-allyl-3-methyl-4-oxo-2-phenyl-4H-1-benzopyran (P. Da Re, U.S. Pat. No. 3,350,411), 0.17 g of Aliquat 336, 1.12 ml of acetic acid, 56 ml of dichloromethane, 3.2 ml of sulfuric acid (d=1.84) and 60 ml of water. Stirring was continued at room temperature for 5 hours. 3.4 g of sodium metabisulfite were added portionwise at 0°–5° C. within 15 minutes. The organic layer was separated, washed with water and extracted with 60 ml of 1N aqueous sodium hydroxide solution. The aqueous phase was acidified by addition of diluted hydrochloric acid and extracted with ethyl acetate. The organic phase was washed with water, dried on anhydrous sodium sulfate and, after filtration, evaporated to dryness in vacuo. The residue was treated with carbon tetrachloride and the solid was collected by suction to give 1 g of the title compound, m.p. 191°–192° C. (acetonitrile).

8-(4-chlorobutyramido)-3-methyl-4-oxo-2-phenyl-4H-1-benzopyran (Intermediate XLVIII)

The title compound was prepared in the same manner as Intermediate X, but using 4-chlorobutyryl chloride instead of acryloyl chloride. The solid obtained, filtered from water and dried, was rinsed with hot diethyl ether and collected by suction to give the title compound. A sample, crystallized from 50% aqueous ethanol and washed with diethyl ether, melted at (153) 162°–164° C.

8-methylamino-3-methyl-4-oxo-2-phenyl-4H-1-benzopyran (Intermediate XLIX)

A solution of 0.5 g of Intermediate XXIII in 1.5 ml of anhydrous dimethylformamide was added dropwise under stirring, at −5° C. to 0° C., to a suspension of 0.045 g of sodium hydride (80% in mineral oil). After stirring at room temperature for 1 hour, 0.092 ml of methyl iodide in 0.6 ml of anhydrous dimethylformamide was added dropwise. Then, the reaction mixture was stirred at 50° C. for 1 hour, cooled to 20° C., poured into water, filtered by suction and dried at 60° C. for 3 hours to recover 0.6 g of 8-(N-methyltrifluoroacetamido)-3-methyl-4-oxo-2-phenyl-4H-1-benzopyran.

| NMR (CDCl$_3$; ($\delta$)) | | |
|---|---|---|
| 8.15 | (dd, 1H) | benzopyran CH in 5 |
| 7.10–7.60 | (m, 7H) | benzopyran protons |
| 3.30 | (s, 3H) | CH$_3$—N |
| 2.10 | (s, 3H) | benzopyran CH$_3$ in 3 |

A mixture of 0.44 g of the above compound and 0.05 g of sodium borohydride in 4 ml of ethanol and 1 mL of dimethyl-sulfoxide was stirred at room temperature for 1 hour, then quenched with an excess of 4N hydrochloric acid. After removal of ethanol by evaporation in vacuo, the residue was rinsed with water, then with 3N sodium hydroxide and extracted with ethyl acetate. The organic layer was washed with water, dried on anhydrous sodium sulfate and evaporated to dryness in vacuo. The solid residue was crystallized from ethanol to give 0.22 g of the title compound, melting at 143°–146° C.

8-(N-methylacrylamido)-3-methyl-4-oxo-2-phenyl-4H-1-benzopyran (Intermediate L)

This compound was prepared in the same manner as Intermediate X, but using Intermediate XLIX instead of 8-amino-3-methyl-4-oxo-2-phenyl-4H-1-benzopyran. Instead of diluting with water, THF was removed by evaporation in vacuo and the crude residue was dissolved in ethyl acetate and washed with water. The organic solution was dried on anhydrous sodium sulfate and evaporated to dryness in vacuo to give the title compound. A sample, purified by column chromatography on silica gel (eluting with ethyl acetate-petroleum ether 4:6) and crystallized from cyclohexane, melted at 136°–137° C.

1-[2-(1,3-dihydro-1,3-dioxo-2H-isoindol-2-yloxy)ethyl]-4-(2-methoxyphenyl)piperazine. (Intermediate LI)

A mixture of 6.73 g of N-hydroxyphthalimide, 3.73 g of sodium acetate and 10 g of 1-(2-chloroethyl)-4-(2-methoxyphenyl)piperazine in 100 ml of anhydrous dimethylsulfoxide was stirred at 100° C. for 4 hours. The reaction mixture was then cooled to room temperature, poured into water and extracted with ethyl acetate. The collected organic layers were washed with 1N sodium hydroxide, dried on anhydrous sodium sulfate and evaporated to dryness in vacuo to give 7.58 g of the title compound. A sample was crystallized from cyclohexane, m.p. (76) 80°–83° C.

1-(2-aminooxyethyl)-4-(2-methoxyphenyl)piperazine hydrochloride (Intermediate LII)

A solution of 6.59 g of Intermediate LI and 1.10 ml of 85% hydrazine hydrate in 130 ml of 95% ethanol was refluxed for 4 hours. Ethanol was removed by evaporation in vacuo. The residue was rinsed with water then with an excess of 37% hydrochloric acid and filtered. The acid aqueous solution was made basic with 5% sodium hydroxide and extracted with chloroform. The organic layer was dried on anhydrous sodium sulfate and evaporated to dryness in vacuo to give 4.3 g of the title compound as an oil. A sample was converted to the hydrochloride by salification with ethanolic hydrochloric acid in dichoromethane. The solvents were removed by evaporation in vacuo and the crude residue was crystallized from ethanol, giving the title compound, m.p. 208°–209° C.

8-(4-chlorobutylthio)-3-methyl-4-oxo-2-phenyl-4H-1-benzopyran (Intermediate LIII)

The title compound was prepared in the same manner as Intermediate XXXIV, but using 1-bromo-4-chlorobutane instead of 1-bromo-3-chloropropane. m.p. 81°–84° C. (ethanol).

8-(4-chlorobutylsulfinyl)-3-methyl-4-oxo-2-phenyl-4H-1-benzopyran (Intermediate LIV)

The title compound was prepared in the same manner as Intermediate XXVI, but using Intermediate LIII instead of Intermediate XXI. A sample, crystallized from cyclohexane-benzene 0.5: 1, melted at 124°–125° C.

8-carboxy-4-oxo-3-phenyl-4H-1-benzopyran (Intermediate LV)

A solution of 38.22 g of silver nitrate in 75 ml of water was added dropwise, under stirring, at 20°–25° C., to a solution of 22.5 g of 8-formyl-4-oxo-3-phenyl-4H-1-benzopyran (prepared as described by G. Atassi et al., Eur. J. Med. Chem.—Chim. Ter. 20, 393 (1985)) in 150 ml of 85% ethanol and 450 ml of N,N-dimethylformamide. Then, a solution of 32.67 g of 85% potassium hydroxide in 195 ml of water was added drop-wise under stirring at 15°–20° C. After additional stirring at room temperature, the reaction mixture was filtered by suction; the mother liquor was acidified with 37% hydrochloric acid and diluted with 1.2 l of water. Filtration by suction and washing with water to neutrality gave the title compound as a crude. The crude was suspended in 150 ml of ethyl acetate and stirred with 444 ml of 0.3M sodium hydrogen carbonate until clear layers were obtained. The aqueous layer was washed with 75 ml of ethyl acetate, then made acidic with 37% hydrochloric acid, filtered and dried at 60°–65° C. to give 19,12 g of the title compound that melted at (215) 218° C. A sample, crystallized from ethanol, showed the same melting point, m.p. (215) 218° C.

8-chlorocarbonyl-4-oxo-3-phenyl-4H-1-benzopyran (Intermediate LVI)

A mixture of 15.97 g of Intermediate LV and 15.6 ml of thionyl chloride in 75 ml of anhydrous toluene was stirred at 80°–85° C. for 4 hours. After removal of the solvent under vacuo, the residue was rinsed twice with 20 ml of toluene and evaporating to dryness in vacuo to give, after drying, 16 g of the title compound melting at (126) 138°–140° C. which was used without further purification. m.p. (130) 138°–140° C. (toluene).

8-(N-acetylcarbamoyl)-3-methyl-4-oxo-2-phenyl-4H-1-benzopyran Intermediate LVII

A mixture of 3.5g of 8-carbamoyl-3-methyl-4-oxo-2-phenyl-4H-1-benzopyran (described in JP 61-238783, 1986), 4.8 ml of acetic anhydride and 0.25 ml of sulfuric acid (d=1,098) was stirred at 140° C. for 3 minutes. The reaction was cooled to ambient temperature, diluted with water and filtered by suction to give, after washing with water and desiccation, 3.88g of the title compound

| $^1$H-NMR (CDCl$_3$; δ): | | |
|---|---|---|
| 10.50 | bs, 1H | imidic NH |
| 8.35–8.70 | m, 2H | CH in position 5 and 7 of the benzopyran ring |
| 7.45–8.00 | m, 6H | other aromatic CH's |
| 2.60 | s, 3H | CH$_3$CO |
| 2.20 | s, 3H | CH$_3$ in position 3 of the benzopyran ring |

1-(3-amino-2,2-dimethylpropyl)-4-(2-methoxyphenyl)-piperazine

The title compound may be prepared by treating 1-(2-methoxyphenyl)-piperazine with isobutyraldehyde, 37% formaldehyde in water and acetic acid at 90°–150° C. or with the same in ethanolic hydrogen chloride (Mannich reaction) to give 1-(2-formyl-2-methylpropyl)-4-(2-methoxyphenyl)-piperazine, which is then aminated by treatment with excess ammonia under reducing conditions. The latter may be hydrogen and a catalyst (for example, palladium-on-charcoal, Raney nickel or platinum dioxide) in a solvent (for example, ethanol, methanol, isopropanol, dichloromethane, chloroform or dimethylformamide) at between ambient temperature and 80° C., or alternatively a metal hydride (for example, sodium borohydride, sodium or potassium cyanoborohydride, or sodium triacetoxyborohydride) in a solvent (for example, methanol, ethanol, chloroform, benzene or 1,2-dichloroethane) in the presence of an acid (for example, gaseous hydrogen chloride or acetic acid).

It may be reacted with 3-methyl-4-oxo-2-phenyl-4H-1-benzopyran-8-carbonyl chloride in the manner described in Example 12 hereinbelow to give 8-{2,2-dimethyl-3-[4-(2-methoxyphenyl)-1-piperazinyl]-propylcarbamoyl}-3-methyl-4-oxo-2-phenyl-4H-1-benzopyran [Fl'-Y3-CH$_2$-C(CH$_3$)$_2$-CH$_2$-B1(OCH$_3$)].

8-trifluoroacetamidomethyl-3-methyl-4-oxo-2-phenyl-4H-1-benzopyran

This compound can be prepared according to the procedure described for Intermediate XXIII but using Intermediate XXIV instead of 8-amino-3-methyl-4-oxo-2-phenyl-4H-1-benzopyran.

It can be used as starting material, instead of Intermediate XXIII, in the same reaction as that described in Example 32 to yield 8-{2[4-(2-methoxyphenyl)-1-piperazinyl]-ethylamino}-methyl-3-methyl-4-oxo-2-phenyl-4H-1-benzopyran (Fl'-Y15-(CH$_2$)2-B1(OCH$_3$)).

8-[4-(4-methyl)-benzenesulfonyloxy]but(1-2)enyl-3-methyl-4-oxo-2-phenyl-4H-1-benzopyran This intermediate can be prepared by reacting 8-formyl-3-methyl-4-oxo-2-phenyl-4H-1-benzopyran with 3-hydroxypropyltriphenylphosphonium bromide in the presence of n-butyllithium or lithium bis-(trimethylsilyl)amide in tetrahydrofuran at −30° C.—room temperature to yield the corresponding 4-butenol which can be esterified with 4-methylbenzenesulfonyl chloride in pyridine or pyridine-dichloromethane at ambient temperature. The so obtained title intermediate can be reacted with a compound H-B, according to Path (a) to give the desired final compounds Fl'-Y8-(CH$_2$)2-B.

8-(2-chloroethylureido)methyl-3-methyl-4-oxo-2-phenyl-4H-1-benzopyran

This intermediate can be prepared operating as described for Intermediate XLIV by using Intermediate XXIV instead of 8-amino-3-methyl-4-oxo-2-phenyl-4H-1-benzopyran.

It can be reacted with a compound of formula H-B, according to Path (a) to give the desired final compounds Fl'Y-21-(CH$_2$)$_2$-B.

8-ethenylsulfonylaminomethyl-3-methyl-4-oxo-2-phenyl-4H-1-benzopyran

This compound can be prepared by reacting Intermediate XXIV with 2-chloroethylsulfonylchloride in an halogenated solvent (e.g. dichloromethane) in presence of triethylamine at 0°–40° C., according to A.A. Goldberg, Jr. Chem. Soc. (1945), 464.

It can be reacted with the appropriate compounds 4-B, according to Path (m) to yield the final compounds Fl'-Y22-(CH$_2$)-B.

Operating as described above, but starting from 8-amino-3-methyl-4-oxo-2-phenyl-4H-1-benzopyran the final compounds Fl'-Y36-(CH$_2$)2-B can be obtained.

8-chlorosulfonylmethyl-3-methyl-4-oxo-2-phenyl-4H-1-benzopyran

This intermediate can be prepared by reacting 8-amidinothiomethyl-3-methyl-4-oxo-2-phenyl-4H-1-benzopyran (whose synthesis is described in Intermediate XXI) with chlorine gas in water at −10°/10° C. according to T. B. Johnson et al., J. Chem. Soc., 61,2548 (1939). By reaction of this intermediate with the appropriate compounds A-NH-Z-B (A=H or CH$_3$) according to Path n the final Fl'-Y27-(CH$_2$)$_n$-B and Fl'-Y28-(CH$_2$)$_n$-B can be obtained.

EXAMPLES

Example 1

8-{2-[4-(2-methoxyphenyl)-1-piperazinyl]-1-oxoethyl}-3-methyl-4-oxo-2-phenyl-4H-1-benzopyran hydrochloride Fl'-Y1-CH$_2$,B1(CH$_3$)

A solution of 11.5 g of 1-(2-methoxyphenyl)-piperazine in 30 ml of methanol was added dropwise at 20°–25° C. to a stirred mixture consisting of 21.4 g of Intermediate VI and 4.1 g of potassium carbonate in 120 ml of methanol. After 4 hours stirring at the same temperature, the reaction mixture was stripped in vacuo. The residue was extracted with chloroform and the organic solution was washed with water, dried on anhydrous sodium sulfate/calcium chloride, filtered and stripped in vacuo. The obtained crude product was dissolved in acetone and a slight excess of ethanolic hydrogen chloride was added. After collection by suction filtration and recrystallization from 95% ethanol, 16.3 g of the title compound was obtained (m.p. (189)195°–199° C.).

Example 2

8-{2-[4-(2-methylphenyl)-1-piperazinyl]-1-oxoethyl}-3-methyl-4-oxo-2-phenyl-4H-1-benzopyran hydrochloride-Fl'-Y1-CH$_2$-B1(CH$_3$)

This compound was prepared according to Example 1, but using 1-(2-methylphenyl)-piperazine instead of 1-(2-methoxyphenyl)-piperazine and carrying out the reaction in dimethylformamide for 1 hour instead of in methanol for 4 hours, m.p. (194)203°–206° C. (2-propanol).

Example 3

8-{2-[4-(2-ethoxyphenyl)-1-piperazinyl]-1-oxoethyl}-3-methyl-4-oxo-2-phenyl-4H-1-benzopyran hydrochloride -Fl'-Y1-CH$_2$-B1(OC$_2$H$_5$)

This compound was prepared according to Example 1 but using 1-(2-ethoxyphenyl)-piperazine instead of 1-(2-methoxyphenyl)-piperazine and carrying out the reaction in dimethylformamide for 2 hours instead of in methanol for 4 hours. m.p. 208°–210° C. (2-propanol).

Example 4

8-{3-[4-(2-methoxyphenyl)-1-piperazinyl]-1-oxo-propyl}-3-methyl-4-oxo-2-phenyl-4H-1-benzopyran hydrochloride -Fl'-Y1-$(CH_2)_2$-B1$(OCH_3)$ A solution of 10 ml of 37% formaldehyde in 15 ml of methanol was dropped, over a period of 3 minutes at 0° C., into a solution of 5.75 g of 1-(2-methoxyphenyl)-piperazine in 10 ml of methanol. After 12 hours at 0° C., the mixture was stripped in vacuo and redissolved in 15 ml of methanol. 20 ml of 3.6N hydrogen chloride in diethyl ether was added at 0° C. After stripping in vacuo, the residue was suspended in 15 ml of 1,4-dioxane. A solution of 8.3 g of Intermediate V in 100 ml of 1,4-dioxane was added under stirring at 20°–25° C. After stirring for 8 hours at reflux the reaction mixture was cooled to 30°–40° C. 50 ml of methanol was added and the mixture was refluxed for a further 2 hours. After cooling to 20°–25° C., the resultant solution was diluted with 300 ml of diethyl ether. Stirring was continued for a further 3 hours at the same temperature. The title compound was collected by suction filtration and recrystallization from ethanol. Yield 4 g, m.p. 209°–210° C.

Example 5

8-{3-[4-(2-methoxyphenyl)-1-piperazinyl]-propoxycarbonyl}-3-methyl-4-oxo-2-phenyl-4H-1-benzopyran dihydrochloride Fl'-Y2-$(CH_2)_3$-B1$(OCH_3)$ A mixture of 4.24 g of 8-carboxy-3-methyl-4-oxo-2-phenyl-4H-1-benzopyran and 6.3 g of anhydrous potassium carbonate in 60 ml of dimethylformamide was stirred at 80° C. for 30 minutes. 5.23 g of 1-(3-chloropropyl)-4-(2-methoxyphenyl)piperazine was then added and stirring was continued at 80° C. for 3.5 hours. The reaction mixture was cooled to ambient temperature, poured on to iced water and extracted with ethyl acetate. The organic extracts were washed with aqueous sodium chloride solution, dried on anhydrous sodium sulfate, and evaporated to dryness in vacuo. The residue was taken up in ethanol and excess ethanolic hydrogen chloride was added to the solution. Yield: 8.16 g of the title compound, m.p. 198°–203° C.

Example 6

8-{2-[4-(2-methoxyphenyl)-1-piperazinyl]ethoxycarbonyl}-3-methyl-4-oxo-2-phenyl-4H-1-benzopyran dihydrochloride Fl'-Y2-$(CH_2)_2$-B1$(OCH_3)$ Operating as described in Example 5, but using 1-(2-chloroethyl)-4-(2-methoxyphenyl)-piperazine instead of 1-(3-chloropropyl)-4-(2-methoxyphenyl)-piperazine, the title compound was obtained, m.p. 200°–203° C. from ethanol.

Example 7

8-{3-[4-(2-chlorophenyl)-1-piperazinyl]-propoxycarbonyl}-3-methyl-4-oxo-2-phenyl-4H-1-benzopyran dihydrochloride Fl'-Y2-$(CH_2)_3$-B1$(Cl)$ A mixture of 2.8 g of 1-(2-chlorophenyl)-piperazine hydrochloride and 4.2 g of anhydrous potassium carbonate in 25 ml of dimethylformamide was stirred at ambient temperature for 15 minutes. 4.81 g of Intermediate I was added, and stirring was continued for 2 days. The reaction mixture was then poured into 200 ml of cold water, and extracted with diethyl ether and ethyl acetate. The organic extracts were washed in turn with aqueous sodium chloride solution, 0.1N acetic acid, aqueous sodium chloride solution, aqueous 4% sodium carbonate solution and water, and were then dried on anhydrous sodium sulfate. After evaporation to dryness in vacuo, the residue was dissolved in 160 ml of acetonitrile and excess hydrogen chloride in diethyl ether was added. The insoluble title compound was recrystallized from acetonitrile. Yield 3.6 g, m.p. 138°–143° C.

Example 8

8-[3-(4-phenyl-1-piperazinyl)-propoxycarbonyl]-3-methyl-4-oxo-2-phenyl-4H-1-benzopyran dihydrochloride Fl'-Y2-$(CH_2)_3$-B1$(H)$ The title compound was prepared by the method described in Example 7, but using 1-phenyl-piperazine in place of 1-(2-chlorophenyl)-piperazine hydrochloride. Recrystallization was from methanol; the melting point was 229°–231° C.

Example 9

8-{3-[4-(2-methoxyphenyl)-1-piperazinyl]propoxycarbonyl}-3-methyl-4-oxo-2-phenyl-4H-1-benzopyran dihydrochloride Fl'-Y2-$(CH_2)_3$-B1$(OCH_3)$ Operating as described in Example 7, but using 1-(2-methoxyphenyl)-piperazine hydrochloride instead of 1-(2-chlorophenyl)-piperazine hydrochloride, the title compound was obtained. This represents an alternative route to the product of Example 5.

Example 10

8-{3-[4-(2-methoxyphenyl)-1-piperazinyl]-2-methyl-2-propoxycarbonyl}-3-methyl-4-oxo-2-phenyl-4H-1-benzopyran dihydrochloride Fl'-Y2-$C(CH_3)_2$-$CH_2$-B1$(OCH_3)$ 5.29 g of Intermediate XXVIII in 25 ml of 1,2-dichloroethane was added dropwise at 60° C. to a solution of 6 g of 3-methyl-4-oxo-2-phenyl-4H-1-benzopyran-8-carbonyl chloride in 22 ml of 1,2-dichloroethane. The reaction mixture was refluxed for 16 hours, and then cooled to ambient temperature and poured into cold 0.5N sodium hydroxide solution. Water and dichloromethane were added. The organic phase was separated off, washed with aqueous sodium chloride solution and dried on anhydrous sodium sulfate. The solvents were evaporated off and the oily residue was purified by flash chromatography on silica gel, eluting with petroleum ether:ethyl acetate 85:15. The collected fractions were evaporated to dryness in vacuo and the residue was dissolved in ethanol. Excess ethanolic hydrogen chloride was added to give 6.71 g of the title compound, m.p. 203°–204° C.

Example 11

8-{3-[4-(2-methoxyphenyl)-1-piperazinyl]propylcarbamoyl}-3-methyl-4-oxo-2-phenyl-4H-1-benzopyran dihydrochloride hemihydrate Fl'-Y3-$(CH_2)_3$-B1$(OCH_3)$ A mixture of 6.28 g of 1-(2-methoxyphenyl)-piperazine and 5.34 g of Intermediate XXXVII was heated at 180° C. for 5 hours. After cooling, the dark mass was purified by flash chromatography on silica gel, eluting with dichloromethane:methanol 100:3. The fractions containing the title compound were pooled. The solvents were removed in vacuo and the residue was dissolved in boiling ethanol. The solution was filtered, acidified with ethanolic hydrogen chloride, and stood overnight at 20°–25° C. The crude product was collected by filtration and crystallized from ethanol to give 5 g of the title compound, m.p. (177) 182°–186° C.

Example 12

8-{3-[4-(2-methoxyphenyl)-1-piperazinyl]propylcarbamoyl}-3-methyl-4-oxo-2-phenyl-4H-1-benzopyran dihydrochloride hemihydrate Fl'-Y3-(CH$_2$)$_3$-B1(OCH$_3$)

A solution of 4.48 g of 3-methyl-4-oxo-2-phenyl-4H-1-benzopyran-8-carbonyl chloride in 40 ml of chloroform was added dropwise over a period of 10 minutes at ambient temperature to a solution of 3.74 g of 3-[4-(2-methoxyphenyl)-1-piperazinyl]propylamine (prepared as in British Patent No. 2,161,807) and 1.97 g of triethylamine in 50 ml of chloroform. After stirring for 2 hours, the solution was washed first with 0.5N hydrochloric acid, secondly with a saturated aqueous sodium bicarbonate solution and finally with water. The chloroform solution was dried on anhydrous sodium sulfate and the solvent was evaporated off in vacuo. The residue was worked up as described in Example 11 to give 6.67 g of the title compound, m.p. (177) 182°–186° C. This represents an alternative route to the product of Example 11.

The following salts were also prepared:
monohydrochloride hydrate, m.p. 151°–154° C.,
monomethanesulfonate, m.p. 162°–164° C., and
(±)-hemimalate hydrate, m.p. 110°–112° C.

This example has described the condensation of the amine, 3-[4-(2-methoxyphenyl)-1-piperazinyl]-propylamine, with the carbonyl chloride, 3-methyl-4-oxo-2-phenyl-4H-1-benzopyran-8-carbonyl chloride. It should be noted that the amine can be condensed with the corresponding free acid or the corresponding ethyl ester by heating equimolar amounts thereof with or without a solvent. If a solvent is used, a high boiling point hydrophilic or hydrophobic solvent is appropriate. The amine can also be condensed at room temperature with an equimolar amount of the corresponding free acid in the presence of N,N'-dicyclohexylcarbodiimide and 4-dimethylaminopyridine in a solvent such as dichloromethane, chloroform, tetrahydrofuran, or dimethylformamide.

Example 13

8-{2-[4-(2-methoxyphenyl)-1-piperazinyl]ethylcarbamoyl}-3-methyl-4-oxo-2-phenyl-4H-1-benzopyran monohydrochloride hemihydrate Fl'-Y3-(CH$_2$)$_2$-B1(OCH$_3$)

The title compound was prepared by the method described in Example 16, but using Intermediate XIV instead of Intermediate XV and heating at 55°–60°C. for 32 hours. Also, work up was varied as follows. After collecting the base by filtration, purification was by flash chromatography on silica gel, eluting with chloroform:methanol 100:0.5 and then 100:1. The fractions containing the title compound were pooled and the solvents were removed in vacuo. The residue was crystallized from ethanol. After filtration, the solids were taken up in boiling water and sufficient dilute hydrochloric acid was added to effect solution. The crystalline salt separated on cooling and was collected by suction filtration. m.p. 119°–123° C.

Example 14

8-{3-[2-(2-methoxyphenoxy)-ethylamino]propylcarbamoyl}-3-methyl-4-oxo-2-phenyl-4H-1-benzopyran hydrochloride -Fl'-Y3-(CH$_2$)$_3$-B7(OCH$_3$,H,2)

Operating as described in Example 11, but using 2-(2-methoxyphenoxy)-ethylamine (prepared according to Augstein, J. et al., J. Med. Chem. 8: 356, 1965) instead of 1-(2-methoxyphenyl)-piperazine, heating for 2 hours instead of 5 hours, and using dichloromethane:methanol 100:5 as eluant, the title compound was obtained, m.p. 200°–202° C. (ethanol).

Example 15

8-[3-(4-phenyl-1-piperazinyl)-propylcarbamoyl]-3-methyl-4-oxo-2-phenyl-4H-1-benzopyran monohydrochloride hemihydrate Fl'-Y3-(CH$_2$)$_3$-B1(H)

Operating as described in Example 11, but using 1-phenylpiperazine instead of 1-(2-methoxyphenyl)-piperazine and heating for 2 hours instead of 5 hours, and using dichloromethane:methanol 100:4 as eluant, the title compound was obtained. m.p. (251) 255°–258° C. with decomposition (87% ethanol).

Example 16

8-{N-methyl-2-[4-(2-methoxyphenyl)-1-piperazinyl]-ethylcarbamoyl}-3-methyl-4-oxo-2-phenyl-4H-1-benzopyran monohydrochloride Fl'-Y4-(CH$_2$)$_2$-B1(OCH$_3$)

A mixture of 3.56 g of Intermediate XV, 2.35 g of 1-(2-methoxyphenyl)-piperazine, 2.76 g of anhydrous potassium carbonate and 1.66 g of potassium iodide in 25 ml of dimethylformamide was stirred at 100° C. for 6 hours. After cooling, the solvent was removed in vacuo and the residue was taken up in 50 ml of water, stirred for 1 hour at room temperature, collected by filtration, washed with water and crystallized from 95% ethanol in the presence of a small amount of activated charcoal (for decoloring). The base was dissolved in 105 ml of boiling 0.086N hydrochloric acid. After cooling, the crystallized salt was collected by filtration, giving 4.3 g of the title compound (m.p. 201°–203° C.).

Example 17

8-{1-Hydroxy-2-[4-(2-methoxyphenyl)-1-piperazinyl]-ethyl}-3-methyl-4-oxo-2-phenyl-4H-1-benzopyran hydrochloride Fl'-Y6-CH$_2$-B1(OCH$_3$)

1.36 g of sodium borohydride was added portionwise at 0 to +5° C. to a solution of 15.5 g of the compound prepared in Example 1 in 1500 ml of methanol. After stirring for 90 minutes at 0 to +5° C., 3N hydrochloric acid was added in order slightly to acidify the reaction mixture, which was then stripped in vacuo. The residue was shaken with 2N aqueous sodium hydroxide solution and extracted with chloroform. The organic layer was dried on anhydrous sodium sulfate/calcium chloride, filtered, acidified with ethanolic hydrogen chloride and stripped in vacuo. After washing with diethyl ether, the crude product was crystallized from ethanol to give 9.5 g of title compound, m.p. 248°–249° C.

Example 18

8-{1-Hydroxy-2-[4-(2-methylphenyl)-1-piperazinyl]-ethyl}-3-methyl-4-oxo-2-phenyl-4H-1-benzopyran hydrochloride Fl'-Y6-CH$_2$-B1(CH$_3$)

This compound was prepared according to Example 17, but starting from the compound prepared in Example 2 rather than that prepared in Example 1. m.p. 257°–258° C. (ethanol).

Example 19

8-{1-Hydroxy-2-[4-(2-ethoxyphenyl)-1-piperazinyl]-ethyl}-3-methyl-4-oxo-2-phenyl-4H-1-benzopyran hydrochloride Fl'-Y6-CH$_2$-B1(OC$_2$H$_5$)

This compound was prepared according to Example 17, but starting from the compound prepared in Example 3 rather than that prepared in Example 1. m.p. 241°–242° C. (methanol).

Example 20

8-{1-Hydroxy-3-[4-(2-methoxyphenyl)-1-piperazinyl]-propyl}-3-methyl-4-oxo-2-phenyl-4H-1-benzopyran hydrochloride Fl'-Y6-$(CH_2)_2$-B1$(OCH_3)$ This compound was prepared according to Example 17, but starting from the compound prepared in Example 4 rather than that prepared in Example 1. The crude base was purified by flash chromatography (silica gel, eluant-ethyl acetate: chloroform 4:1). The fractions containing the pure base were pooled, acidified with ethanolic hydrogen chloride and stripped in vacuo. The residue was crystallized from ethanol. m.p. (126) 156°–160° C.

Example 21

8-{1-hydroxy-4-[4-(2-methoxyphenyl)-1-piperazinyl]-butyl}-3-methyl-4-oxo-2-phenyl-4H-1-benzopyran hydrochloride monohydrate Fl'-Y6-$(CH_2)_3$-B1$(OCH_3)$ A solution of 3.04 g of Intermediate XXXVIII and 2.45 g of 1-(2-methoxyphenyl)-piperazine in 21 ml of anhydrous dimethylformamide was stirred for 5 hours at ambient temperature. A further 1.22 g of 1-(2-methoxyphenyl)-piperazine was added, and the mixture was stirred for 4 hours, poured into 300 ml of water, and extracted with ethyl acetate. The combined organic extracts were washed with aqueous sodium bicarbonate solution and then with aqueous sodium chloride solution, and evaporated to dryness in vacuo. The residue was purified by flash chromatography on silica gel, eluting with ethyl acetate:methanol 95:5. The collected fractions were stripped on a rotary evaporator, and the residue was dissolved in 0.81M ethanolic hydrogen chloride and stripped again in vacuo. The solid residue was crystallized from water:ethanol 9:1 to give 2.43 g of the title compound, m.p. 144°–146° C.

Example 22

8-{1-ethoxy-2-[4-(2-methoxyphenyl)-1-piperazinyl]-ethyl}-3-methyl-4-oxo-2-phenyl-4H-1-benzopyran hydrochloride Fl'-Y7$(C_2H_5)$-$CH_2$-B1$(OCH_3)$ 6 ml of anhydrous dimethylsulfoxide was added to 6.55 g of sodium hydride (50% in mineral oil, repeatedly washed with hexane) under nitrogen. A solution of 3 g of the compound prepared in Example 17 in 50 ml of anhydrous dimethylsulfoxide was added to the mixture at 20°–25° C. After stirring for 1 hour at 20° C., 0.66 g of ethyl bromide was added. The reaction mixture was stirred for an additional 20 minutes at the same temperature and then poured into iced water. The crude product obtained after suction filtration was purified by flash chromatography (silica gel, eluant-chloroform:ethyl acetate 8:2). The fractions containing the pure title compound were pooled, acidified with ethanolic hydrogen chloride, and stripped in vacuo. The residue was crystallized from chloroform:diethyl ether and dried in vacuo at 140° C. to give 1.6 g of the title compound, m.p. (155) 209° C.

Example 23

8-{N-methyl-2-[4-(2-methoxyphenyl)-1-piperazinyl]-ethylaminomethyl}-3-methyl-4-oxo-2-phenyl-4H-1-benzopyran dihydrochloride hemihydrate Fl'-Y16-$(CH_2)_2$-B1$(OCH_3)$ A mixture of 5.2 g of Intermediate XXVII, 3.1 g of 1-(2-methoxyphenyl)-piperazine and 2.2 g of anhydrous potassium carbonate in 50 ml of dimethylformamide was stirred at 70° C. for 7 hours. After cooling to 20°–25° C., the reaction mixture was poured into 500 ml of water, and extracted with dichloromethane. The organic phase was washed with water and dried on anhydrous sodium sulfate. The solvent was removed in vacuo. The residue was purified by flash chromatography on silica gel, eluting with ethyl acetate:petroleum ether 98:2. The title compound was obtained by salification with ethanolic hydrogen chloride. m.p. 217°–219° C.

Example 24

8-{N-acetyl-2-[4-(2-methoxyphenyl)-1-piperazinyl]-ethylaminomethyl)-3-methyl-4-oxo-2-phenyl-4H-1-benzopyran hydrochloride Fl'-Y17-$(CH_2)_2$-B1$(OCH_3)$ A mixture of 5 g of Intermediate XXXIII and 5.3 g of 1-(2-methoxyphenyl)-piperazine in 75 ml of dimethylformamide was stirred at 95° C. for 2 hours. After cooling to 20°–25° C., the reaction mixture was poured into 200 ml of water, made alkaline with potassium carbonate and extracted with ethyl acetate. The organic phase was washed with water and dried on anhydrous sodium sulfate. The solvent was removed in vacuo. The residue was purified by flash chromatography on silica gel, eluting with dichloromethane:methanol 100:0.2. Salification of the pure base with ethanolic hydrogen chloride and recrystallization from methanol gave 4.4 g of the title compound, melting at (200) 227°–228° C. and containing one equivalent of methanol.

Example 25

8-[4-(2-methoxyphenyl)-1-piperazinylacetamidomethyl]-3-methyl-4-oxo-2-phenyl-4H-1-benzopyran hydrochloride Fl'-Y19-$CH_2$-B1$(OCH_3)$ A mixture of 3.42 g of Intermediate XXXII, 2.74 g of 1-(2-methoxyphenyl)-piperazine and 0.71 g of anhydrous potassium carbonate in 34 ml of anhydrous dimethylformamide was stirred at 0° C. for 2 hours. The reaction mixture was poured into water and filtered under suction. The resultant solid was purified by flash chromatography on silica gel, eluting with ethyl acetate:petroleum ether 6:4. The collected fractions were evaporated to dryness in vacuo, and the residue was crystallized from ethyl methyl ketone. The base obtained was treated in ethanolic solution with a molar equivalent of aqueous 2.25N hydrochloric acid to give the title compound, p.p. 168°–170° C.

Example 26

8-{N-methyl-[4-(2-methoxyphenyl)-1-piperazinyl]-acetamido-methyl}-3-methyl-4-oxo-2-phenyl-4H-1-benzopyran hydrochloride hydrate Fl'-Y20-$CH_2$-B1$(OCH_3)$ A mixture of 5 g of Intermediate XXXI, 2.9 g of 1-(2-methoxyphenyl)-piperazine and 2 g of anhydrous potassium carbonate in 50 ml of dimethylformamide was stirred at 20°–25° C. for 3 hours. The reaction mixture was then poured into 500 ml of water and extracted with dichloromethane. The organic phase was washed with water and dried on anhydrous sodium sulfate. The solvent was removed in vacuo. The residue was purified by flash chromatography on silica gel, eluting with ethyl acetate:petroleum ether 6:4, and crystallized from acetone to give 3.6 g of the base of the title compound, melting at 144°–145° C. The base was dissolved in etha-

Example 27

8-{2-[4-(2-methoxyphenyl)-1-piperazinyl]ethoxymethyl}-3-methyl-4-oxo-2-phenyl-4H-1-benzopyran dihydrochloride Fl'-Y23-(CH$_2$)$_2$-B1(OCH$_3$)

A mixture of 4 g of Intermediate XVIII, 2.4 g of 1-(2-methoxyphenyl)-piperazine, 1.96 g of potassium iodide and 1.65 g of anhydrous potassium carbonate in 40 ml of anhydrous dimethylformamide was stirred at 90° C. for 7 hours. After cooling to ambient temperature, the mixture was poured into water and extracted with dichloromethane. The combined extracts were washed with aqueous sodium chloride solution, dried on anhydrous sodium sulfate and evaporated to dryness in vacuo. The residue was crystallized from ethyl acetate and the collected crystals were dissolved in ethanol and treated with excess ethanolic hydrogen chloride to give 5.21 g of the title compound, m.p. 199°–201° C.

Example 28

8-{2-[2-(2-ethoxyphenoxy)-ethylamino]ethoxymethyl}-3-methyl-4-oxo-2-phenyl-4H-1-benzopyran hydrochloride Fl'-Y23-(CH$_2$)$_2$-B7(OC$_2$H$_5$,H,H$_{1,2}$).

Operating as described in Example 27, but using 2-(2-ethoxyphenoxy)-ethylamine in place of 1-(2-methoxyphenyl)piperazine and including a purification step of flash chromatography on silica gel eluted with ethyl acetate:methanol 97:3, 4.25 g of the title compound was obtained. m.p. 191°–193° C.

Example 29

8-{2-[4-(2-methoxyphenyl)-1-piperazinyl]ethylthiomethyl}-3-methyl-4-oxo-2-phenyl-4H-1-benzopyran hydrochloride Fl'-Y24-(CH$_2$)$_2$-B1(OCH$_3$) -

2.5 g of potassium carbonate, 2.13 g of potassium iodide and 3.15 g of 1-(2-methoxyphenyl)-piperazine were added to a solution of 5 g of Intermediate XXI in 50 ml of dimethylformamide, and the mixture was stirred at 90° C. for 4.5 hours. After cooling to ambient temperature, the reaction mixture was poured into 450 ml of water and extracted with ethyl acetate. The organic extracts were washed with water, dried on anhydrous sodium sulfate and evaporated to dryness in vacuo. A solution of the residue in acetone was treated with a molar equivalent of 3.8N hydrogen chloride in diethyl ether, filtered and recrystallized from ethanol to yield 6.15 g of the title compound, m.p. (218) 223°–224° C.

Example 30

8-{2-[4-(2-methoxyphenyl)-1-piperazinyl]ethylsulfinylmethyl}-3-methyl-4-oxo-2-phenyl-4H-1-benzopyran dihydrochloride hemihydrate-Fl'-Y25-(CH$_2$)$_2$-B1(OCH$_3$)

The title compound was prepared by the method described in Example 29, using Intermediate XXVI instead of Intermediate XXI and stirring for 2.5 hours rather than for 4.5 hours. After the usual work up, the residue was purified by flash chromatography on silica gel, eluting with ethyl acetate:methanol 97:3. The collected fractions were acidified with excess ethanolic hydrogen chloride, evaporated to dryness in vacuo. The residue was crystallized from ethanol, giving 5.2 g of the title compound, m.p. 170°–172° C. This compound contains 1 equivalent of ethanol.

Example 31

8-{2-[4-(2-methoxyphenyl)-1-piperazinyl]ethylsulfonylmethyl}-3-methyl-4-oxo-2-phenyl-4H-1-benzopyran hydrochloride Fl'-Y26-(CH$_2$)$_2$-B1(OCH$_3$)

A mixture of 4.5 g of Intermediate XXV, 2.36 g of 1-(2-methoxyphenyl)-piperazine and 0.84 g of potassium carbonate in 45 ml of anhydrous dimethylformamide was stirred at ambient temperature for 2.5 hours. The reaction mixture was poured into 300 ml of water and filtered under suction, washing with water. The solid base was crystallized from ethanol and had a melting point of 143°–146° C. The crystals were dissolved in 1,2-dichloroethane and acidified with ethanolic hydrogen chloride. 4.4 g of the title compound, m.p. 229°–2330C., was obtained by recrystallization from methanol:water 1:3.5.

Example 32

8-{2-[4-(2-methoxyphenyl)-1-piperazinyl]ethylamino}-3-methyl-4-oxo-2-phenyl-4H-1-benzopyran dihydrochloride Fl'-Y29-(CH$_2$)$_2$-B1(OCH$_3$)

A solution of 3.7 g of Intermediate XXIII in 10 ml of dimethylformamide was added dropwise at 0° C to a suspension of 0.9 g of sodium hydride (50% in mineral oil) in 9 ml of dimethylformamide. The cooling bath was removed, and after 30 minutes at 20°–25° C. a solution of 4.1 g of 1-(2-chloroethyl)-4-(2-methoxyphenyl)-piperazine in 10 ml of dimethylformamide was added. The mixture was stirred at 90° C. for 5 hours and then cooled to 20°–25° C. A further addition of 0.25 g of sodium hydride (50% in mineral oil) followed by 1.36 g of 1-(2-chloroethyl)-4-(2-methoxyphenyl)-piperazine in 5 ml of dimethylformamide was made. The mixture was stirred at 90° C. for 8 hours and again cooled to 20°–25° C. 200 ml of water was cautiously added, and the mixture was extracted with ethyl acetate. The organic layer was washed with water and dried on anhydrous sodium sulfate. The solvent was evaporated off in vacuo and the residue was purified by flash chromatography on silica gel, eluting with n-hexane: ethyl acetate 3:2. This gave a mixture of the base of the title compound and the corresponding N-trifluoroacetyl compound.

3.8 g of this mixture was dissolved in 35 ml of ethanol and 35 ml of dimethylsulfoxide. To this solution, 0.55 g of sodium borohydride was added portionwise at 20°–25° C. The mixture was stirred for 3 hours at this temperature, and then poured into 200 ml of water and extracted with ethyl acetate. The organic extracts were washed with water, dried on anhydrous sodium sulfate and evaporated to dryness in vacuo. The residue was dissolved in dichloromethane. 2 equivalents of ethanolic hydrogen chloride were added to give the title compound, which was recrystallized from ethanol. Yield 3.8 g, m.p. 231°–234° C.

Example 33

8-{3-[4-(2-methoxyphenyl)-1-piperazinyl]propylamino}-3-methyl-4-oxo-2-phenyl-4H-1-benzopyran hydrochloride 2.75-hydrate Fl'-Y29-(CH$_2$)$_3$-B1(OCH$_3$)

Using 1-(3-chloropropyl)-4-(2-methoxyphenyl)-piperazine instead of 1-(2-chloroethyl)-4-(2-methoxyphenyl)-piperazine, but otherwise operating as described in Example 32, the title compound was obtained. m.p. 206°–208° C. (10% ethanol).

--- nol and 8N hydrochloric acid and water were added, yielding the title compound, m.p. 218°–220° C. after drying at 100° C. in vacuo.

Example 34

8-{4-[4-(2-methoxyphenyl)-1-piperazinyl]butylamino}-3-methyl-4-oxo-2-phenyl-4H-1-benzopyran hydrochloride hemihydrate Fl'-Y29-(CH$_2$)$_4$-B1(OCH$_3$)

A mixture of 4.5 g of Intermediate XXXIX, 3.9 g of 8-amino-3-methyl-4-oxo-2-phenyl-4H-1-benzopyran, 8.3 g of sodium triacetoxyborohydride and 3.4 ml of acetic acid in 40 ml of 1,2-dichloroethane was stirred for 6 hours at 20°–25° C. 15 ml of 5% aqueous sodium bicarbonate solution was then added, and the mixture was stirred for 10 minutes. The mixture was then made alkaline by addition of 0.5N sodium hydroxide solution and extracted with dichloromethane. The organic extracts were washed with water and dried on anhydrous sodium sulfate. The solvent was evaporated off in vacuo and the residue was purified by flash chromatography on silica gel, eluting with ethyl acetate:petroleum ether 9:1. The base obtained was dissolved in dichloromethane and 1 equivalent of ethanolic hydrogen chloride was added. After removing the solvent in vacuo, the residue was crystallized from 50% ethanol to give 1.6 g of the title compound, m.p. (140) 151°–153° C.

Example 35

8-{N-methyl-3-[4-(2-methoxyphenyl)-1-piperazinyl]propylamino}-3-methyl-4-oxo-2-phenyl-4H-1-benzopyran hydrochloride hemihydrate Fl'-Y30-(CH$_2$)$_3$-B1(OCH$_3$)

A mixture of 4 g of the compound prepared in Example 33, in the form of its base, 4.35 ml of 37% aqueous formaldehyde and 1.15 g of sodium cyanoborohydride in 25 ml of acetonitrile was stirred at 20°–25° C., maintaining the pH in the range 5–6 by the addition of acetic acid during the reaction. After 4 hours the solvent was evaporated off in vacuo. 80 ml of ethyl acetate and 200 ml of ice cooled 1N sodium hydroxide solution were added to the residue. The organic phase was washed with water, dried on anhydrous sodium sulfate and evaporated to dryness in vacuo. The residue was purified by flash chromatography on silica gel, eluting with ethyl acetate:petroleum ether 3:1. The pure base which was obtained was dissolved in diethyl ether. 1 equivalent of ethanolic hydrogen chloride was added and the solvent was removed in vacuo. The residue was crystallized from water to give 2 g of the title compound, m.p. 186°–187° C.

Example 36

8-{N-acetyl-3-[4-(2-methoxyphenyl)-1-piperazinyl]propylamino}-3-methyl-4-oxo-2-phenyl-4H-1-benzopyran hydrochloride hydrate Fl'-Y31-(CH$_2$)$_3$-B1(OCH$_3$)

A mixture of 4.8 g of the compound prepared in Example 33, in the form of its base, 2.8 ml of acetic anhydride and 33 ml of pyridine was stirred at 80° C. for 4 hours. After cooling to 20°–25° C., the reaction mixture was poured into 200 g of iced water, acidified with 10N hydrochloric acid and extracted with dichloromethane. The organic extracts were washed with water, dried on anhydrous sodium sulfate and evaporated to dryness in vacuo. The residue was purified by flash chromatography on silica gel, eluting with ethyl acetate:methanol 95:5. The pure base which was obtained was dissolved in dichloromethane. 1 equivalent of ethanolic hydrogen chloride was added and the solvent was removed in vacuo. The residue was crystallized from acetonitrile to give 3 g of the title compound containing 0.33 equivalents of acetonitrile, m.p. 208.5°–210.5° C.

Example 37

8-{3-[4-(2-methoxyphenyl)-1-piperazinyl]propionamido}-3-methyl-4-oxo-2-phenyl-4H-1-benzopyran hydrochloride Fl'-Y33-(CH$_2$)$_2$-B1(OCH$_3$)

A mixture of 3.97 g of Intermediate X and 3.07 g of 1-(2-methoxyphenyl)-piperazine in 40 ml of dimethylformamide was stirred at 60° C. for 6 hours. The reaction mixture was then cooled to ambient temperature and poured into water. Following extraction with dichloromethane, the organic phase was washed with water and dried on anhydrous sodium sulfate. The solvent was removed in vacuo. The crude residue was crystallized from ethanol to give the base of the title compound, which was then dissolved in hot ethanol. 1 molar equivalent of 0.81M ethanolic hydrogen chloride was added to the solution. 4 g of the title compound, m.p. 255°–257° C., was obtained.

Example 38

8-{2-[4-(2-methoxyphenyl)-1-piperazinyl]ethylureido}-3-methyl-4-oxo-2-phenyl-4H-1-benzopyran methanesulfonate Fl'-Y35-(CH$_2$)$_2$-B1(OCH$_3$)

A mixture of 3.34 g of Intermediate XLIV and 7.22 g of 1-(2-methoxyphenyl)-piperazine was stirred at 100° C. for 5 hours. An additional 1.8 g of 1-(2-methoxyphenyl)-piperazine was then added and stirring was continued for a further 2 hours at 100° C. After cooling to ambient temperature, the reaction mixture was poured into water and extracted with ethyl acetate. The organic phase was washed with aqueous sodium hydroxide solution, dried on anhydrous sodium sulfate and evaporated to dryness in vacuo. The crude residue was purified by flash chromatography on silica gel, eluting with ethyl acetate: methanol 98:2. The collected fractions were evaporated to dryness in vacuo and crystallized from water:ethanol 4:6. The crystals were redissolved in dichloromethane and treated with 1 molar equivalent of methanesulfonic acid. The crude methanesulfonate obtained by evaporation in vacuo was crystallized from ethyl acetate:ethanol 1:1 to yield 2.35 g of the title compound, melting at 191°–193° C.

Example 39

8-{2-[4-(2-methoxyphenyl)-1-piperazinyl]ethoxy}-3-methyl-4-oxo-2-phenyl-4H-1-benzopyran hydrochloride hydrate Fl'-Y37-(CH$_2$)$_2$-B1(OCH$_3$)

A mixture of 6.61 g of the Intermediate XI, 8.34 g of 1-(2-methoxyphenyl)-piperazine and 1.26 g of sodium iodide in 70 ml of dimethylformamide was stirred at 80° C. for 17 hours. After cooling to 20°–25° C., the reaction mixture was poured into 600 ml of water, made alkaline with 5% aqueous sodium bicarbonate and extracted with dichloromethane. The organic extracts were washed with aqueous sodium chloride solution, dried on anhydrous sodium sulfate and evaporated to dryness in vacuo. The residue was purified by flash chromatography on silica gel, eluting with dichloromethane:methanol 99:1, then 98:2. The fractions containing the base of the title compound were pooled, and the solvent was removed in vacuo. The residue was dissolved in ethanol and ethanolic hydrogen chloride was added. The title compound crystallized and was collected by suction filtration. It was recrystallized from 95% ethanol. Yield 6.5 g, m.p. 224°–225° C.

| Elemental analysis: | | | | | |
|---|---|---|---|---|---|
| Found %: | C = 66.38, | H = 6.34, | N = 5.35, | Cl = 6.76, | $H_2O$ = 3.35 |
| Calculated %: | 66.34, | 6.14, | 5.33, | 6.75, | 3.43 |

NMR Spectrum at 60 MHz ($CDCl_3$—$CD_3OD$)

| | | |
|---|---|---|
| 7.8–7.1 | (m, 8H) | aromatic protons of the benzopyran ring |
| 7.1–6.6 | (m, 4H) | aromatic protons of the 2-methoxyphenyl group |
| 4.8–4.4 | (m, 2H) | $OCH_2$ |
| 4.4–4.1 | (m, 3H) | $H_2O$ and $N^+H$ |
| 3.9–3.0 | (m, 10H) | 5 × $CH_2N$ |
| 3.8 | (s, 3H) | $OCH_3$ |
| 2.1 | (s, 3H) | $CH_3$ |

Example 40

8-{3-[4-(2-methoxyphenyl)-1-piperazinyl]propoxy}-3-methyl-4-oxo-2-phenyl-4H-1-benzopyran dihydrochloride Fl'-Y37-$(CH_2)_3$-B1($OCH_3$)

This compound was prepared by the method described in Example 39, but using Intermediate IX instead of Intermediate XI. Purification by flash chromatography was omitted as unnecessary in this case. m.p. 226°–227° C.

Example 41

8-{4-[4-(2-methoxyphenyl)-1-piperazinyl]butoxy}-3-methyl-4-oxo-2-phenyl-4H-1-benzopyran dihydrochloride Fl'-Y37-$(CH_2)_4$-B1($OCH_3$)

A mixture of 7.75g of Intermediate XVI, 4.7 g of 1-(2-methoxyphenyl)-piperazine, 3.3 g of potassium iodide and 2.8 g of anhydrous potassium carbonate in 78 ml of dimethylformamide was stirred at 75° C. for 2 hours. After cooling to 20°–25° C., the reaction mixture was poured into 600 ml of water and extracted with dichloromethane. The organic extracts were washed with water and dried on anhydrous sodium sulfate, and the solvent was then evaporated off in vacuo. The residue was purified by column chromatography on silica gel, eluting with ethyl acetate. The pure title compound thus obtained as its base was transformed into its dihydrochloride by treatment with ethanolic hydrogen chloride. After crystallization from ethanol, 6.5 g of title compound was obtained. m.p. 217°–219° C.

Example 42

8-{5-[4-(2-methoxyphenyl)-1-piperazinyl]pentyloxy}-3-methyl-4-oxo-2-phenyl-4H-1-benzopyran hydrochloride Fl'-Y37-$(CH_2)_5$-B1($OCH_3$)

This compound was prepared by the method described in Example 41, but using Intermediate XVII instead of Intermediate XVI. m.p. 173° C. (ethanol). The corresponding base melts at 117°–118° C. (ethanol).

Example 43

8-{3-[4-(2-methoxyphenyl)-1-oxo-1-piperazinyl]propoxy)-3-methyl-4-oxo-2-phenyl-4H-1-benzopyran 1.75-hydrate Fl'-Y37-$(CH_2)_3$-B1($OCH_3$-1-oxide)

2.93 g of magnesium monoperoxyphthalate in 10 ml of water was added dropwise at −15° C. to a solution of 4.34 g of the compound prepared in Example 40 and 0.1 g of benzyl(triethyl) ammonium chloride in 20 ml of dichloroethane and 20 ml of methanol. The mixture was stirred for 2 hours at 0° C. and then warmed to ambient temperature. It was poured into water and made basic by addition of aqueous sodium hydroxide solution. Extraction with dichloromethane gave, after the usual work up, a solid which was purified by flash chromatography, eluting with dichloromethane:methanol 9:1. The collected fractions containing the pure compound were evaporated to dryness in vacuo and the residue was crystallized from acetonitrile to give 0.5 g of the title compound, m.p. 89°–92° C.

Example 44

8-{2-[2-(2,6-dimethoxyphenoxy)-ethylamino]ethoxy}-3-methyl-4-oxo-2-phenyl-4H-1-benzopyran hydrochloride Fl'-Y37-$(CH_2)_2$-B7($OCH_3$,$OCH_3$,$H_1$,$H_2$,2)

A mixture of 4.5 g of Intermediate XII, 3.7 g of triphenyl phosphine and 2.85 g of 2,6-dimethoxyphenoxyacetaldehyde (prepared as per Nelson, W. L. et al., *J. Med. Chem.* 22: 1125, 1979) in 45 ml of benzene was stirred at 20°–25° C. for 18 hours and at reflux for 5 hours. The solvent was evaporated off in vacuo and the residue was dissolved in 80 ml of anhydrous methanol. 3Å-at 0° C. The mixture was stood for 1 hour at 0° C. and for 1 hour at 20°–25° C., and then poured into iced water and extracted with dichloromethane. The organic extracts were washed with water and dried on anhydrous sodium sulfate. The solvent was removed in vacuo and the residue was purified by flash chromatography on silica gel, eluting with dichloromethane:methanol 49:1. The base obtained was treated with ethanolic hydrogen chloride. After crystallization from ethanol, the title compound was obtained. Yield 40%, m.p. 200°–202° C.

Example 45

8-{2-hydroxy-3-[4-(2-methoxyphenyl)-1-piperazinyl]propoxy}-3-methyl-4-oxo-2-phenyl-4H-1-benzopyran hydrochloride Fl'-Y37-$CH_2$-CH(OH)-$CH_2$-B1($OCH_3$)

A solution of 3.7 g of Intermediate XL and 4.64 g of 1-(2-methoxyphenyl)-piperazine in 40 ml of dimethylformamide was stirred at 80° C. for 3 hours. After cooling to 20°–25° C., the reaction mixture was poured into 400 ml of water and extracted with dichloromethane. The aqueous phase was made alkaline with 1N sodium hydroxide solution and extracted with ethyl acetate. The combined organic extracts were washed with water and dried on anhydrous sodium sulfate. The solvents were evaporated off in vacuo. The residue was purified by flash chromatography on silica gel, eluting with ethyl acetate. The fractions containing the title compound in the form of its base were pooled, and stripped in vacuo. The residue was dissolved in dichloromethane and one equivalent of ethanolic hydrogen chloride was added. The solvents were removed in vacuo and the residue was crystallized from ethanol. 5 g of the title compound containing one molar equivalent of ethanol were obtained. m.p. (122) 126°–128° C. with decomposition.

Example 46

8-{3-[4-(2-methoxyphenyl)-1-piperazinyl]propylthio}-3-methyl-4-oxo-2-phenyl-4H-1-benzopyran Fl'-Y38-(CH$_2$)$_3$-B1(OCH$_3$)

A mixture of 4.4 g of Intermediate XXXIV, 2.5 g of 1-(2-methoxyphenyl)-piperazine, 1 g of potassium iodide and 1.8 g of anhydrous potassium carbonate in 40 ml of dimethylformamide was stirred at 100° C. for 3 hours. After cooling to 20°–25° C., the reaction mixture was poured into 350 ml of water and extracted with dichloromethane. The organic extracts were washed with water and dried on anhydrous sodium sulfate, and the solvent was then evaporated off in vacuo. The residue was purified by column chromatography on silica gel, eluting with ethyl acetate: petroleum ether 3:2, and by crystallization from ethanol, yielding 3.9 g of the title compound, m.p. (70) 96°–99° C.

Example 47

8-{3-[4-(2-methoxyphenyl)-1-piperazinyl]propylsulfonyl}-3-methyl-4-oxo-2-phenyl-4H-1-benzopyran hydrochloride Fl'-Y40-(CH$_2$)$_3$-B1(OCH$_3$)

A solution of 3.8 g of Intermediate XXXV and 4 g of 1-(2-methoxyphenyl)-piperazine in 40 ml of dimethylformamide was heated at 60° C. for 7 hours. After cooling to 20°–25° C., the reaction mixture was poured into 500 ml of water and extracted with dichloromethane. The organic extracts were washed with water and dried on anhydrous sodium sulfate, and the solvent was then evaporated off in vacuo. The residue was purified by flash chromatography on silica gel, eluting with ethyl acetate:petroleum ether 1:1. The base of the title compound was obtained. It was dissolved in ethanol and one equivalent of ethanolic hydrogen chloride was added to give 4.5 g of the title compound, m.p. (215) 226°–228° C.

Example 48

8-{2-[4-(2-methoxyphenyl)-1-piperazinyl]ethylsulfamyl}-3-methyl-4-oxo-2-phenyl-4H-1-benzopyran hydrochloride Fl'-Y41-(CH$_2$)$_2$-B1(OCH$_3$)

A solution of 4.5 g of Intermediate XLII and 3.8 g of 1-(2-methoxyphenyl)-piperazine in 40 ml of dimethylformamide was heated at 70° C. for 7 hours. After cooling to 20°–25° C., the reaction mixture was poured into 150 ml of water and extracted with dichloromethane. The organic solution was washed with water and dried on anhydrous sodium sulfate, and the solvent was then evaporated off in vacuo. The residue was purified by flash chromatography on silica gel, eluting with ethyl acetate:petroleum ether 3:7, and the title compound was obtained by salification with ethanolic hydrogen chloride. Yield 2.9 g, m.p. 236°–238° C.

Example 49

8-{N-methyl-2-[4-(2-methoxyphenyl)-1-piperazinyl]-ethylsulfamyl}-3-methyl-4-oxo-2-phenyl-4H-1-benzopyran hydrochloride Fl'-Y42-(CH$_2$)$_2$-B1(OCH$_3$)

The title compound was obtained by the method described in Example 48, but using Intermediate XLI instead of Intermediate XLII. m.p. 194°–198° C. (ethanol).

Example 50

8-{N-aminocarbonyl-3-[4-(2-methoxyphenyl)-1-piperazinyl]propylamino}-3-methyl-4-oxo-2-phenyl-4H-1-benzopyran methanesulfonate hemihydrate Fl'-Y32-(CH$_2$)$_3$-B1(OCH$_3$)

A mixture of 4.06 g of the compound of Example 33 and 1.5 g of potassium cyanate in 42 ml of glacial acetic acid is stirred at 50° C. for 4 hours. The reaction mixture is poured into iced water and made alkaline. The precipitate is collected by suction filtration, dried and purified by flash chromatography using a silica gel column, eluting with ethyl acetate:methanol (98:2). The fractions, containing the title product as a base, are evaporated to dryness in vacuo and an equivalent of methanesulfonic acid is added to the residue dissolved in 30 ml of dichloromethane. The solvent is evaporated off in vacuo and the residue is crystallized from ethanol to give 3.1 g of the title compound (m.p. 157°–160° C., with decomposition). This compound contains one molar equivalent of ethanol.

Example 51

8-{4-[4-(2-methoxyphenyl)-1-piperazinyl]-1-oxobutyl}-3-methyl-4-oxo-2-phenyl-4H-1-benzopyran methanesulfonate Fl'-Y1-(CH$_2$)$_3$-B1(OCH$_3$)

A solution of 1.33 ml of anhydrous dimethylsulfoxide in 9 ml of dichloromethane is added at −70° C. to a solution of 0.74 ml of oxalyl chloride in 6 ml of dichloromethane. After stirring at −70° C. for 15 minutes, a solution of 2.8 g of the compound of the Example 21 (as a base) in 14 ml of dichloromethane is added. After 15 minutes at the same temperature, 4.7 ml of anhydrous triethylamine is added and the temperature is raised to −30° C. over a period of 30 minutes. Stirring is continued at −30° C. for another 30 minutes. After letting the temperature rise to 0° C., the mixture is diluted with 120 ml of water and extracted with dichloromethane. The organic phase is washed with water, dried on anhydrous sodium sulphate and evaporated to dryness in vacuo. The residue is purified by flash chromatography in a silica gel column, eluting with ethyl acetate:dichloromethane (9:1). The fractions, containing the title product, are evaporated to dryness in vacuo and one equivalent of methanesulphonic acid is added to the residue dissolved in 30 ml of dichloromethane. The solvent is evaporated off in vacuo and the residue is crystallized from ethanol to give 2.9 g of the title compound (m.p. 194°–195° C.).

Example 52

8-{3-[2-(1,4-benzodioxanyl)methylamino]propylcarbamoyl}-3-methyl-4-oxo-2-phenyl-4H-1-benzopyran methanesulfonate Fl'-Y3-(CH$_2$)$_3$-B8(H,H)

A mixture of 5.56 g of the Intermediate XLIII, as a base, 4.58 g of 2-(4-toluenesulfonyloxymethyl)-1,4-benzodioxane and 1.9 g of anhydrous potassium carbonate in 80 ml of anhydrous dimethylformamide is stirred at 110° C. for 5 hours. The reaction mixture is cooled to ambient temperature, poured into water and extracted with dichloromethane. The organic phase is washed with water, dried on anhydrous sodium sulphate, filtered and evaporated to dryness in vacuo. The residue is purified by flash chromatography using a silica gel column, eluting with ethyl acetate:methanol (95:5). The fractions containing the title product as a base are evaporated to dryness in vacuo and one equivalent of methanesulfonic acid dissolved in ethyl acetate is added to the residue dissolved in ethanol. The crystallized product is filtered and recrystallized from ethanol to give 2.4 g of the title compound (m.p. 172°–174° C.).

Example 53

8-{4-[4-(2-methoxyphenyl)-1-piperazinyl]butyl}-3-methyl-4-oxo-2-phenyl-4H-1-benzopyran methanesulfonate Fl'-Y12-(CH$_2$)$_3$-B1(OCH$_3$)

A solution of 2.8 g of the Intermediate XLVI and 0.13 g of p-toluenesulfonic acid in 150 ml of methanol is refluxed for 5 hours. After cooling to 20°–25° C., 0.8 g of anhydrous potassium carbonate is added and stirring is continued for 3 hours. After filtration, the reaction mixture is evaporated to dryness in vacuo to give 2.5 g of 8-(4,4-dimethoxybutyl)-3-methyl-4-oxo-2-phenyl-4H-1-benzopyran.

NMR CDCl$_3$ (δ) 1.6–1.9 (4H, m, CH$_2$CH$_2$CH$_2$CH$_2$) 2.2 (3H, s, flavone CH$_3$) 2.9 (2H, t, Fl'-CH$_2$) 3.3 (6H, s, 2×OCH$_3$) 4.4 (1H, t, CH(OCH$_3$)$_2$) 7.3 (1H, dd, flavone CH in 6) 7.5–7.8 (6H, m, flavone CH in 7, and 5×phenyl CH) 8.1 (1H, dd, flavone CH in 5)

A solution of 2.5 g of the above compound in 10 ml of water and 30 ml of acetic acid are heated at 50° C. for 2.5 hours. The reaction mixture is cooled to ambient temperature, diluted with iced water, basified with aqueous sodium carbonate, and extracted with chloroform. The organic phase is dried on anhydrous sodium sulphate, filtered and evaporated to dryness in vacuo. The residue is purified by flash chromatography on silica gel, eluting with petroleum ether:ethyl acetate (3:1). 2.1 g of 8-(4-oxobutyl)-3-methyl-4-oxo-2-phenyl-4H-1-benzopyran is obtained (>75% yield) and is used with no further purification in the next step.

NMR CDCl$_3$ (δ) 1.9–2.1 (2H, dd, CH$_2$CH$_2$CH$_2$CHO) 2.2 (3H, s, flavone CH$_3$) 2.5 (2H, t, CH$_2$CHO) 2.9 (2H, t, Fl'-CH$_2$) 7.3 (1H, dd, flavone CH in 6) 7.5–7.7 (6H, m, flavone CH in 7, and 5×phenyl CH) 8.1 (1H, dd, flavone CH in 5) 9.7 (1H, s, CHO)

2.3 ml of 6N hydrochloric acid in ethanol, a solution of 2.1 g of the above compound in 40 ml of methanol and 0.45 g of sodium cyanoborohydride are added in succession to a solution of 8 g of 1-(2-methoxyphenyl)piperazine in 30 ml of methanol. After stirring the reaction at ambient temperature for 24 hours, the mixture is poured into 500 ml of iced water and extracted with dichloromethane. The organic phase is washed with water, dried on anhydrous sodium sulphate and evaporated to dryness in vacuo. The residue is purified by flash chromatography using a silica gel column, eluting with ethyl acetate:petroleum ether (9:1). The fractions, containing the title product as a base, are evaporated to dryness in vacuo and an equivalent of methanesulphonic acid is added to the residue dissolved in 30 ml of dichloromethane. The solvent is evaporated off in vacuo and the residue is crystallized from acetone to give 2.35 g of the title compound (m.p. 141°–143° C.).

Example 54

8-[3-(4-phenyl-1-piperidinyl)propylcarbamoyl]-3-methyl-4-oxo-2-phenyl-4H-1-benzopyran methanesulphonate Fl'-Y3-(CH$_2$)$_3$-B3

This compound is prepared by the method described in Example 11, using 4-phenylpiperidine instead of 1-(2-methoxyphenyl)piperazine and conducting the reaction for 1 hour instead of 5 hours. Purification is carried out by flash chromatography using a silica gel column, eluting with dichloromethane:methanol (100:5). (M.P. 157°–159° C. (ethyl acetate). The respective base melts at (127) 147°–149° C. (ethanol).

Example 55

8-[3-(4,4-diphenyl-1-piperidinyl)propylcarbamoyl]-3-methyl-4-oxo-2-phenyl-4H-1-benzopyran methanesulphonate Fl'-Y3-(CH$_2$)$_3$-B5

This compound is prepared by the method described in Example 11, using 4,4-diphenylpiperidine instead of 1-(2-methoxyphenyl)piperazine and conducting the reaction for 2 hours instead of 5 hours. M.p. 221°–223° C. (ethyl acetate).

Example 56

8-{3-[4-(4-fluorobenzoyl)-1-piperidinyl]propylcarbamoyl}-3-methyl-4-oxo-2-phenyl-4H-1-benzopyran Fl'-Y3-(CH$_2$)$_3$-B4

This compound is prepared by the method described in Example 11, using 4-(4-fluorobenzoyl)piperidine instead of 1-(2-methoxyphenyl)piperazine and conducting the reaction for 30 minutes instead of 5 hours. Purification is carried out by flash chromatography using a silica gel column, eluting with dichloromethane:1N ammonia in methanol in a ratio gradually changing from 100:1 to 100:20. M.p. 181°–183° C. (ethanol).

Example 57

8-{3-[4-(2-oxo-1-benzimidizolinyl)-1-piperidinyl]-propylcarbamoyl}-3-methyl-4-oxo-2-phenyl-4H-1-benzopyran Fl'-Y3-(CH$_2$)$_3$-B6

This compound is prepared by the method described in Example 11, using 4-(2-oxo-1-benzimidizolinyl)-piperidine instead of 1-(2-methoxyphenyl)piperazine. Purification is carried out by flash chromatography using a silica gel column, eluting with chloroform:1N ammonia in methanol (100:3). M.p. 238°–241° C. (ethanol).

Example 58

8-{-[4(2-pyrimidinyl)-1-piperazinyl]propylcarbamoyl}-3-methyl-4-oxo-2-phenyl-4H-1-benzopyran methanesulphonate Fl'-Y3-(CH$_2$)$_3$-B2

This compound is prepared by the method described in Example 11, using 1-(2-pyrimidinyl)piperazine instead of 1-(2-methoxyphenyl)piperazine and conducting the reaction for 2 hours. The product is purified by flash chromatography using a silica gel column, eluting with chloroform:methanol 100:3. The desired fractions are dissolved in dichloromethane and an equivalent of methanesulphonic acid is added to the solution. After evaporation of the solvent in vacuo, the residue is boiled for 1 hour with ethyl acetate and then collected by filtration, m.p. 209°–210° C. The product so obtained contains 0.2 equivalents of ethyl acetate and 0.1 equivalents of water. The respective base melts at 178°–180° C. (ethanol).

Example 59

8-{3-[4-(2-hydroxyphenyl)-1-piperazinyl]propylcarbamoyl}-3-methyl-4-oxo-2-phenyl-4H-1-benzopyran Fl'-Y3-(CH$_2$)$_3$-B1(OH)

Operating as described in Example 11, but using 1-(2-hydroxyphenyl)-piperazine instead of 1-(2-methoxyphenyl)piperazine, heating for 1.5 hours instead of 5 hours, and using dichloromethane-methanol 100:3 to 100:10 as eluant for column chromatography, the title compound is obtained. M.p. 118°–120° C. (ethanol 95%).

Example 60

8-{4-[4-(2-methoxyphenyl)-1-piperazinyl]butylcarbamoyl}-3-methyl-4-oxo-2-phenyl-4H-1-benzopyran methanesulfonate Fl'-Y3-(CH₂)₄-B1(OCH₃)

This compound was prepared by the method used in Example 12, but using 4-[4-(2-methoxyphenyl)-1-piperazinyl]butylamine instead of 3-[4-(2-methoxyphenyl)-1-piperazinyl]propylamine. The reaction mixture was stirred at room temperature for 22 hours, diluted with water and filtered by suction, washing the insoluble solid with water. The crude residue was dried and purified by column chromatography on silica gel, eluting with ethyl acetate-methanol 9:1. The fractions containing the pure product as a base were collected, evaporated to dryness in vacuo and dissolved in dichloromethane. Methanesulfonic acid was added to the solution and the salt was precipitated by adding 2 volumes of ethyl acetate, filtered and recrystallized from ethanol to give the title compound, m.p. 230°–232° C. This product was showed to contain 0.3 molar equivalent of ethanol.

Example 61

8-{3-[4-(2-methoxyphenyl)-1-piperazinyl]propylsulfamyl}-3-methyl-4-oxo-2-phenyl-4H-1-benzopyran methanesulfonate Fl'-Y41-(CH₂)₃-B1(OCH₃)

This compound was obtained operating as described in Example 12 but using Intermediate VIII instead of 8-chlorocarbonyl-3-methyl-4-oxo-2-phenyl-4H-1-benzopyran and stirring for 24 hours instead of 2.5 hours. The crude was purified by column chromatography on silica gel, eluting with ethyl acetate-methanol 98.5:1.5. The collected fractions containing the pure product as a base, were evaporated to dryness in vacuo and dissolved in dichloromethane. Methanesulfonic acid was added to the solution and the solvent was removed by evaporation in vacuo. The crude salt was crystallized from ethanol to give the title compound, m.p. (196) 198°–200° C.

Example 62

8-{3-[N-methyl-2-(2-methoxyphenoxy)-ethylamino]-propylcarbamoyl}-3-methyl-4-oxo-2-phenyl-4H-1-benzopyran hydrochloride Fl'-Y3-(CH₂)₂-B7(OCH₃, H, CH₃, 2)

A solution of 10.5 ml of formaldehyde 40% in water was added to a suspension of 6.66 g of the compound prepared in Example 14 in 55 ml of acetonitrile and 20 ml of water. After stirring for 15 minutes at room temperature, 2.70 g of sodium cyanoborohydride 95% was added to the red solution and after an additional 15 minutes in the same conditions, 1.38 ml of acetic acid was added. After stirring for 3 hours, the solvents are removed in vacuo and the residue was rinsed with 250 ml of water and 250 ml of chloroform. After addition of 3N sodium hydroxide, the organic phase was separated off and the aqueous phase was extracted twice with chloroform. The solvent of the collected organic phases was evaporated in vacuo and the residue was purified by flash chromatography on silica gel, eluting with chloroform-5.2N methanolic ammonia 100:0.5 to 100:2. The collected fractions containing the pure title compound as a base were evaporated to dryness in vacuo and the residue was dissolved in hot ethanol. The solution was acidified with ethanolic hydrogen chloride and, after evaporation of the solvent in vacuo, the residue was rinsed with diethyl ether and stirred at room temperature. The crude product was collected by filtration and crystallized from acetonitrile to give 3.1 g of the title compound, m.p. 146°–148° C.

Example 63

8-{N-methyl-3-[4-(2-methoxyphenyl)-1-piperazinyl)-propionamido}-3-methyl-4-oxo-2-phenyl-4H-1-benzopyran methanesulfonate Fl'-Y34-(CH₂)₂-B1(OCH₃)

Operating as described in Example 37, but using Intermediate L instead of Intermediate X and stirring at 90° C. for 4 hours instead of 60° C. for 6 hours, the title compound was obtained as a crude base. After purification by column chromatography on silica gel, eluting with ethyl acetate-methanol 95:5, a crude methanesulfonate was obtained as described in Example 61 and crystallized from acetone to give the title compound, m.p. 200°–202° C.

Example 64

8-{3-[4-(2-methoxyphenyl)-1-piperazinyl]propylcarbamoyl}-3-phenyl-4-oxo-4H-1-benzopyran dimethanesulfonate Fl''-Y3-(CH₂)₃-B1(OCH₃)

The title compound was prepared operating as described in Example 12, but using Intermediate LVI instead of 8-chlorocarbonyl-3-methyl-4-oxo-2-phenyl-4H-1-benzopyran and stirring for 24 hours instead of 2.5 hours. The crude was purified by column chromatography, eluting with ethyl acetate methanol 92:8, and the pure base, obtained by evaporation in vacuo of the collected fractions, was dissolved in dichloromethane and added with two equivalents of methanesulfonic acid. The crude dimethanesulfonate, obtained after evaporation of the solvent, was recrystallized from acetone, m.p. 153°–156° C. (200)

Example 65

8-{3-[2-(3,4-dihydro-1,(2H)-naphthalenonyl)methylaminolpropylcarbamoyl}-3-methyl-4-oxo-2-phenyl-4H-1-benzopyran methanesulfonate Fl'-Y3-(CH₂)₃-B9(H)

A mixture of 6 g of Intermediate XLIII, 2.4 g of 2-methylene-α-tetralone [prepared as described in Org. Synth., 60, 88 (1981)] and 3.14 ml of triethylamine in 48 ml of anhydrous dimethylformamide was stirred at room temperature for 6 hours, then at 50° C. for additional 1 hour. The reaction mixture was diluted with water and extracted with dichloromethane: the organic layers were washed with water, dried on anhydrous sodium sulfate and evaporated to dryness in vacuo. The crude residue was purified twice by column chromatography eluting firstly with dichloromethane-methanol 95:5 and then with dichloromethane-methanolmethanolic ammonia (5.8N) 98:2:0.2, to give 1.74 g of the title compound as a base. The base was converted into the methanesulfonate by the procedure described in Example 61. The salt was recrystallized first from acetone and then from acetonitrile to give the title compound, m.p. (69) 157°–159° C.

Example 66

8-{2-[4-(2-methoxyphenyl)-1-piperazinyl]ethoxycarbonylmethyl}-3-methyl-4-oxo-2-phenyl-4H-1-benzopyran dihydrochloride Fl'-Y13-(CH₂)₂-B1(OCH₃)

The title compound was prepared by the method described in Example 5, but using Intermediate XLVII in place of 8-carboxy-3-methyl-4-oxo-2-phenyl-4H-1-benzopyran and 1-(2-chloroethyl)-4-(2-methoxyphenyl)-piperazine instead of 1-(3-chloropropyl)-4-(2- methoxyphenyl)piperazine. m.p. 193°–196° C. from ethanol/diethyl ether.

Example 67

8-{4-[4-(2-methoxyphenyl)-1-piperazinyl]butylsulfamyl}-3-methyl-4-oxo-2-phenyl-4H-1-benzopyran dimethanesulfonate Fl'-Y41-(CH$_2$)$_4$-B1(OCH$_3$)

The title compound was prepared as described in Example 61 but using 4-[4-(2-methoxyphenyl)-1-piperazinyl]butylamine instead of 3-[4-(2-methoxyphenyl)-1-piperazinyl]propylamine. The crude dimethanesulfonate was crystallized first from acetonitrile and then from ethanol, m.p. 172°–174° C.

Example 68

8-{N,2-tetrahydropyranyloxy-3-[4-(2-methoxyphenyl)-1-piperazinyl]propylcarbamoyl}-3-methyl-4-oxo-2-phenyl-4H-1-benzopyran methanesulfonate hemihydrate Fl'-Y47-(CH$_2$)$_3$-B1(OCH$_3$)

A solution of 3.6 g of 1-(3-chloropropyl)-4-(2-methoxyphenyl)piperazine in 30 ml of anhydrous dimethylformamide was added dropwise, under stirring at 0° C., to a mixture of 3.92 g of 2-tetrahydropyranyl hydroxylamine [prepared as described by R. N. Watrener et al., Angewandte Chem. Int. Ed., 5, 511 (1966)]. Stirring at 0° C. was continued for 2 hours, and then for 12 hours at 110° C. The reaction mixture was cooled to room temperature and dimethylformamide removed by distillation in vacuo. The residue was rinsed with water and extracted with ethyl acetate. The combined organic layers were washed with water, dried on anhydrous sodium sulfate and the solvent was evaporated to dryness in vacuo to give 4.39 g of 1-[3-(2-tetrahydropyranyloxyamino)propyl]-4-(2-methoxyphenyl)piperazine.

$^1$H-NMR (CDCl$_3$; ($\delta$))

| | | |
|---|---|---|
| 6.50–6.75 | (m; 4H) | aromatic protons |
| 5.20 | (bs; 1H) | NH |
| 4.60 | (m; 1H) | O—CH—O |
| 3.30–4.00 | (m; 5H) | OCH$_3$ and tetrahydropyran CH$_2$O |
| 2.80–3.20 | (m; 6H) | piperazine 2 × CH$_2$ alkyl chain CH$_2$N |
| 2.20–2.80 | (m; 6H) | piperazine 2 × CH$_2$, alkyl chain CH$_2$N |
| 1.30–2.00 | (m; 8H) | tetrahydropyran 3 × CH$_2$, alkyl chain C—CH$_2$—C |

A solution of 2.79 g of 8-chlorocarbonyl-3-methyl-4-oxo-2-phenyl-4H-1-benzopyran in 47 ml of chloroform was added dropwise at room temperature to a mixture of 3.26 g of the above-described Intermediate and 1.42 g of potassium carbonate in 47 ml of chloroform. The reaction mixture was stirred for 3 hours, then diluted with 75 ml of chloroform and washed three times with 1M sodium hydroxide; the organic layer was washed with water, dried on anhydrous sodium sulfate and evaporated to dryness in vacuo. The crude residue was purified by column chromatography on silica gel eluting with ethyl acetate methanol 98:2. The collected fractions were evaporated to dryness in vacuo to give 2.99 g of pure title compound as a base, which was dissolved in dichloromethane. Methanesulfonic acid was added to the solution and the solvent was removed by evaporation in vacuo. The crude salt was crystallized from ethyl acetate to yield the title compound, m.p. 159°–160° C.

Example 69

8-{4-[4-(2-methoxyphenyl)-1-piperazinyl]butyramido}-3-methyl-4-oxo-2-phenyl-4H-1-benzopyran methanesulfonate hemihydrate Fl'-Y33-(CH$_2$)$_3$-B1(OCH$_3$)

The title compound was prepared operating as described in Example 38, but using Intermediate XLVIII instead of Intermediate XLIV and stirring 1 hour at 70° C. and 2 hours at 130° C. instead of 7 hours at 100° C. After the usual workup, the crude residue was purified by column chromatography on silica-gel eluting with ethyl acetate-methanol 95:5. The fractions containing the pure title compound as a base were collected and evaporated to dryness in vacuo. The residue was dissolved in methylene chloride and one equivalent of methanesulfonic acid was added to the solution. After evaporation of the solvent to dryness in vacuo, the crude salt was crystallized from acetone, m.p. 175°–176° C.

Example 70

E-8-{2-[4-(2-methoxyphenyl)-1-piperazinyl]ethoxyiminomethyl}-3-methyl-4-oxo-2-phenyl-4H-1-benzopyran E-Fl'-Y11-(CH$_2$)$_2$-B1(OCH$_3$)

A solution of 5.4 g of 8-formyl-3-methyl-4-oxo-2-phenyl-4H-1-benzopyran and 5.13 g of Intermediate LII in 10 ml of chloroform, containing molecular sieves 3A, was stirred at reflux for 6 hours. Molecular sieves were removed by filtration and the solvent evaporated to dryness in vacuo. The crude product was purified by column chromatography on silica gel, eluting with ethyl acetate-petroleum ether 7:3; two groups of fractions were collected and the solvent evaporated in vacuo. The first eluted group of fractions (less polar) containing almost pure title compound; the second group (more polar) was a 1:1 mixture of the E and Z diastereomers, as determined as by
1H-NMR at 200MHz.

$^1$H-NMR (CDCl$_3$, ($\delta$))

| | | |
|---|---|---|
| 8.75 | (dd, 0.5H) | benzopyran CH in 7 (Z) |
| 8.65 | (s, 0.5H) | iminic CH (E) |
| 8.30 | (dd, 1H) | benzopyran CH in 5 (E+Z) |
| 8.15 | (dd, 0.5H) | benzopyran CH in 7 (E) |
| 8.00 | (s, 0.5H) | iminic CH (Z) |
| 7.60–7.75 | (m, 2H) | phenyl CH in 2' and 6' (E+Z) |
| 7.50–7.60 | (m, 3H) | phenyl CH in 3', 4' and 5' (E+Z) |
| 7.45 | (dd, 0.5H) | benzopyran CH in 6 (Z) |
| 7.41 | (dd, 0.5H) | benzopyran CH in 6 (E) |
| 6.70–7.10 | (m, 4H) | phenyl protons (E+Z) |
| 4.41 | (t, 2H) | CH$_2$O (E+Z) |
| 3.86 | (s, 3H) | CH$_3$O (E+Z) |
| 3.05–3.20 | (m, 4H) | piperazine 2 × CH$_2$ (E+Z) |
| 2.70–2.90 | (m, 6H) | piperazine 2 × CH$_2$ and CH$_2$N (E+Z) |
| 2.20 | (s, 1.5H) | benzopyran CH$_3$ in 3 (Z) |
| 2.18 | (s, 1.5H) | benzopyran CH$_3$ in 3 (E) |

The E diastereomer was crystallized from ethanolwater 2:1 to give 2.5 g of pure title compound, m.p. 107°–109° C.

Example 71

8-{N-hydroxy-3-[4-(2-methoxyphenyl)-1-piperazinyl]propylcarbamoyl}-3-methyl-4-oxo-2-phenyl-4H-1-benzopyran methanesulfonate×0.25 H$_2$O Fl'-Y5-(CH$_2$)$_3$-B1(OCH$_3$)

A solution of 2.04 g of compound of Example 68 as a base in 104 ml of 1.6N ethanolic hydrochloric acid was stirred for 12 hours at room temperature. Ethanol was removed by evaporation in vacuo and the residue was rinsed with 1N sodium hydroxide and dichloromethane. The organic layer was collected, washed with water, dried on anhydrous sodium sulfate and evaporated to dryness in vacuo. One molar equivalent of methanesulfonic acid was added to a solution of the residue in dichloromethane. The solvent was removed and the crude methanesulfonate crystallized from acetone to give 1.02 g of the title compound, m.p. 211°-213° C. The product contained 0.25 mole of water.

Example 72

E-8-{2-[2-[4-(2-methoxyphenyl)-1-piperazinyl]ethylcarbamoyl]ethenyl}-3-methyl-4-oxo-2-phenyl-4H-1-benzopyran methanesulfonate×1.2 $H_2O$ E-Fl'-Y10-$(CH_2)_2$-B1$(OCH_3)$ The title compound was obtained operating as described in Example 61 but using Intermediate IV instead of Intermediate VIII and 2-[4-(2-methoxyphenyl)-1-piperazinyl]ethylamine instead of the corresponding propylamine, in 1,1,2,2,-tetrachloroethylene as solvent. At the end, the reaction mixture was diluted with water and chloroform and washed with 1N aqueous sodium hydroxide, then with water. To the organic layer, after drying on anhydrous sodium sulfate, was added methanesulfonic acid and the solvents were evaporated to dryness in vacuo. The crude product was crystallized twice from isopropanol to give the title compound containing 1.2 molar equivalent of water (m.p. 124°-127° C.).

Example 73

8-{4-[4-(2-methoxyphenyl)-1-piperazinyl]butylsulfinyl}-3-methyl-4-oxo-2-phenyl-4H-1-benzopyran methanesulfonate Fl'-Y39-$(CH_2)_4$-B1$(OCH_3)$ The title compound was prepared according to Example 38, but using Intermediate LIV instead of Intermediate XLIV, stirring at 70° C. for 3 hours and again at 90° C. for 3 hours after adding catalytic quantity of potassium iodide (0.01 equivalents). Purification by column chromatography on silica gel, eluting with ethyl acetate-methanol 9:1, gave the title compound as base. To the crude base, dissolved in dichloromethane, was added one molar equivalent of methanesulfonic acid. After removal of the solvent by evaporation in vacuo, the resulting salt was crystallized from acetone to give the title compound (m.p. 183°-184° C.).

PHARMACOLOGICAL DATA

Methodology

Male Sprague Dawley rats [Crl: CD' BR] of 200–300 g b.w., female Albino Swiss mice [Crl: CD-1 (ICR) BR] 20–30 g b.w., and male Beagle dogs (10–12 kg bw) were obtained from Charles River, Italy and Nossan (Correzzana, Milan, Italy), respectively. Animals were housed with free access to food and water and maintained on forced light-dark cycle at 22°-24° C. until the day of experiments.

Acute toxicity:

The acute toxicity of synthesized compounds was evaluated in female albino Swiss mice after intraperitoneal and oral administration. Four logarithmic scaled doses of the compounds were dissolved or suspended in 0.5% Methocel and administered in a volume of 10 ml/kg to groups of 4 mice/dose. Mortality was recorded 7 days after the administration. Data analysis: the $LD_{50}$ values and their fiducial limits were calculated according to the method of Weil (*Biometrics*, 8:249, 1952).

Receptor Binding Studies:

-[$^3$H]prazosin binding ($\alpha_1$ receptors)

Rat cerebral cortices were homogenized in 50 volumes of original wet weight on ice-cold 50 mM Tris-HCl buffer pH 7.4. The homogenates were centrifuged at 48,000×g for 10 minutes, and the pellets were resuspended in the same volume of ice-cold buffer, centrifuged and resuspended two more times. The final pellets obtained were resuspended in the same volume of buffer and incubated according to the conditions reported in the table below.

The foregoing receptor binding studies, do well as the experimental data on dogs reported below establish compounds of the invention as $\alpha_1$-blockers, i.e. to be within a class of substances widely used as antihypertensive and anti-BPH agents. See, e.g., Frishman, W. H. et al., *Medical Clinics of N. America*, 72: 427, 1988 and references cited therein.

-[$^3$H]-8-OH-DPAT binding (5HT$_{1A}$ receptors)

Rat hippocampi were homogenized in 50 volumes of original wet weight on ice-cold 50 mM Tris-HCl buffer pH 7.4. The homogenates were centrifuged at 48,000×g for 10 minutes, and the pellets were resuspended in the same volume of ice-cold buffer, incubated for 10 minutes at 37° C., centrifuged and resuspended two more times.

The final pellets obtained were resuspended in the same volume of buffer and incubated according to the conditions reported in the table below.

These receptor binding studies serve to establish compounds of the present invention as ligands for the 5HT$_{1A}$ receptor. As previously reported, compounds that are 5HT$_{1A}$ ligands exert anxiolytic and antidepressant effects in animals and humans. (Hamon, M. et al., *Ann. N.Y. Acad. Sci.* 600: 114, 1990; Traber J., et al., *T.I.P.S.* 8: 437, 1987).

| | Receptor Binding Studies | |
|---|---|---|
| RECEPTOR/LIGAND Conditions | $\alpha_1$ adrenergic [$^3$H]prazosin | 5-HT$_{1A}$ serotonergic [$^3$H]8-OH-DPAT |
| [nM] ligand | 0.35 | 1.0 |
| preparation (c.m.p) | 1 ml | 1 ml |
| incubation buffer* | 10 mg/ml Tris HCl 50 mM pH 7.4 | 10 mg/ml Tris HCl 50 mM pH 7.4 |
| nonspecific binding | prazosin | 5-HT |
| incubation | 2 μM 25° 30 min | 10 μM 25° 30 min | c.m.p. = crude membrane preparation;
*containing ascorbic acid 1% and pargyline 10 μM The incubations were terminated after the appropriate time (see table) by rapid filtration through Whatman GF/B filters using a Brandel cell harvester. The filters were washed twice with 15 ml of ice-cold buffer (see table). The radioactivity retained on the filters was determined by liquid scintillation counting. Nonspecific binding (which amounted generally to 10–30%) was evaluated by adding high concentrations of the specific displacers (see table). All the compounds were initially tested at 1×10$^{-6}$M concentration, and in the presence of significant displacing activity, a complete competition curve was generated (down to a concentration of 10$^{-11}$M). All the samples were run in triplicate.

The competition curves were always analyzed (to evaluate the IC$_{50}$ values) by non linear curve fitting of the logistic equation according to the method reported by De Lean et al. (*Am. J. Physiol.*, 235:E97, 1978), utilizing the ALLFIT program (publicly available from the National Institutes of Health (N.I.H.) Bethesda, Md.) written for the IBM PC.

K+-induced contractions of rat bladder strips:

The whole bladder of the rat was removed and immediately placed in Krebs solution warmed at 37° C. Strips of detrusor muscle (20–30 mm long, 1–2 mm wide), were cut from the dome of the bladder. Each strip was placed in a 10 ml organ bath and connected, under a constant load of 1 g, to an isometric strain gauge (DY-1 Basile, Comerio (Varese) Italy). Contractions were recorded by means of a Basile 7070 polygraph. After a 60 minutes equilibration period the strips were exposed to KCl 80 mM final concentration. This produced a rapid phasic contraction followed by a slow ensuing and sustained tonic component. When the tonic contraction was stable, the strips were washed and 30 minutes later a new contraction was induced. After having recorded two or more reproducible responses, one concentration of the tested drugs was added to the bath and 30 minutes later a new contraction was induced.

The experimental groups consisted of at least 2 preparations taken from different animals for each concentration of drug tested. The $IC_{50}$ values of inhibition of agonistinduced contractions were evaluated by linear regression analysis.

Effects on Urethral Contractions and Blood Pressure in Dogs:

The experiments were performed according to the method of Imagawa et al. (*J. Pharmacol. Methods*, 22:103–111, 1989), with substantial modifications, as follows: Adult male beagle dogs, weighing 8–10 Kg, were anaesthetized with pentobarbital sodium (30 mg/Kg i.v. and 2 mg/Kg/h i.v.), intubated and spontaneously ventilated with air room. In order to monitor systemic blood pressure (BP), a PE catheter was introduced into the aortic arch through the right common carotid artery.

A collateral of the left femoral vein was cannulated for infusion of anaesthetic, and the right femoral vein was cannulated for administration of drugs. For intraarterial (i.a.) injection of noradrenaline (NA), a PE catheter was introduced into the lower portion of abdominal aorta via the right external iliac artery. Through such procedure, NA was selectively distributed to the lower urinary tract. Via a midline laparotomy, the urinary bladder and proximal urethra were exposed. In order to prevent the filling of the bladder, the two ureters were cannulated and the urine was led outside. In order to record the prostatic urethral pressure, a Mikro-tip catheter (6 F) was introduced into the bladder via the external urethral meatus, and withdrawn until the pressure transducer was positioned in the prostatic urethra. A ligature was secured between the neck of the bladder and urethra to isolate the response of the latter and avoid any interaction with the bladder. Another ligature was put around the Mikro-tip catheter at the external urethral meatus, to secure the catheter itself. After a stabilizing period following surgical procedure (30 min), in which arterial and prostatic urethral pressure were continuously monitored as basal values, i.a. administration of NA was made at intervals of 10 min. The dose of NA chosen was sufficient to produce an increase of at least 100% in urethral pressure. The test compounds were i.v. administered in a cumulative manner with intervals of 15–20 min between administrations.

I.a. injections of NA were repeated approximately 5 min. after every dosing of test compound.

Dose response curves were constructed computing the percent inhibition to the increase in urethral pressure (NA-induced), and the percent drop in blood pressure produced by the test compound. $ED_{25}$ for diastolic blood pressure (dose inducing a 25% decrease) and $ID_{50}$ (dose inducing a 50% inhibition of NA-induced increase in urethral pressure) were computed by means of linear regression analysis.

Results

Compounds as prepared in the Examples were tested according to the methods reported above, and the results are given in the Tables below, together with comparative results for the reference standard used.

Compounds having receptor affinity ($IC_{50}$ values) lower than about 500 nM are generally considered to have good affinity. Compounds with $IC_{50}$ of less than 100 nM are generally preferred.

TABLE I

| Compound Example No. | Receptor Binding $IC_{50}$ (nM) | | Acute Toxicity in Mice LD (mg/kg) | | K+ Stimulation of Rat Bladder $IC_{50}$ (nM) Contractions | |
|---|---|---|---|---|---|---|
| | $\alpha_1$ | $5\text{-}HT_{1A}$ | i.p. | p.o | Phasic | Tonic |
| 5 | 20 | 19 | 621 | >3000 | | |
| 6 | 107 | 1000 | 233 | | | |
| 7 | 86 | 155 | 384 | 1915 | | |
| 8 | 66 | 111 | >500 | 1915 | | |
| 11 | 29 | 9 | 247 | 297 | 2.9 | 3.0 |
| 13 | 68 | 229 | >1000 | >3000 | 10.0 | 10.0 |
| 16 | 220 | 1050 | 345 | 778 | 1.6 | 2.2 |
| 17 | 59 | 910 | 299 | 608 | 8.8 | 3.8 |
| 18 | 270 | >1000 | 457 | 3000 | | |
| 19 | 165 | 340 | >1000 | >3000 | | |
| 20 | 169 | 85 | 297 | 594 | 2.7 | 2.5 |
| 21 | 17 | 33 | 297 | 566 | 1.7 | 1.7 |
| 22 | 117 | 48 | >500 | >2000 | | |
| 24 | 690 | 212 | >1000 | >3000 | | |
| 26 | 270 | >1000 | >500 | >2000 | | |
| 27 | 23 | 124 | 399 | >3000 | 1.0 | 0.8 |
| 28 | 120 | 96 | 203 | 1127 | | |
| 29 | 86 | 45 | 730 | >3000 | 10.0 | 10.0 |
| 32 | 119 | 46 | 301 | >2000 | 10.0 | >10 |
| 33 | 17 | 38 | 399 | >2000 | 10.0 | 10.0 |
| 34 | 30 | 34 | >500 | | 2.8 | 3.6 |
| 37 | 32 | 77 | >500 | >2000 | | |
| 39 | 90 | 170 | >1000 | >3000 | | |
| 40 | 75 | 83 | 140 | 349 | 0.5 | 0.9 |
| 41 | 43 | 53 | 399 | 2241 | 0.7 | 1.4 |
| 42 | 111 | 39 | 459 | 2163 | 10.0 | 10.0 |
| 44 | 685 | 201 | 84 | 399 | 0.6 | 0.5 |
| 45 | 15 | 106 | · 329 | 1727 | | |
| 46 | 86 | 23 | | | | |
| 47 | 36 | 23 | 330 | 1047 | 2.7 | 5.2 |
| 48 | 104 | 5 | 500 | 1914 | | |
| 49 | 152 | 9 | 432 | >2000 | | |
| 51 | 22 | 84 | >500 | | | |
| 52 | 89 | 2 | | | | |
| 54 | 35 | 143 | 106 | 421 | | |
| 56 | 25 | 748 | >500 | | | |
| 57 | 69 | >1000 | 500 | >2000 | | |
| Flavox. | >>1000 | >>1000 | 385 | 808 | 13 | 13 |

TABLE II

| Effects on Urethral Contractility and Blood Pressure in Dogs | | | |
|---|---|---|---|
| Compound Example No. | Urethra $ED_{50}$ μg/kg | DBP $ED_{25}$ μg/kg | DBP/Urethra ratio |
| 5 | 37.0 | 1074 | 29.0 |
| 13 | 16.0 | 215 | 13.4 |
| 21 | 6.6 | 127 | 19.2 |

TABLE II-continued

Effects on Urethral Contractility and Blood Pressure in Dogs

| Compound Example No. | Urethra ED$_{50}$ µg/kg | DBP ED$_{25}$ µg/kg | DBP/Urethra ratio |
|---|---|---|---|
| 40 | 11.0 | 152 | 13.8 |
| 41 | 57.0 | 745 | 13.1 |
| 42 | 31.0 | 404 | 13.0 |
| 45 | 16.4 | 186 | 11.3 |
| 47 | 35.0 | 530 | 15.1 |
| 11 | 1.4 | 390 | 278.6 |
| 17 | 10.0 | 6.2 | 0.6* |
| 27 | 3.2 | 9.8 | 3.1* |
| Prazosin | 3.6 | 6.6 | 1.8* |
| Terflavoxate | >10000 | 6060 | — |

Urethra: active dose in inhibiting by 50% the noradrenaline induced contraction of urethra
DBP: active dose in lowering diastolic blood pressure by 25%
DBP/urethra: ratio between the active doses (selectivity index)
*non-selective: substantial effect on both urethra and DBP.

Effective Amounts

The following represent guidelines effective oral, parenteral or intravenous dose ranges expressed in mg/kg of body weight per day for the following uses:

| *In obstructive disorders of the lower urinary tract: | |
|---|---|
| General | 0.001–20 |
| Preferred | 0.05–1 |
| Most Preferred | 0.3 |
| *As antihypertensives: | |
| General | 0.01–20 |
| Preferred | 0.1–5 |
| Most Preferred | 1 |
| *As anxiolytics-antidepressants: | |
| General | 0.01–20 |
| Preferred | 0.05–5 |
| Most Preferred | 0.5 |
| *As bladder spasmolytics: | |
| General | 0.01–20 |
| Preferred | 0.02–10 |
| Most Preferred | 2 |

Patients in need of treatment by the present compounds and compositions also include humans that have one or more depression symptoms (as defined, e.g. in Harrison's Principles of Internal Medicine, XII Ed., McGraw-Hill, Inc., p. 2124) or humans that display anxiety symptoms (Harrison's, supra, pp. 2131-2134).

Selective use dosages, i.e. dosages that are active in the lower urinary tract without a substantial effect on the blood pressure depend on the particular compound employed but, generally, up to four times the ED$_{50}$ of a selective compound can be administered without substantial effect on blood pressure. Further refinements and optimization of dosages are possible using no more than routine experiment.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but the amount of active ingredient may be varied depending upon the particular form and may conveniently be between 5% to about 70% of the weight of the unit. The amount of active compound in such compositions is such that a suitable dosage will be obtained although the desired dosage can be obtained by administering a plurality of dosage forms. Preferred compositions and preparations according to the present invention are prepared so that an oral dosage unit form contains between 1.0-300 milligrams of active compound.

The tablets, pills, capsules, troches and the like may also contain for example the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates; citrates or phosphates and agents for the adjustment of tonicity such as sodium chloride or dextrose. The parenteral multiple dose vials may be of glass or plastic.

We claim:

1. A compound having the general formula I

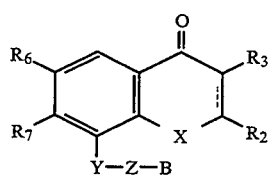

wherein
  ⸺ represents a single or double bond;
  X represents an oxygen or sulfur atom or a sulfinyl or sulfonyl group;
  R$_2$ represents a hydrogen atom or an alkyl, alkenyl, carbocyclic or heterocyclic group, each of which groups may optionally be substituted by one or more substituents selected from the group consisting of methyl, cyano, hydroxy, methoxy, fluoro, phenyl, phenoxy, trifluoromethyl, nitro, acylamino and benzoyl; and, additionally, carbocyclic can be amino substituted; with the proviso that the heterocyclic group cannot be linked through a nitrogen atom;

$R_3$ represents a hydrogen atom or a methyl, hydroxymethyl or phenyl group;

$R_6$ represents a hydrogen or halogen atom or a nitro, amino, acetylamino, alkylamino, dialkylamino, cyano, hydroxy, alkoxy or alkyl group;

$R_7$ represents a hydrogen atom or a methoxy group;

Y represents one of the following groups, each of which is depicted with its left hand end being the end which attaches to the heterobicyclic ring and its right hand end being the end which attaches to the group Z:

| | |
|---|---|
| —CO—, | (Y1) |
| —COO—, | (Y2) |
| —CONH—, | (Y3) |
| —CON(CH₃)—, | (Y4) |
| —CON(OH)—, | (Y5) |
| —CH(OH)—, | (Y6) |
| —CH(OAlkyl)—, | (Y7) |
| —CH=CH—, | (Y8) |
| —CH=CH—COO—, | (Y9) |
| —CH=CH—CONH—, | (Y10) |
| —CH=NO—, | (Y11) |
| —CH₂, | (Y12) |
| —CH₂COO—, | (Y13) |
| —CH₂CONH—, | (Y14) |
| —CH₂NH—, | (Y15) |
| —CH₂N(CH₃)—, | (Y16) |
| —CH₂N(COCH₃)—, | (Y17) |
| —CH₂N(CONH₂)—, | (Y18) |
| —CH₂NHCO—, | (Y19) |
| —CH₂N(CH₃)CO—, | (Y20) |
| —CH₂NH—CONH—, | (Y21) |
| —CH₂NHSO₂, | (Y22) |
| —CH₂O—, | (Y23) |
| —CH₂S—, | (Y24) |
| —CH₂SO—, | (Y25) |
| —CH₂SO₂—, | (Y26) |
| —CH₂SO₂NH—, | (Y27) |
| —CH₂SO₂N(CH₃)—, | (Y28) |
| —NH—, | (Y29) |
| —N(CH₃)—, | (Y30) |
| —N(COCH₃)—, | (Y31) |
| —N(CONH₂)—, | (Y32) |
| —NHCO—, | (Y33) |
| —N(CH₃)CO—, | (Y34) |
| —NH—CONH—, | (Y35) |
| —NHSO₂—, | (Y36) |
| —S—, | (Y38) |
| —SO—, | (Y39) |
| —SO₂—, | (Y40) |
| —SO₂NH—, | (Y41) |
| —SO₂N(CH₃)—, | (Y42) |
| —CONHO—, | (Y43) |
| —CON(COCH₃)—, | (Y44) |
| —CSNH—, | (Y45) |
| —CSN(CH₃)—, and | (Y46) |

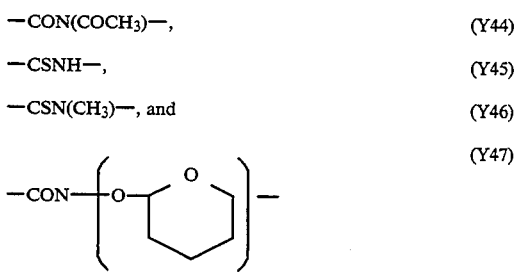
(Y47)

Z represents a linear or branched chain alkylene group having from 1 to 6 carbon atoms and optionally having one hydroxy substituent; and B represents one of the following groups:

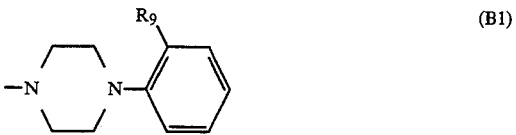
(B1)

wherein $R_9$ represents a hydrogen or chlorine atom or a methyl, hydroxy, methoxy or ethoxy group, or

(B2)

an enantiomer, diastereoisomer, N-oxide or pharmaceutically acceptable salt of such a compound.

2. A compound according to claim 1, wherein
 ═ represents a double bond,
 X represents an oxygen atom,
 $R_2$ represents a phenyl group,
 $R_3$ represents a methyl group,
 $R_6$ represents a hydrogen atom, and
 $R_7$ represents a hydrogen atom.

3. A compound according to claim 1 or claim 2 wherein Y represents one of the groups Y2, Y3, Y40 or Y41.

4. A compound according to claim 3 wherein Z represents a trimethylene or tetramethylene group.

5. A compound according to claim 3 wherein B represents the group B1.

6. A compound according to claim 3 wherein B represents the group B2.

7. A compound according to claim 5 wherein B represents a 4-(2methoxyphenyl)-1-piperazinyl group.

8. A compound according to claim 6 wherein B represents a 4-(2-methoxyphenyl)-1-piperazinyl group.

9. A compound selected from the group consisting of:

8-{2-[4-(2-methoxyphenyl)-1-piperazinyl]-1-oxoethyl}-3-methyl-4-oxo-2-phenyl-4H-1-benzopyran;

8-{2-[4-(2-methylphenyl)-1-piperazinyl]-1-oxoethyl}-3-methyl-4-oxo-2-phenyl-4H-1-benzopyran;

8-{2-[4-(2-ethoxyphenyl)-1-piperazinyl]-1-oxoethyl}-3-methyl-4-oxo-2-phenyl-4H-1-benzopyran;

8-{3-[4-(2-methoxyphenyl)-1-piperazinyl]-1-oxopropyl}-3-methyl-4-oxo-2-phenyl-4H-1-benzopyran;

8-{3-[4-(2-methoxyphenyl)-1-piperazinyl]-propoxycarbonyl}-3-methyl-4-oxo-2-phenyl-4H-1-benzopyran;

8-{2-[4-(2-methoxyphenyl)-1-piperazinyl]-ethoxycarbonyl}-3-methyl-4-oxo-2-phenyl-4H-1-benzopyran;

8-{3-[4-(2-chlorophenyl)-1-piperazinyl]-propoxycarbonyl}-3-methyl-4-oxo-2-phenyl-4H-1-benzopyran;

8-[3-(4-phenyl-1-piperazinyl)-propoxycarbonyl]-3-methyl-4-oxo-2-phenyl-4H-1-benzopyran;

8-{3-[4-(2-methoxyphenyl)-1-piperazinyl]-2-methyl-2-propoxycarbonyl}-3-methyl-4-oxo-2-phenyl-4H-1-benzopyran;

8-{3-[4-(2-methoxyphenyl)-1-piperazinyl]-propylcarbamoyl}-3-methyl-4-oxo-2-phenyl-4H-1-benzopyran;

8-{2-[4-(2-methoxyphenyl)-1-piperazinyl]-ethylcarbamoyl}-3-methyl-4-oxo-2-phenyl-4H-1benzopyran;

8-[3-(4phenyl-1-piperazinyl)-propylcarbamoyl]-3-methyl-4-oxo-2-phenyl-4H-1-benzopyran;

8-{N-methyl-2-[4-(2-methoxyphenyl)-1-piperazinyl]-ethylcarbamoyl}-3-methyl-4-oxo-2-phenyl-4H-1-benzopyran;

8-{1-hydroxy-2-[4-(2-methoxyphenyl)-1-piperazinyl]-ethyl}-3-methyl-4-oxo-2-phenyl-4H-1-benzopyran;

8-{1-hydroxy-2-[4-(2-methylphenyl)-1-piperazinyl]-ethyl}-3-methyl-4-oxo-2-phenyl-4H-1-benzopyran;

8-{1-hydroxy-2-[4-(2-ethoxyphenyl)-1-piperazinyl]-ethyl}-3-methyl-4-oxo-2-phenyl-4H-1-benzopyran;

8-{1-hydroxy-3-[4-(2-methoxyphenyl)-1-piperazinyl]-propyl}-3-methyl-4-oxo-2-phenyl-4H-1-benzopyran;

8-{1-hydroxy-4-[4-(2-methoxyphenyl)-1-piperazinyl]-butyl}-3-methyl-4-oxo-2-phenyl-4H-1-benzopyran;

8-{1-ethoxy-2-[4-(2-methoxyphenyl)-1-piperazinyl]-ethyl}-3-methyl-4-oxo-2-phenyl-4H-1-benzopyran;

8-{N-methyl-2-[4-(2-methoxyphenyl)-1-piperazinyl]-ethylaminomethyl}-3-methyl-4-oxo-2-phenyl-4H-1-benzopyran;

8-{N-acetyl-2-[4-(2-methoxyphenyl)-1-piperazinyl]-ethylaminomethyl}-3-methyl-4-oxo-2-phenyl-4H-1-benzopyran;

8-[4-(2-methoxyphenyl)-1-piperazinylacetamidomethyl]-3-methyl-4-oxo-2-phenyl-4H-1-benzopyran;

8-{N-methyl-2-[4-(2-methoxyphenyl)-1-piperazinyl]-acetamidomethyl}-3-methyl-4-oxo-2-phenyl-4H-1-benzopyran;

8-{2-[4-(2-methoxyphenyl)-1-piperazinyl]-ethoxymethyl}-3-methyl-4-oxo-2-phenyl-4H-1-benzopyran;

8-{2-[4-(2-methoxyphenyl)-1-piperazinyl]-ethylthiomethyl}-3-methyl-4-oxo-2-phenyl-4H-1-benzopyran;

8-{2-[4-(2-methoxyphenyl)-1-piperazinyl]-ethylsulfinylmethyl}-3-methyl-4-oxo-2-phenyl-4H-1-benzopyran;

8-{2-[4-(2-methoxyphenyl)-1-piperazinyl]-ethylsulfonylmethyl}-3-methyl-4-oxo-2-phenyl-4H-1-benzopyran;

8-{2-[4-(2-methoxyphenyl)-1-piperazinyl]-ethylamino}-3-methyl-4-oxo-2-phenyl-4H-1-benzopyran;

8-{3-[4-(2-methoxyphenyl)-1-piperazinyl]-propylamino}-3-methyl-4-oxo-2-phenyl-4H-1-benzopyran;

8-{4-[4-(2-methoxyphenyl)-1-piperazinyl]-butylamino}-3-methyl-4-oxo-2-phenyl-4H-1-benzopyran;

8-{N-methyl-3-[4-(2-methoxyphenyl)-1-piperazinyl]-propylamino}-3-methyl-4-oxo-2-phenyl-4H-1-benzopyran;

8-{N-acetyl-3-[4-(2-methoxyphenyl)-1-piperazinyl]-propylamino}-3-methyl-4-oxo-2-phenyl-4H-1-benzopyran;

8-{3-[4-(2-methoxyphenyl)-1-piperazinyl]-propionamido}-3-methyl-4-oxo-2-phenyl-4H-1-benzopyran;

8-{2-[4-(2-methoxyphenyl)-1-piperazinyl]-ethylureido}-3-methyl-4-oxo-2-phenyl-4H-1-benzopyran;

8-{3-[4-(2-methoxyphenyl)-1-piperazinyl]-propylthio}-3-methyl-4-oxo-2-phenyl-4H-1-benzopyran;

8-{3-[4-(2-methoxyphenyl)-1-piperazinyl]-propylsulfonyl}-3-methyl-4-oxo-2-phenyl-4H-1-benzopyran;

8-{2-[4-(2-methoxyphenyl)-1-piperazinyl]-ethylsulfamyl}-3-methyl-4-oxo-2-phenyl-4H-1-benzopyran;

8-{N-methyl-2-[4-(2-methoxyphenyl)-1-piperazinyl]-ethylsulfamyl}-3-methyl-4-oxo-2-phenyl-4H-1-benzopyran;

8-{N-aminocarbonyl-3-[4-(2-methoxyphenyl)-1-piperazinyl]-propylamino}-3-methyl-4-oxo-2-phenyl-4H-1-benzopyran;

8-{4-[4-(2-methoxyphenyl)-1-piperazinyl]-1-oxobutyl}-3-methyl-4-oxo-2-phenyl-4H-1-benzopyran;

8-{4-[4-(2-methoxyphenyl)-1-piperazinyl]butyl}-3-methyl-4-oxo-2-phenyl-4H-1-benzopyran;

8-{-[4(2-pyrimidinyl)-1-piperazinyl]propylcarbamoyl}-3-methyl-4-oxo-2-phenyl-4H-1-benzopyran;

8-{3-[4-(2-hydroxyphenyl)piperazinyl]propylcarbamoyl}-3-methyl-4-oxo-2-phenyl-4H-1-benzopyran;

8-{4-[4-(2-methoxyphenyl)-1-piperazinyl]butylcarbamoyl}-3-methyl-4-oxo-2-phenyl-4H-1-benzopyran;

8-{3-[4-(2-methoxyphenyl)-1-piperazinyl]propylsulfamyl}3-methyl-4-oxo-2-phenyl-4H-1-benzopyran;

8-{N-methyl-3-[4-(2-methoxyphenyl)-1-piperazinyl]-propionamido}-3-methyl-4-oxo-2-phenyl-4H-1-benzopyran;

8-{3-[4-(2-methoxyphenyl)-1-piperazinyl]propylcarbamoyl}3-phenyl-4-oxo-4H-1-benzopyran;

8-{2-[4-(2-methoxyphenyl)-1-piperazinyl]ethoxycarbonylmethyl}-3-methyl-4-oxo-2-phenyl-4H-1-benzopyran;

8-{4-[4-(2-methoxyphenyl)-1-piperazinyl]butylsulfamyl}-3-methyl-4-oxo-2-phenyl-4H-1-benzopyran;

8-{N,2-tetrahydropyranyloxy-3-[4-(2-methoxyphenyl)-1-piperazinyl]-propylcarbamoyl}-3-methyl-4-oxo-2-phenyl-4H-1-benzopyran;

8-{4-[4-(2-methoxyphenyl)-1-piperazinyl]butyramido}-3-methyl-4-oxo-2-phenyl-4H-1-benzopyran;

E-8-{2-[4-(2-methoxyphenyl)-1-piperazinyl]ethoxyiminomethyl}-3-methyl-4-oxo-2-phenyl-4H-1-benzopyran;

8-{N-hydroxy-3-[4-(2-methoxyphenyl)-1-piperazinyl]-propylcarbamoyl}-3-methyl-4-oxo-2-phenyl-4H-1-benzopyran;

E-8-{2-[2-[4-(2-methoxyphenyl)-1-piperazinyl]ethylcarbamoyl]ethenyl}-3-methyl-4-oxo-2-phenyl-4H-1-benzopyran;

8-}4-[4-(2-methoxyphenyl)-1-piperazinyl]butylsulfinyl}-3-methyl-4-oxo-2-phenyl-4H-1-benzopyran; or their pharmaceutically acceptable salts.

10. A compound according to claim 2 wherein B is of the formula B1, $R_9$ is chlorine, methyl, hydroxy, methoxy or ethoxy, and Z is $CH_2—CH(OH)—CH_2$.

11. A compound according to claim 10 wherein $R_9$ is methoxy.

12. A compound according to claim 7 which is 8-{3-[4-(2-methoxyphenyl)-1-piperazinyl]-propylcarbamoyl}-3-methyl-4-oxo-2-phenyl-4H-1-benzopyran or a pharmaceutically acceptable salt thereof.

13. A method for blocking α1 adrenergic receptors in a mammalian cell possessing such a receptor, the method comprising delivering to the extracellular medium surrounding said cell an amount of a compound according to claim 1, said amount being effective to block said receptor.

14. A method for interacting with 5-HT$_{1A}$ serotonergic receptors in a cell possessing such a receptor, the method comprising delivering to the extracellular medium surrounding said cell an amount of a compound according to claim 1 effective to interact with said receptor.

15. A method for preventing contractions of the urethral tract, including prostrate, of a mammal comprising delivering to the urethra said tract of said mammal a spasmolytic effective amount of a compound of claim 1.

16. A method for selectively preventing noradrenaline-induced contractions of the urethra of a mammal comprising delivering to said urethra an amount of a compound of claim 2 effective to prevent said contractions but ineffective to substantially reduce the diastolic blood pressure of said mammal.

17. A method for preventing potassium-ion induced contractions of the bladder of a mammal comprising delivering to said bladder a contraction-antagonistic effective amount of a compound according to claim 1.

18. A method of lowering diastolic blood pressure in a mammal comprising administering to said mammal an effective amount of a compound according to claim 1.

19. A pharmaceutical composition comprising a compound according to claim 1 in admixture with a pharmaceutically acceptable diluent or carrier.

20. A method of lowering diastolic blood pressure in a mammal comprising administering to said mammal an effective amount of a compound according to claim 2.

21. A method of lowering diastolic blood pressure in a mammal comprising administering to said mammal an effective amount of a compound according to claim 3.

22. A method of lowering diastolic blood pressure in a mammal comprising administering to said mammal an effective amount of a compound according to claim 4.

23. A method of lowering diastolic blood pressure in a mammal comprising administering to said mammal an effective amount of a compound according to claim 5.

24. A method of lowering diastolic blood pressure in a mammal comprising administering to said mammal an effective amount of a compound according to claim 6.

25. A method of lowering diastolic blood pressure in a mammal comprising administering to said mammal an effective amount of a compound according to claim 7.

26. A method of lowering diastolic blood pressure in a mammal comprising administering to said mammal an effective amount of a compound according to claim 8.

27. A method of lowering diastolic blood pressure in a mammal comprising administering to said mammal an effective amount of a compound according to claim 9.

28. A method of lowering diastolic blood pressure in a mammal comprising administering to said mammal an effective amount of a compound according to claim 10.

29. A method of lowering diastolic blood pressure in a mammal comprising administering to said mammal an effective amount of a compound according to claim 11.

* * * * *